United States Patent
Dobosy et al.

(10) Patent No.: US 12,024,742 B2
(45) Date of Patent: Jul. 2, 2024

(54) RNASE H2 MUTANTS THAT REDUCE PRIMER DIMERS AND OFF-TARGET AMPLIFICATION IN RHPCR-BASED AMPLICON SEQUENCING WITH HIGH-FIDELITY DNA POLYMERASES

(71) Applicant: Integrated DNA Technologies, Inc., Coralville, IA (US)

(72) Inventors: Joseph Dobosy, Coralville, IA (US); John Froehlig, Jr., North Liberty, IA (US); Katherine Perschbacher, Coralville, IA (US); Kristin Beltz, Cedar Rapids, IA (US); Scott Rose, Coralville, IA (US); Mark Aaron Behlke, Coralville, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 0 days.

(21) Appl. No.: 17/558,994

(22) Filed: Dec. 22, 2021

(65) Prior Publication Data
US 2022/0348997 A1 Nov. 3, 2022

Related U.S. Application Data

(60) Provisional application No. 63/277,273, filed on Nov. 9, 2021, provisional application No. 63/130,548, filed on Dec. 24, 2020.

(51) Int. Cl.
*C12Q 1/6848* (2018.01)
*C12N 9/22* (2006.01)
*C12Q 1/6853* (2018.01)
*C12Q 1/686* (2018.01)

(52) U.S. Cl.
CPC ............. *C12Q 1/6848* (2013.01); *C12N 9/22* (2013.01); *C12Y 301/26004* (2013.01); *C12Q 1/6853* (2013.01); *C12Q 1/686* (2013.01)

(58) Field of Classification Search
CPC .... C12Q 1/6848; C12Q 1/6853; C12Q 1/686; C12N 9/22; C12Y 301/26004
See application file for complete search history.

(56) References Cited

U.S. PATENT DOCUMENTS

| | | | |
|---|---|---|---|
| 10,760,074 B2 * | 9/2020 | Usui | C12N 15/1096 |
| 2018/0057868 A1 * | 3/2018 | Walder | C12Q 1/6806 |

FOREIGN PATENT DOCUMENTS

| | | | | |
|---|---|---|---|---|
| WO | 2008/063194 A1 | 5/2008 | | |
| WO | 2010/026933 A1 | 3/2010 | | |
| WO | WO-2015073931 A1 * | 5/2015 | ........... | C12N 9/1252 |
| WO | 2018/031625 A2 | 2/2018 | | |

OTHER PUBLICATIONS

Cohen GN et al. Mol Microbiol. Mar. 2003;47(6):1495-512 (Year: 2003).*
NCBI 2DFH_A (NCBI Database, PDB: 2DFH_A, published Dec. 1, 2020, 2 pages) (Year: 2020).*
GenBank CAB49440 (NCBI Database, GenBank accession CAB49440, published Mar. 7, 2015, 2 pages) (Year: 2015).*
GenBank QEK79383 (NCBI Database, GenBank accession QEK79383, published Sep. 3, 2019, 2 pages) (Year: 2019).*
International Search Report for WO/2022/140553 (PCT/US2021/064879) (dated Apr. 22, 2022).
Written Opinion of International Searching Authority for WO/2022/140553 (PCT/US2021/064879) (dated Apr. 22, 2022).

* cited by examiner

*Primary Examiner* — Nancy J Leith
*Assistant Examiner* — Douglas Charles Ryan
(74) *Attorney, Agent, or Firm* — Klintworth & Rozenblat IP LLP

(57) ABSTRACT

The present invention pertains to hybrid RNase H2 proteins that include fragments of amino acid sequences from *Pyrococcus abyssi* (P.a.), *Thermococcus kodakarensis* (T.kod), and *Pyrococcus furiosus* organisms, as well as methods of using the same to improve mismatch discrimination and activity in a high-fidelity DNA polymerase buffer.

11 Claims, 4 Drawing Sheets

Specification includes a Sequence Listing.

RNASE H2 MUTANTS THAT REDUCE PRIMER DIMERS AND OFF-TARGET AMPLIFICATION IN RHPCR-BASED AMPLICON SEQUENCING WITH HIGH-FIDELITY DNA POLYMERASES

CROSS-REFERENCE TO RELATED APPLICATIONS

This application claims benefit of priority under 35 U.S.C. 119 to U.S. Provisional Patent Application Ser. No. 63/130,548, filed Dec. 24, 2020 and entitled "RNASE H2 MUTANTS THAT ENHANCE MISMATCH DISCRIMINATION AND ACTIVITY IN HIGH-FIDELITY POLYMERASE BUFFER," and U.S. Provisional Patent Application Ser. No. 63/277,273, filed Nov. 9, 2021 and entitled "RNASE H2 MUTANTS THAT REDUCE PRIMER DIMERS AND OFF-TARGET AMPLIFICATION IN RHPCR-BASED AMPLICON SEQUENCING WITH HIGH-FIDELITY DNA POLYMERASES," the contents of which are herein incorporated by reference in their entirety.

FIELD OF THE INVENTION

This invention pertains to Type II RNase H (hereinafter RNase H2) hybrid enzyme variants and methods of cleaving a nucleic acid strand to initiate, assist, monitor or perform biological assays.

SEQUENCE LISTING

The instant application contains a Sequence Listing that has been submitted in ASCII format via EFS-Web and is hereby incorporated by reference in its entirety. The ASCII copy, created on Mar. 24, 2022, is named IDT01-018-US_ST25.txt, and is 76,640 bytes in size.

BACKGROUND OF THE INVENTION

The family of RNase H2 enzymes has been extensively characterized. These enzymes have substrate specificity for cleaving a single ribonucleotide embedded within a DNA sequence (in duplex form) (Eder, et al., (1993) *Biochimie*, 75, 123-126). Interestingly, cleavage occurs on the 5' side of the RNA residue (See Scheme I). A summary of these enzymes, their properties and applications in biological assays is summarized in U.S. Pat. No. 8,911,948 B2 to Walder et al.

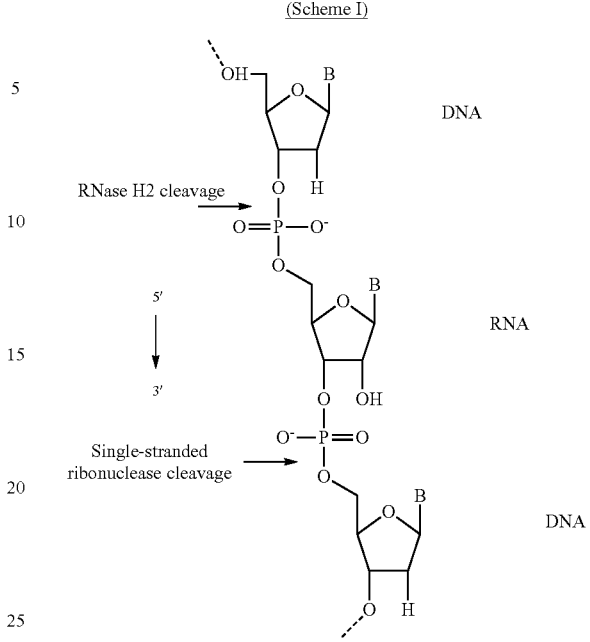

(Scheme I)

The RNase H2 enzyme isolated from the hyperthermophile *Pyrococcus abyssi* (P.a.) cleaves on the 5' side of a ribonucleotide embedded in a nucleic acid strand that is otherwise entirely made of DNA. RNase H2-dependent PCR (rhPCR) improves the specificity of PCR using a thermostable RNase H2 enzyme to cleave a primer containing a single ribonucleotide near the 3' end, removing a blocking group on the 3' terminus (Dobosy et al., 2011; U.S. Pat. No. 8,911,948 B2). This primer is initially incapable of extension by DNA polymerase, but upon removal of the blocking group from the 3' end by RNase H2, the primer is capable of being extended. P.a. RNase H2 is sensitive to single-base mismatches in the DNA-RNA heteroduplex near the ribonucleotide and cleaves a mismatch-containing template at a much-reduced rate, which allows the perfectly matched duplex to be preferentially cleaved and extended. This results in increased specificity in the rhPCR reaction, and lowers primer-dimer formation and other off-target amplifications.

Despite the enhancement rhPCR brings to the specificity of PCR, it currently has limitations. The apparent mismatch discrimination of rhPCR is lower than what should be theoretically achievable. WT P.a. RNase H2 recognizes single-base mismatches directly opposite of the RNA base to a high degree, though with varying efficiency depending on the nature of the mismatch. In addition, the native enzyme has comparatively limited mismatch discrimination at positions directly 5' or 3' of the RNA base. Despite this limitation, placing mutations at these locations can be advantageous. As an example, a mismatch directly 5' of the RNA can be used as a secondary selection step with the use of a discriminatory DNA polymerase (such as H784Q *Thermus aquaticus* DNA polymerase) in PCR amplification after primer cleavage (See U.S. patent application Ser. No. 15/361,280). Placing a mismatch 3' of the RNA reduces the likelihood of template conversion, as the mismatch recognition will happen with every cycle rather than once during template conversion.

Despite the utility of rhPCR, mismatch discrimination of wild type P.a. RNase H2 can be "leaky", resulting in some amplification of primer dimers. Primer dimers generated during amplification of sequencing libraries are problematic because they can bind to the Illumina flow cell and undergo sequencing, but do not provide any meaningful data. High levels of primer dimer decrease the fraction of reads mapping to the target of interest, ultimately reducing assay sensitivity or requiring a significant increase in sequencing cost to generate the number of on-target reads necessary for detection of low frequency variants. Low frequency variant detection can also be affected by the introduction of amplification errors during PCR. The error rate can be lowered with the use of a high fidelity DNA polymerase and optimized buffer conditions. However, these buffer conditions reduce the enzymatic activity and mismatch sensitivity of wild type P.a. RNase H2 in rhPCR.

It has previously been shown that the use of RNase H2 mutants generated by partial recombination of amino acid sequences of wild type P.a. RNase H2 with sequences from other related species results in improved RNase H2 enzymatic activity in high fidelity DNA polymerase buffer. Two of these mutants, Q48R SEL29 RNase H2 and A107V SEL29 RNase H2, were shown to have improved enzymatic activity using a *Thermococcus kodakarensis* (KOD) DNA polymerase reaction buffer. In addition, both mutants showed enhanced mismatch discrimination opposite the RNA base, as well as mismatches 3' and 5' of the RNA base, compared to wild type P.a. RNase H2. See U.S. Provisional Patent Application Ser. No. 63/130,548, filed Dec. 24, 2020, and entitled "RNASE H2 MUTANTS THAT ENHANCE MISMATCH DISCRIMINATION AND ACTIVITY IN HIGH-FIDELITY POLYMERASE BUFFER", the contents of which is incorporated by reference in its entirety.

The present disclosure pertains to one of these novel hybrid RNase H2 enzyme variants, Q48R SEL29 RNase H2, in a multiplex rhAmpSeq workflow containing a high-fidelity DNA polymerase and buffer. Compared to wild type P.a. RNase H2, Q48R SEL29 RNase H2 reduces the primer dimer produced during PCR amplification, thereby improving the mapping rate and on-target rate. While improving these metrics, Q48R SEL29 RNase H2 had no effect on other critical sequencing metrics including amplicon uniformity, amplicon dropout rates, and amplicon uniformity distributions.

BRIEF SUMMARY OF THE INVENTION

In a first aspect, a hybrid RNase H2 protein is provided. The hybrid RNase H2 protein includes fragments of amino acid sequences from *Pyrococcus abyssi* (P.a.), *Thermococcus kodakarensis* (T.kod), and *Pyrococcus furiosus* organisms.

In a second aspect, a recombinant nucleic acid encoding any of the hybrid RNase H2 proteins disclosed herein is provided.

In a third aspect, a method for conducting primer extension is provided. The method includes the step of contacting a hybrid RNase H2 protein as disclosed herein with a primer, a polynucleotide template, nucleoside triphosphates and a DNA polymerase under conditions suitable for a primer extension method, thereby producing an extended primer.

In a fourth aspect, a reaction mixture is provided. The reaction mixture includes a hybrid RNase H2 protein as described herein, at least one primer, a polynucleotide template, nucleoside triphosphates and a DNA polymerase.

In a fifth aspect, a method for performing rhPCR is provided. The method includes the step of performing primer extension with a hybrid RNase H2 as described herein, a DNA polymerase, and a primer.

In a sixth aspect, a method of amplifying a target DNA sequence is provided. The method includes several steps. The first step is providing a reaction mixture that includes the following: (i) an oligonucleotide primer having a cleavage domain, which is cleavable by an RNase H2 enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis; (ii) a sample nucleic acid that may or may not the target sequence; (iii) a DNA polymerase, and (iv) a hybrid RNase H2 protein as disclosed herein. The second step includes hybridizing the oligonucleotide primer to the target DNA sequence to form a double-stranded substrate. The third step is cleaving the hybridized oligonucleotide primer with said hybrid RNase H2 enzyme at a cleavage site within or adjacent to the cleavage domain to remove the blocking group from the oligonucleotide primer.

In a seventh aspect, a kit for producing an extended primer is provided. The kit includes at least one container providing a hybrid RNase H2 protein as disclosed herein.

In an eighth aspect, a kit for performing amplification of a target DNA sequence is provided. The kit includes a reaction buffer that includes an RNase H2 as described herein and a high-fidelity archaeal DNA polymerase.

In a ninth aspect, a method of preparing an amplicon library of template nucleic acids is provided. The method includes several steps. The first step is forming a mixture that includes a population of nucleic acids, at least block-cleavable primer, a hybrid RNase H2 protein, dNTPs, a DNA polymerase and a buffer such that a hybrid duplexes form between the at least block-cleavable primer and the population of nucleic acids in the mixture. The second step is cleaving the at least one block-cleavable primer with the hybrid RNase H2 protein to generate at least one active primer capable of primer extension by the DNA polymerase. The third step is extending the at least one active primer with the DNA polymerase in the buffer under conditions that permit amplification of one or more template nucleic acids from the population of nucleic acids, thereby generating the amplicon of template nucleic acids. In a first respect, the hybrid RNase H2 protein is selected from Q48R SEL29 (SEQ ID NO.:18), or others. In a second respect, the DNA polymerase is KOD DNA polymerase or other high-fidelity archaeal DNA polymerases. In a third respect, the buffer is a high-fidelity archaeal DNA polymerase buffer.

In a tenth aspect, a method of performing massively parallel sequencing is provided. The method includes several steps. The first step is preparing a library population of template nucleic acids using a population of nucleic acids, a hybrid RNase H2 mutant protein, at least one block-cleavable primer, a DNA polymerase, dNTPs and buffer in a PCR method. The second step is sequencing a plurality of desired template nucleic acids from the library population of template nucleic acids. In a first respect, the hybrid RNase H2 protein is selected from Q48R SEL29 (SEQ ID NO.:18), or others.

In an eleventh aspect, a method of detecting a SNP-containing nucleic acid template from an amplicon library of nucleic acid templates is provided. The method includes several steps. A first step includes forming a mixture that includes an amplicon library of nucleic acid templates; at least one blocked-cleavable primer; a hybrid mutant RNase H2 protein; dNTPs; a DNA polymerase; and a buffer. A hybrid duplex forms between the at least block-cleavable primer and the SNP-containing nucleic acid template in the amplicon library of nucleic acid templates in the mixture. The second step includes cleaving the at least one block-cleavable primer of the hybrid duplex with the hybrid RNase H2 protein to generate at least one active primer capable of primer extension of the hybrid duplex by the DNA polymerase. The third step includes extending the at least one active primer in the duplex with the DNA polymerase in the buffer under conditions that permit amplification of one or more template nucleic acids from the amplicon library of nucleic acid templates, thereby detecting the SNP-containing nucleic acid template. In a first respect, the method includes a hybrid mutant RNase H2 protein selected from Q48R SEL29 (SEQ ID NO.:18), or others. In a second respect, the method includes a buffer being a high-fidelity archaeal DNA polymerase buffer.

In a twelfth aspect, a method of performing a loop-mediated amplification reaction is provided. The method includes two steps. A first step includes forming a mixture that includes a nucleic acid template; four blocked-cleavable primers, wherein the blocked-cleavable primers form a duplex with the nucleic acid template that is a substrate for an RNase H2 protein; an RNase H2 protein, wherein the RNase H2 protein is selected from Q48R SEL29 (SEQ ID NO.:18) or others; a DNA polymerase protein; dNTPs; and a buffer. A second step includes performing isothermal amplification cycles with the mixture.

In a thirteenth aspect, a method of performing a rhPCR assay having reduced primer dimer formation is provided. The method includes performing primer extension with Q48R SEL29 RNase H2 (SEQ ID NO.:18). The reduced primer dimer formation corresponds to a reduced amount of primer dimers formed during the rhPCR assay with Q48R SEL29 RNase H2 (SEQ ID NO.:18) when compared to rhPCR assays conducted with wild-type P.a. RNase H2 (SEQ ID NO.: 1).

In a fourteenth aspect, a method of performing a rhPCR assay having an improved mapping rate and on-target rate for desired products is provided. The method includes performing primer extension with Q48R SEL29 RNase H2 (SEQ ID NO.:18). The improved mapping rate and on-target rate correspond to an increased mapping and on-target amplification of desired products formed during the rhPCR assay with Q48R SEL29 RNase H2 (SEQ ID NO.:18) when compared to rhPCR assays conducted with wild-type P.a. RNase H2 (SEQ ID NO.: 1).

DETAILED DESCRIPTION OF THE INVENTION

Figure 1:
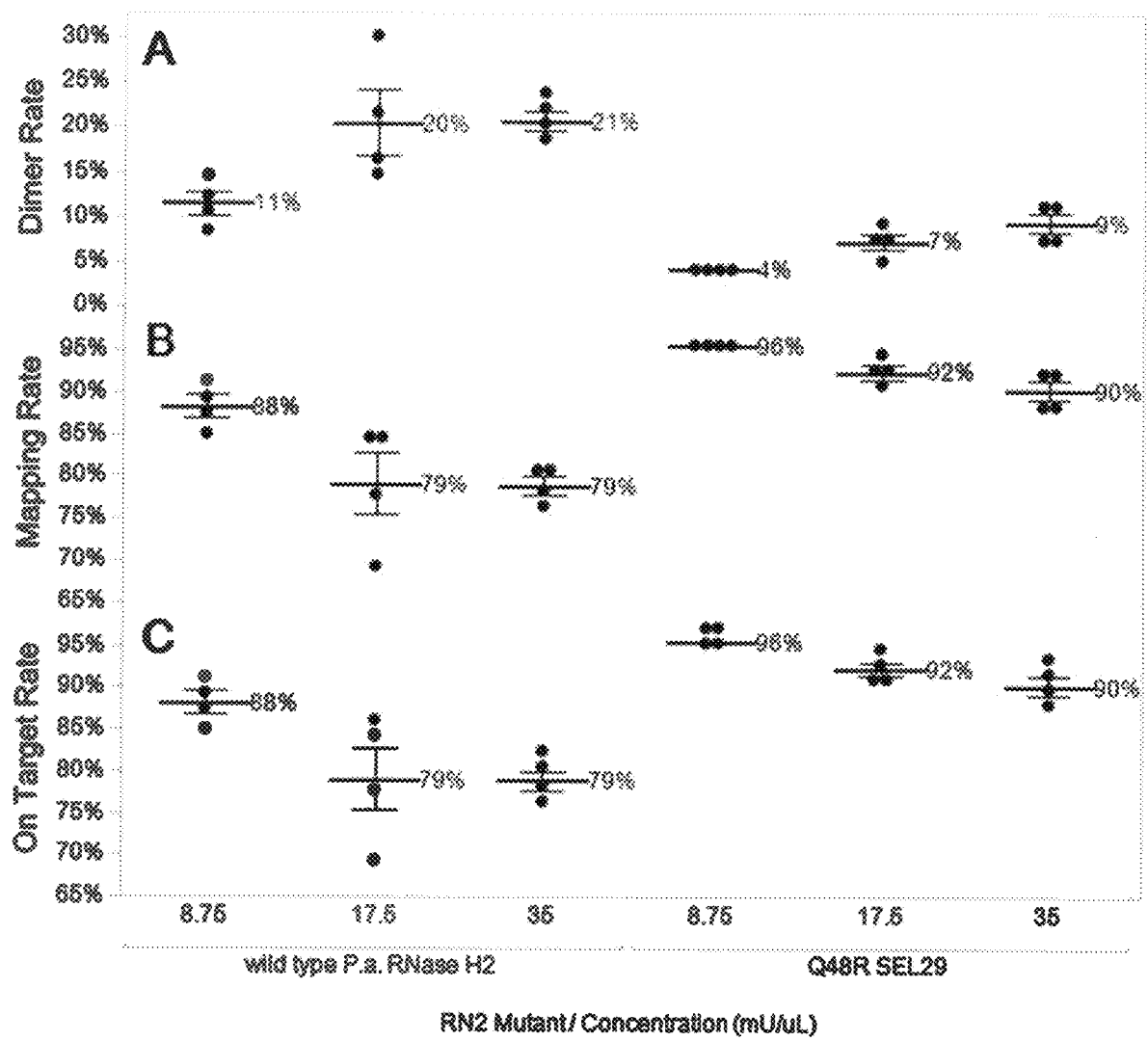
FIG. 1 depicts an exemplary plot showing that the dimer rate is lowered at all enzyme concentrations using the mutant Q48R SEL29 RNase H2 enzyme compared to the wild type P.a. RNase H2 enzyme (panel A); exemplary data that the mapping rate is higher at all RNase H2 enzyme concentrations with the mutant Q48R SEL29 RNase H2 enzyme compared to the wild type P.a. RNase H2 enzyme (panel B); exemplary data showing that the on target rate is higher at all enzyme concentrations with the mutant Q48R SEL29 RNase H2 enzyme compared to wild type P.a. RNase H2 enzyme (panel C).

The current invention provides novel hybrid RNase H2 enzyme variants that enhance enzymatic activity during rhPCR using certain DNA polymerase buffers while retaining their ability to retain or enhance the mismatch discrimination in a duplex template. The RNase H2 enzyme hybrids combine fragments of amino acid sequences from *Pyrococcus abyssi* (P.a.), *Thermococcus kodakarensis* (T.kod), and *Pyrococcus furiosus* organisms. The resultant hybrid RNase H2 enzymes, as well as select mutants based upon these enzymes, enhance mismatch discrimination significantly. In particular, the Q48R SEL29 RNase H2 (SEQ ID NO.:18) is shown to produce product mixtures having a reduced population of primer dimer species relative to a product mixture produced with a wild-type P.a. RNase H2 (SEQ ID NO.:1) in methods of conducting primer extension, performing rhPCR, amplifying a target DNA sequence, performing massively parallel sequencing, detecting a SNP-containing nucleic acid template from an amplicon library of nucleic acid templates, and performing a loop-mediated amplification reaction, among others.

Definitions

To aid in understanding the invention, several terms are defined below.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature. Primer extension can also be carried out in the absence of one or more of the nucleotide triphosphates in which case an extension product of limited length is produced. As used herein, the term "primer" is intended to encompass the oligonucleotides used in ligation-mediated reactions, in which one oligonucleotide is "extended" by ligation to a second oligonucleotide that hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product. The region of the primer that is sufficiently complementary to the template to hybridize is referred to herein as the hybridizing region.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two step cycles have a high temperature denaturation step followed by a hybridization/elongation (or ligation) step. Three step cycles comprise a denaturation step followed by a hybridization step followed by a separate elongation or ligation step.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Thermoccus/Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

The term "non-specific amplification," as used herein, refers to the amplification of nucleic acid sequences other than the target sequence that results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions, or in situations where there is a variant allele in the sample having a very closely related sequence to the true target as in the case of a single nucleotide polymorphism (SNP).

The term "3'-mismatch discrimination" refers to a property of a DNA polymerase to distinguish a fully complementary sequence from a mismatch-containing (nearly complementary) sequence where the nucleic acid to be extended (for example, a primer or other oligonucleotide) has a mismatch at the 3' end of the nucleic acid compared to the template to which the nucleic acid hybridizes. In some embodiments, the nucleic acid to be extended comprises a mismatch at the 3' end relative to the fully complementary sequence.

The term "3'-mismatch discrimination assay" refers to an assay to discern the present of improved specificity in amplification of a target DNA sequence when the target DNA sequence is interrogated with two primers having substantially identical sequence except for the occurrence of one of more nucleotide residue having different base composition at or near their respective 3'-ends. For example, a first primer having 3'-end sequences with perfect complementarity to the target DNA sequence is considered a 3'-matched primer and a second primer having a 3'-end sequences having at least one nucleotide base non-complementarity to the target DNA sequence is considered a 3'-mismatched primer. An example of a 3'-mismatch discrimination assay is provided in many of the examples, such as EXAMPLE 4 Tables 10 and 11, among others.

The term "primer dimer," as used herein, refers to a template-independent non-specific amplification product, which is believed to result from primer extensions wherein another primer serves as a template. Although primer dimers frequently appear to be a concatamer of two primers, i.e., a dimer, concatamers of more than two primers also occur.

The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components that includes the blocked primers of the invention.

For the purposes of this invention, the terms "non-activated" or "inactivated," as used herein, refer to a primer or other oligonucleotide that is incapable of participating in a primer extension reaction or a ligation reaction because either DNA polymerase or DNA ligase cannot interact with the oligonucleotide for their intended purposes. In some embodiments when the oligonucleotide is a primer, the non-activated state occurs because the primer is blocked at or near the 3'-end so as to prevent primer extension. When specific groups are bound at or near the 3'-end of the primer, DNA polymerase cannot bind to the primer and extension cannot occur. A non-activated primer is, however, capable of hybridizing to a substantially complementary nucleotide sequence.

For the purposes of this invention, the term "activated," as used herein, refers to a primer or other oligonucleotide that is capable of participating in a reaction with DNA polymerase or DNA ligase. A primer or other oligonucleotide becomes activated after it hybridizes to a substantially complementary nucleic acid sequence and is cleaved to generate a functional 3'- or 5'-end so that it can interact with a DNA polymerase or a DNA ligase. For example, when the oligonucleotide is a primer, and the primer is hybridized to a template, a 3'-blocking group can be removed from the primer by, for example, a cleaving enzyme such that DNA polymerase can bind to the 3' end of the primer and promote primer extension.

The term "cleavage domain" or "cleaving domain," as used herein, are synonymous and refer to a region located between the 5' and 3' end of a primer or other oligonucleotide that is recognized by a cleavage compound, for example a cleavage enzyme, that will cleave the primer or other oligonucleotide. For the purposes of this invention, the cleavage domain is designed such that the primer or other oligonucleotide is cleaved only when it is hybridized to a complementary nucleic acid sequence, but will not be cleaved when it is single-stranded. The cleavage domain or sequences flanking it may include a moiety that a) prevents or inhibits the extension or ligation of a primer or other oligonucleotide by a polymerase or a ligase, b) enhances discrimination to detect variant alleles, or c) suppresses undesired cleavage reactions. One or more such moieties may be included in the cleavage domain or the sequences flanking it.

The term "RNase H cleavage domain," as used herein, is a type of cleavage domain that contains one or more ribonucleic acid residue or an alternative analog that provides a substrate for an RNase H. An RNase H cleavage domain can be located anywhere within a primer or oligonucleotide, and is preferably located at or near the 3'-end or the 5'-end of the molecule.

An "RNase H2 cleavage domain" may contain one RNA residue, a sequence of contiguously linked RNA residues or RNA residues separated by DNA residues or other chemical groups. In one embodiment, the RNase H2 cleavage domain is a 2'-fluoronucleoside residue. In a more preferred embodiment, the RNase H2 cleavable domain includes two adjacent 2'-fluoro residues.

The term "blocked primer," as used herein, refers to a primer which possesses, at minimum, a cleaving domain suitable for hybridizing sufficiently to a target sequence, a cleavable domain, and a blocking group preventing extension from the 3' end of the primer until cleavage occurs. In the preferred embodiment, the cleavable domain is an RNase H cleavage domain, and the blocking group is a propanediol (C3) spacer.

The terms "cleavage compound," or "cleaving agent" as used herein, refers to any compound that can recognize a cleavage domain within a primer or other oligonucleotide, and selectively cleave the oligonucleotide based on the presence of the cleavage domain. The cleavage compounds utilized in the invention selectively cleave the primer or other oligonucleotide comprising the cleavage domain only when it is hybridized to a substantially complementary nucleic acid sequence, but will not cleave the primer or other oligonucleotide when it is single stranded. The cleavage compound cleaves the primer or other oligonucleotide within or adjacent to the cleavage domain. The term "adjacent," as used herein, means that the cleavage compound cleaves the primer or other oligonucleotide at either the 5'-end or the 3' end of the cleavage domain. Cleavage reactions preferred in the invention yield a 5'-phosphate group and a 3'-OH group.

In a preferred embodiment, the cleavage compound is a "cleaving enzyme." A cleaving enzyme is a protein or a ribozyme that is capable of recognizing the cleaving domain when a primer or other nucleotide is hybridized to a substantially complementary nucleic acid sequence, but that will not cleave the complementary nucleic acid sequence (i.e., it provides a single strand break in the duplex). The cleaving enzyme will also not cleave the primer or other oligonucleotide comprising the cleavage domain when it is single stranded. Examples of cleaving enzymes are RNase H enzymes and other nicking enzymes.

The term "nicking," as used herein, refers to the cleavage of only one strand of the double-stranded portion of a fully or partially double-stranded nucleic acid. The position where the nucleic acid is nicked is referred to as the "nicking site" (NS). A "nicking agent" (NA) is an agent that nicks a partially or fully double-stranded nucleic acid. It may be an enzyme or any other chemical compound or composition. In certain embodiments, a nicking agent may recognize a particular nucleotide sequence of a fully or partially double-stranded nucleic acid and cleave only one strand of the fully or partially double-stranded nucleic acid at a specific position (i.e., the NS) relative to the location of the recognition sequence. Such nicking agents (referred to as "sequence specific nicking agents") include, but are not limited to, nicking endonucleases (e.g., N.BstNB).

A "nicking endonuclease" (NE), as used herein, thus refers to an endonuclease that recognizes a nucleotide sequence of a completely or partially double-stranded nucleic acid molecule and cleaves only one strand of the nucleic acid molecule at a specific location relative to the recognition sequence. In such a case the entire sequence from the recognition site to the point of cleavage constitutes the "cleavage domain".

The term "blocking group," as used herein, refers to a chemical moiety that is bound to the primer or other oligonucleotide such that an amplification reaction does not occur. For example, primer extension and/or DNA ligation does not occur. Once the blocking group is removed from the primer or other oligonucleotide, the oligonucleotide is capable of participating in the assay for which it was designed (PCR, ligation, sequencing, etc.). Thus, the "blocking group" can be any chemical moiety that inhibits recognition by a polymerase or DNA ligase. The blocking group may be incorporated into the cleavage domain but is generally located on either the 5'- or 3'-side of the cleavage domain. The blocking group can be comprised of more than one chemical moiety. In the present invention the "blocking group" is typically removed after hybridization of the oligonucleotide to its target sequence.

The term "fluorescent generation probe" refers either to a) an oligonucleotide having an attached fluorophore and quencher, and optionally a minor groove binder or to b) a DNA binding reagent such as SYBR® Green dye.

The terms "fluorescent label" or "fluorophore" refers to compounds with a fluorescent emission maximum between about 350 and 900 nm. A wide variety of fluorophores can be used, including but not limited to: 5-FAM (also called 5-carboxyfluorescein; also called Spiro(isobenzofuran-1 (3H), 9'-(9H)xanthene)-5-carboxylic acid,3',6'-dihydroxy-3-oxo-6-carboxyfluorescein); 5-Hexachloro-Fluorescein; ([4, 7,2',4',5',7'-hexachloro-(3',6'-dipivaloyl-fluoresceinyl)-6-carboxylic acid]); 6-Hexachloro-Fluorescein; ([4,7,2',4',5', 7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloyfluoresceinyl)-5-carboxylic acid]); 6-Tetra-chloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl) amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indodicarbocyanine-3); and BODIPY FL (2,6-dibromo-4,4-difluoro-5,7-dimethyl-4-bora-3a,4a-diaza-s-indacene-3-proprionic acid); Quasar®-670 dye (Biosearch Technologies); Cal Fluor® Orange dye (Biosearch Technologies); Rox dyes; Max dyes (Integrated DNA Technologies), as well as suitable derivatives thereof.

As used herein, the term "quencher" refers to a molecule or part of a compound, which is capable of reducing the emission from a fluorescent donor when attached to or in proximity to the donor. Quenching may occur by any of several mechanisms including fluorescence resonance energy transfer, photo-induced electron transfer, paramagnetic enhancement of intersystem crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more. A number of commercially available quenchers are known in the art, and include but are not limited to DABCYL, Black Hole™ Quenchers (BHQ-1, BHQ-2, and BHQ-3), Iowa Black® FQ and Iowa Black® RQ. These are so-called dark quenchers. They have no native fluorescence, virtually eliminating background problems seen with other quenchers such as TAMRA that is intrinsically fluorescent.

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3' hydroxyl group of one polynucleotide to the 5' phosphate group of a second polynucleotide. Examples of ligases include E. coli DNA ligase, T4 DNA ligase, etc.

The ligation reaction can be employed in DNA amplification methods such as the "ligase chain reaction" (LCR), also referred to as the "ligase amplification reaction" (LAR), see Barany, Proc. Natl. Acad. Sci., 88:189 (1991); and Wu and Wallace, Genomics 4:560 (1989) incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. In the presence of the target sequence, DNA ligase will covalently link each set of hybridized molecules. Importantly, in LCR, two oligonucleotides are ligated together only when they base-pair with sequences without gaps. Repeated cycles of denaturation, hybridization and ligation amplify a short segment of DNA. A mismatch at the junction between adjacent oligonucleotides inhibits ligation. As in other oligonucleotide ligation assays this property allows LCR to be used to distinguish between variant alleles such as SNPs. LCR has also been used in combination with PCR to achieve enhanced detection of single-base changes, see Segev, PCT Public. No. WO9001069 (1990).

The term "codon-optimized" as that term modifies a particular nucleic acid encoding a polypeptide refers to inclusion of preferred codons for efficient expression in a given host cell, such as a given microorganism (e.g., E. coli, S. cerevisae, among others) or a mammalian cells (e.g., human cells, such as HeLa, COS cells, among others). Such preferred codons are well known in the art based upon codon bias tables developed for a variety of organisms. The polynucleotides that encode polypeptides of the present invention include those having codon-optimized open reading frames for any known organism in which codon bias tables have been developed or for which such tables can be readily discerned from empirical determination.

The phrase "BaseX PCR amplification method" refers to a highly efficient nucleic acid amplification that allows for a greater than 2-fold increase of amplification product for each amplification cycle and therefore increased sensitivity and speed over conventional PCR. This method is disclosed in United States Patent Publication U.S. Ser. No. 10/273,534 (B2), entitled "Exponential base-greater-than-2 nucleic acid amplification" to R. Higuchi (Applicant: Cepheid), which issued Apr. 30, 2019, the contents of which is herein incorporated by reference in its entirety.

The phrases "fusion protein" or "fusion polypeptide" refers to the inclusion of extra amino acid information that is not native to the protein to which the extra amino acid information is covalently attached. Such extra amino acid information may include tags that enable purification or identification of the fusion protein. Such extra amino acid information may include peptides that enable the fusion proteins to be transported into cells and/or transported to specific locations within cells. Examples of tags for these purposes include the following: AviTag, which is a peptide allowing biotinylation by the enzyme BirA so the protein can be isolated by streptavidin; Calmodulin-tag, which is a peptide bound by the protein calmodulin; polyglutamate tag, which is a peptide binding efficiently to anion-exchange resin such as Mono-Q; E-tag, which is a peptide recognized by an antibody; FLAG-tag, which is a peptide recognized by an antibody; HA-tag, which is a peptide from hemagglutinin recognized by an antibody; His-tag, which is typically 5-10 histidines bound by a nickel or cobalt chelate; Myc-tag, which is a peptide derived from c-myc recognized by an antibody; NE-tag, which is a novel 18-amino-acid synthetic peptide recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, which is a peptide derived from Ribonuclease A; SBP-tag, which is a peptide which binds to streptavidin; Softag 1, which is intended for mammalian expression; Softag 3, which is intended for prokaryotic expression; Strep-tag, which is a peptide which binds to streptavidin or the modified streptavidin called streptactin (Strep-tag II); TC tag, which is a tetracysteine tag that is recognized by FlAsH and ReAsH biarsenical compounds; V5 tag, which is a peptide recognized by an antibody; VSV-tag, a peptide recognized by an antibody; Xpress tag; Isopeptag, which is a peptide which binds covalently to pilin-C protein; SpyTag, which is a peptide which binds covalently to SpyCatcher protein; SnoopTag, a peptide which binds covalently to SnoopCatcher protein; BCCP (Biotin Carboxyl Carrier Protein), which is a protein domain biotinylated by BirA to enable recognition by streptavidin; Glutathione-S-transferase-tag, which is a protein that binds to immobilized glutathione; Green fluorescent protein-tag, which is a protein which is spontaneously fluorescent and can be bound by antibodies; HaloTag, which is a mutated bacterial haloalkane dehalogenase that covalently attaches to a reactive haloalkane substrate to allow attachment to a wide variety of substrates; Maltose binding protein-tag, a protein which binds to amylose agarose; Nus-tag; Thioredoxin-tag; and Fc-tag, derived from immunoglobulin Fc domain, which allows dimerization and solubilization and can be used for purification on Protein-A Sepharose. Nuclear localization signals (NLS), such as those obtained from SV40, allow for proteins to be transported to the nucleus immediately upon entering the cell. Given that the native Cas9 protein is bacterial in origin and therefore does not naturally comprise a NLS motif, addition of one or more NLS motifs to the recombinant Cas9 protein is expected to show improved genome editing activity when used in eukaryotic cells where the target genomic DNA substrate resides in the nucleus. One skilled in the art would appreciate these various fusion tag technologies, the particular amino acid sequences involved, as well as how to make and use fusion proteins that include them. In one embodiment, highly preferred fusion proteins or fusion polypeptides include a His-tag motif, though one skilled in the art will appreciate that other tags can be included, as noted above. The present invention includes fusion proteins or fusion polypeptides as well as versions of the original mutated versions of the corresponding protein or polypeptide lacking additional amino acid sequence information.

Novel Hybrid RNase 112 Enzyme Variants Generated by Recombination Reshuffling of Amino Acid Sequences from Known RNase 112 Enzymes.

Two hybrid RNase H2 enzymes with novel and useful properties were generated via partial recombination ("shuffling") of amino acid sequences from three RNase H2 enzymes, including Pyrococcus abyssi, Thermococcus kodakarensis, and Pyrococcus furiosus. and can result in hybrid RNase H2 enzymes. In particular, two mutant RNase H2 enzymes, SEL28 RNase H2 (SEQ ID NO.: 89) and SEL29 RNase H2 (SEQ ID NO.: 90) that combine fragments of amino acid sequences from Pyrococcus abyssi, Thermococcus kodakarensis, and Pyrococcus furiosus organisms have been discovered to enhance mismatch discrimination significantly. The mutants were selected from a library created by random shuffling of RNase H2 sequences. Both mutant enzymes contain fragments of amino acid residues from T. kod RNase H2, although other changes are also present. Based on structural homologies to known crystal structures (Muroya et al., 2001; Rychlik et al., 2010), these residues likely make contacts with the bound DNA duplex. Without being bound to any particular theory, it can be hypothesized that amino acid residues from T.kod RNase H2 will change the enzyme binding pocket for substrate duplex resulting in changes of the binding affinity and catalysis of nucleic acid cleavage. The amino acid sequences of the wild-type P. ab. RNase H2 protein (SEQ ID NO.: 88), hybrid SEL28 RNase H2 protein (SEQ ID NO.: 89) and hybrid SEL29 RNase H2 protein (SEQ ID NO.: 90) are depicted in Table 1. The corresponding (His)$_6$-tagged amino acid sequences of the wild-type P. ab. RNase H2 protein (SEQ ID NO.: 1), hybrid SEL28 RNase H2 protein (SEQ ID NO.: 2) and hybrid SEL29 RNase H2 protein (SEQ ID NO.: 3) were prepared as well and served as the basis for generating additional mutant RNase H2 proteins (see Table 3).

TABLE 1

Amino acid sequences for the hybrid RNase 112 proteins.

| SEQ ID NO.: | Protein Description | Sequence[1] |
|---|---|---|
| 88 | WT P. ab. RNase H2 | MKVAGADEAGRGPVI GPLVIVAAVVEEDKI RSLTKLGVKDSKQLT PAQREKLFDEIVKVL DDYSVVIVSPQDIDG RKGSMNELEVENFVK ALNSLKVKPEVIYID SADVKAERFAENIRS RLAYEAKVVAEHKAD AKYEIVSAASILAKV IRDREIEKLKAEYGD FGSGYPSDPRTKKWL EEWYSKHGNFPPIVR RTWDTAKKIEEKFKR AQLTLDNFLKRFRN |
| 89 | SEL28 RNase H2 | MKVAGADEAGRGPVI GPLVIVAAVVDENSL PKLEELKVRDSKKLT PKRREKLFDEIVKVL DDYSVVIVSPQDIDG RKGSMNELEVENFVK ALNSLKVKPDVIYAD AADVDEERFARELGE RLNFEAEVVAKHKAD DIFPVVSAASILAKV IRDREIEKLKAEYGD FGSGYPSDPRTKKWL EEWYSKHGNFPPIVR RTWDTAKKIEEKFKR AQLTLD<u>KFFKP</u> |
| 90 | SEL29 RNase H2 | MKVAGIDEAGRGPAI GPLVI<u>V</u>AAVVDENSL PKLEELKVRDSKKLT PAQREKLFDEIVKVL DDYSVVIVSPQDIDG RKGSMNELEVENFVK ALNSLKVKPDVIYAD AADVDEERFARELGE RLNFEAKVVAEHKAD AKYEIVSAASILAKV IRDREIEKLKAEYGD FGSGYPSDPRTRAFL ENYYREHGEFPPIVR KGWKTLKKIAEKVES EKKAEERQATLDRYF RKV |

[1]Amino acids identical to wild-type Pyrococcus abyssi RNase H2 are shown as non-underlined, non-bold sequence. Amino acids that appear to originate from Thermococcus kodakarensis and Pyrococcus furiosus RNase H2 sequences are shown in bold and underlined respectively.

The resultant hybrid SEL28 and SEL29 RNase H2 enzymes encoded by SEQ ID NOs.: 89 and 90 improve mismatch discrimination when the mismatch is located at RNA nucleotide, but to various degrees and with different specificities. (Data not shown). Likewise, the SEL28 and SEL29 mutant RNase H2 enzymes encoded by SEQ ID NOs.: 89 and 90 improve mismatch discrimination 5' of the RNA nucleotide. (Data not shown.)

rhPCR could also be performed using a high-fidelity DNA polymerase—such as the DNA polymerase from Pyrococcus furiosus and Thermococcus kodakarensis (KOD)—instead of the DNA polymerase from Thermus aquaticus (Taq). However, WT P.a. RNase H2, SEL28 RNase H2, and SEL29 RNase H2 have limited activity in rhPCR using high-fidelity polymerase and the associated reaction buffer. The optimal reaction buffer for Taq DNA polymerase differs substantially from the optimal buffer for KOD DNA polymerase. Mutations in RNase H2 could be found that have greater tolerance for components in the reaction buffer for KOD DNA polymerase. We show that Q48R, A107V, and P13S/A107V when added to hybrid mutant SEL28 or SEL29 RNase H2 enhances enzymatic activity using KOD DNA polymerase reaction buffer.

The present invention relates to mutant RNase H2 enzymes that enhance enzymatic activity during rhPCR using KOD DNA polymerase and its optimal reaction buffer. Mutations in the 48th and 107' amino acid of SEL29 RNase H2 have been shown to have this improved activity. A screen of seven point mutants with a background of either SEL28 RNase H2 or SEL29 RNase H2 were performed, and Q48R SEL29 RNase H2 and A107V SEL29 RNase H2 were shown to enhance enzymatic activity using KOD DNA polymerase reaction buffer. These also were shown to retain or enhance the mismatch discrimination capabilities of the SEL29 RNase H2.

RNase H2-Mediated PCR

The hybrid RNase H2 mutant proteins disclosed herein can be used in a variety of PCR applications. RNase H2-dependent PCR is a method for increasing PCR specificity and eliminating primer-dimers by using RNase H2 from *Pyrococcus abyssi* or related organisms and DNA primers that contain a single ribonucleotide residue and a 3' blocking moiety ("blocked-cleavable primers"). The blocked-cleavable primers are activated when cleaved by the RNase H2 enzyme. Cleavage occurs on the 5' side of the RNA base after primer hybridization to the target DNA. Because the primers can only be cleaved after they hybridize to the perfectly matched target sequence, primer-dimers are reduced. The requirement for high target complementarity reduces amplification of closely related sequences.

In this regard, the hybrid RNase H2 mutant proteins are particularly amendable to enhancing performance in generating high quality genomic amplicon libraries for high throughput multiplex sequencing applications, such as next-generation sequencing applications (NGS). In particular, Q48R SEL29 is a useful RNase H2 enzyme for RNase H2-mediated PCR applications and systems, such as Applicant's rhAmpSeg™ system.

RNase H2-Mediated SNP Detection and Rare Allele Detection

Owing to their enhanced 3'-mismatch discrimination attributes, the hybrid RNase H2 mutant proteins disclosed herein can be used to detect single nucleotide polymorphism detection and rare allele detection. The use of block-cleavable primers that only form perfect duplexes with the desired SNP-containing nucleic acid templates will be recognized and cleaved by the hybrid RNase H2 mutant proteins, thereby activating the primer:desired nucleic acid template duplexes for primer extension by a DNA polymerase under suitable conditions.

RNase H2 in Loop-Meditated Isothermal Amplification (LAMP)

Use of RNase H2 in Loop-meditated isothermal amplification (LAMP) is also contemplated herein. The LAMP method of amplification is performed under isothermal conditions, that is, without changes in reaction temperature during cycling. LAMP requires a minimum of four different primers designed to recognize six different regions of the desired amplicon (Notomi, et al. *Nucleic Acids Research*, 28(12) (2000)). The amplification reaction depends on the strand displacement activity of the DNA polymerase, usually from *Bacillus stearothermophilus* (Bst). The products have a structure that consists of a long chain of inverted repeats of the target sequence.

LAMP reactions are prone to formation of primer-dimer products, owing to the large number of primers and the use of the mesophilic DNA polymerase in the method. LAMP also lacks a 5'→3' exonuclease activity in the amplifying BST polymerase, due to the fact that this activity would destroy the amplification by competing with the essential strand-displacement activity. The use of blocked-cleavable primers and RNase H2 can be employed to reduce or eliminate the detection of primer-dimer signal in LAMP reactions. In this regard, the hybrid RNase H2 mutant proteins are particularly amendable to enhancing performance of desired products formed in LAMP reactions without attendant production of primer-dimers.

Applications

In a first aspect, a hybrid RNase H2 protein is provided. The hybrid RNase H2 protein includes fragments of amino acid sequences from *Pyrococcus abyssi* (P.a.), *Thermococcus kodakarensis* (T.kod), and *Pyrococcus furiosus* organisms. In a first respect, the hybrid RNase H2 protein is selected from SEQ ID NOs.: 2 and 3. In a second respect, the hybrid RNase H2 protein is selected from SEQ ID NOs.: 14-20.

In a second aspect, a recombinant nucleic acid encoding any of the hybrid RNase H2 proteins disclosed herein is provided. In a first respect, exemplary recombinant nucleic acids encoding any of the hybrid RNase H2 protein include SEQ ID NOs.:79-87 of Table 14.

In a third aspect, a method for conducting primer extension is provided. The method includes the step of contacting a hybrid RNase H2 protein as disclosed herein with a primer, a polynucleotide template, nucleoside triphosphates and a DNA polymerase under conditions suitable for a primer extension method, thereby producing an extended primer. In a first respect, the DNA polymerase includes a high-fidelity archaeal DNA polymerase. In a second respect, the primer includes a blocked-cleavable primer. In a third respect, the primer extension method includes a method for conducting polymerase chain reaction (PCR). In a fourth respect, the method for conducting PCR improves mismatch discrimination in a primer:polynucleotide hybrid formed between the primer and the polynucleotide template. In a fifth respect, the improvement in mismatch discrimination includes an improvement in 3'-mismatch discrimination.

In a fourth aspect, a reaction mixture is provided. The reaction mixture includes a hybrid RNase H2 protein as described herein, at least one primer, a polynucleotide template, nucleoside triphosphates and a DNA polymerase. In a first respect, the reaction mixture includes the DNA polymerase being a high-fidelity archaeal DNA polymerase. In a second respect, the reaction mixture includes the at least one primer being a blocked-cleavable primer.

In a fifth aspect, a method for performing rhPCR is provided. The method includes the step of performing primer extension with a hybrid RNase H2 as described herein, a DNA polymerase, and a primer. In a first respect, the method of performing rhPCR includes performing primer extension with a high-fidelity archaeal DNA polymerase. In a second respect, the hybrid RNase H2 enzyme is reversibly inactivated either by chemical modification, aptamer or by a blocking antibody. In a third respect, a blocking group is attached to the 3'-terminal nucleotide of the primer. In a fourth respect, the blocking group is attached 5' of the 3'-terminal residue and inhibits the primer from serving as a template for DNA synthesis. In a fifth respect, the blocking group includes one or more abasic residues. In a sixth respect, the one or more abasic residues is a C3 spacer. In a seventh respect, the blocking group includes one member selected from the group consisting of RDDDDx, RDDDDMx, RDxxD, RDxxDM, RDDDDxxD, RDDDDxxDM and DxxD, wherein R is an RNA residue, D is a DNA residue, M is a mismatched residue and x is a C3 spacer or other proprietary group resistant to degradation. In this regard, the blocking group includes a label permitting detection of an extension amplification reaction. In this regard, a label permitting detection of the amplification reaction is attached to the oligonucleotide primer 3' from the cleavage site. In this regard, the label is a fluorophor or a mass tag for detection of the amplification reaction by mass spectrometry. In a further aspect, the cleavage domain of the block-cleavable primer includes one or more of the following moieties: a DNA residue, an abasic residue, a modified nucleoside, or a modified phosphate internucleotide linkage. In additional respect, the cleavage domain includes a single RNA residue, two adjacent RNA residues, a continuous sequence of three or more RNA residues, lacks an RNA residue or one or more 2'-modified nucleosides. In those respects, in which the cleavage domain includes one or more 2'-modified nucleosides, the one or more 2'-modified nucleosides is selected from the group consisting of 2'-O-alkyl RNA nucleoside, 2'-fluoronucleoside, locked nucleic acid, 2'-ethylene nucleic acid residue, 2'-alkyl nucleoside, 2'-aminonucleoside and 2'-thionucleoside. Exemplary 2'-modified nucleosides include 2'-O-methyl RNA nucleosides and 2'-fluoronucleosides.

In a sixth aspect, a method of amplifying a target DNA sequence is provided. The method includes several steps. The first step is providing a reaction mixture that includes the following: (i) an oligonucleotide primer having a cleavage domain, which is cleavable by an RNase H2 enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis; (ii) a sample nucleic acid that may or may not the target sequence; (iii) a DNA polymerase, and (iv) a hybrid RNase H2 protein as disclosed herein. The second step is hybridizing the oligonucleotide primer to the target DNA sequence to form a double-stranded substrate. The third step is cleaving the hybridized oligonucleotide primer with said hybrid RNase H2 enzyme at a cleavage site within or adjacent to the cleavage domain to remove the blocking group from the oligonucleotide primer. In a first respect of the method, the DNA polymerase is an archaeal high-fidelity DNA polymerase. In a second respect, the RNase H2 protein is reversibly inactivated either by chemical modification or by a blocking antibody. In additional respects of the method, the blocking group is attached to the 3'-terminal nucleotide of the oligonucleotide primer. In additional respects of the method, the blocking group is attached 5' of the 3'-terminal residue and inhibits the oligonucleotide primer from serving as a template for DNA synthesis. In additional respects of the method, the blocking group includes one or more abasic residues. In additional respects of the method, the one or more abasic residues is a C3 spacer or other proprietary group resistant to degradation. In additional respects of the method, the blocking group comprises one member selected from the group consisting of RDDDDx, RDDDDMx, RDxxD, RDxxDM, RDDDDxxD, RDDDDxxDM and DxxD, wherein R is an RNA residue, D is a DNA residue, M is a mismatched residue and x is a C3 spacer or other proprietary group resistant to degradation. In additional respects of the method, the blocking group includes a label permitting detection of the extension amplification reaction. In additional respects of the method, the method further includes a label permitting detection of the amplification reaction, wherein the label is attached to the oligonucleotide primer 3' from the cleavage site. In these respects, the label is a fluorophore or a mass tag for detection of the amplification reaction by mass spectrometry. In additional respects of the method, the cleavage domain includes one or more of the following moieties: a DNA residue, an abasic residue, a modified nucleoside, or a modified phosphate internucleotide linkage. In additional respects of the method, the cleavage domain includes a single RNA residue, two adjacent RNA residues, a continuous sequence of three or more RNA residues, or one or more 2'-modified nucleosides. In the respects in which the method the cleavage domain includes one or more 2'-modified nucleosides, those 2'-modified nucleosides are selected from the group consisting of 2'-O-alkyl RNA nucleoside, 2'-fluoronucleoside, locked nucleic acid, 2'-ethylene nucleic acid residue, 2'-alkyl nucleoside, 2'-aminonucleoside and 2'-thionucleoside. Exemplary 2'-modified nucleosides include 2'-O-methyl RNA nucleoside and 2'-fluoronucleoside.

In a seventh aspect, a kit for producing an extended primer is provided. The kit includes at least one container providing a hybrid RNase H2 protein as disclosed herein. In a first respect, the kit further includes one or more additional containers selected from the group consisting of: (a) a container providing a primer hybridizable, under primer extension conditions, to a predetermined polynucleotide template; (b) a container providing nucleoside triphosphates; (c) a container providing a buffer suitable for primer extension and (d) a DNA polymerase. In a second respect, the DNA polymerase includes a high-fidelity archaeal DNA polymerase. In a third respect, the aforementioned kits include one or more additional containers containing a blocked-cleavable primer.

In an eighth aspect, a kit for performing amplification of a target DNA sequence is provided. The kit includes a reaction buffer that includes an RNase H2 as described herein and a high-fidelity archaeal DNA polymerase. In a first respect, the kit further includes one or more oligonucleotide primers, wherein at least one oligonucleotide primer has a cleavage domain, which is cleavable by an RNase H2 enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis. In a second respect, the kit includes the blocking group being one member selected from the group consisting of RDDDDx, RDDDDMx, RDxxD, RDxxDM, RDDDDxxD, RDDDDxxDM and DxxD, wherein R is an RNA residue, D is a DNA residue, M is a mismatched residue and x is a C3 spacer or other proprietary group resistant to degradation.

In a ninth aspect, a method of preparing an amplicon library of template nucleic acids is provided. The method includes several steps. The first step is forming a mixture that includes a population of nucleic acids, at least block-cleavable primer, a hybrid RNase H2 protein, dNTPs, a DNA polymerase and a buffer such that a hybrid duplexes form between the at least block-cleavable primer and the population of nucleic acids in the mixture. The second step is cleaving the at least one block-cleavable primer with the hybrid RNase H2 protein to generate at least one active primer capable of primer extension by the DNA polymerase. The third step is extending the at least one active primer with the DNA polymerase in the buffer under conditions that permit amplification of one or more template nucleic acids from the population of nucleic acids, thereby generating the amplicon of template nucleic acids. In a first respect, the hybrid RNase H2 protein is selected from Q48R SEL29 (SEQ ID NO.:18), or others. In a second respect, the DNA polymerase is a high-fidelity archaeal DNA polymerase or others. In a third respect, the buffer is a high-fidelity archaeal DNA polymerase buffer.

In a tenth aspect, a method of performing massively parallel sequencing is provided. The method includes several steps. The first step is preparing a library population of template nucleic acids using a population of nucleic acids, a hybrid RNase H2 mutant protein, at least one block-cleavable primer, a DNA polymerase, dNTPs and buffer in a PCR method. The second step is sequencing a plurality of desired template nucleic acids from the library population of template nucleic acids. In a first respect, the hybrid RNase H2 protein is selected from Q48R SEL29 (SEQ ID NO.:18), or others.

In an eleventh aspect, a method of detecting a SNP-containing nucleic acid template from an amplicon library of nucleic acid templates is provided. The method includes several steps. A first step includes forming a mixture that includes an amplicon library of nucleic acid templates; at least one blocked-cleavable primer; a hybrid mutant RNase H2 protein; dNTPs; a DNA polymerase; and a buffer. A hybrid duplex forms between the at least block-cleavable primer and the SNP-containing nucleic acid template in the amplicon library of nucleic acid templates in the mixture. The second step includes cleaving the at least one block-cleavable primer of the hybrid duplex with the hybrid RNase H2 protein to generate at least one active primer capable of primer extension of the hybrid duplex by the DNA polymerase. The third step includes extending the at least one active primer in the duplex with the DNA polymerase in the buffer under conditions that permit amplification of one or more template nucleic acids from the amplicon library of nucleic acid templates, thereby detecting the SNP-containing nucleic acid template. In a first respect, the method includes a hybrid mutant RNase H2 protein selected from Q48R SEL29 (SEQ ID NO.:18), or others. In a second respect, the method includes a buffer being a high-fidelity archaeal DNA polymerase buffer.

In a twelfth aspect, a method of performing a loop-mediated amplification reaction is provided. The method includes two steps. A first step includes forming a mixture that includes a nucleic acid template; four blocked-cleavable primers, wherein the blocked-cleavable primers form a duplex with the nucleic acid template that is a substrate for an RNase H2 protein; an RNase H2 protein, wherein the RNase H2 protein is selected from Q48R SEL29 (SEQ ID NO.:18) or others; a DNA polymerase protein; dNTPs; and a buffer. A second step includes performing isothermal amplification cycles with the mixture.

In a thirteenth aspect, a method of performing a rhPCR assay having reduced primer dimer formation is provided. The method includes performing primer extension with Q48R SEL29 RNase H2 (SEQ ID NO:18). The reduced primer dimer formation corresponds to a reduced amount of primer dimers formed during the rhPCR assay with Q48R SEL29 RNase H2 (SEQ ID NO:18) when compared to rhPCR assays conducted with wild-type P.a. RNase H2 (SEQ ID NO: 1).

In a fourteenth aspect, a method of performing a rhPCR assay having an improved mapping rate and on-target rate for desired products is provided. The method includes performing primer extension with Q48R SEL29 RNase H2 (SEQ ID NO:18). The improved mapping rate and on-target rate corresponds to an increased mapping and on-target amplification of desired products formed during the rhPCR assay with Q48R SEL29 RNase H2 (SEQ ID NO:18) when compared to rhPCR assays conducted with wild-type P.a. RNase H2 (SEQ ID NO: 1).

Finally, the RNase H2 polypeptides of the present invention are amenable for use in the BaseX PCR amplification method, a highly efficient amplification method disclosed in United States Patent Publication U.S. Ser. No. 10/273,534 (B2), the contents of which are herein incorporated by reference in its entirety.

EXAMPLES

The present invention is further illustrated by reference to the following Examples. However, it should be noted that these Examples, like the embodiments described above, are illustrative and are not to be construed as restricting the enabled scope of the invention in any way.

Example 1. Generation of SEL28 and SEL29 Hybrid RNase 112 Proteins Via Recombination Reshuffling Mutant RNase H2 proteins were synthesized using in vitro DNA recombination and directed molecular evolution techniques. Altravax™ Inc. (Sunnyvale, CA) generated a library of 5,500 mutants under the contract agreement with Integrated DNA Technologies. SEL28 and SEL29 mutants were selected in initial screening done in IDT where the mutants exhibited increased mismatch discrimination in an RNase H2 cleavage reaction. The mutants were created in pET-27b(+) plasmid vector inside of *Escherichia coli* (*E. coli*) BL21 (DE3). Expressed proteins based on T7 system contain a pelB signal sequence at the N-terminus, mutated RNase H2 genes, a human herpes simplex virus 2 epitope tag, and a six-histidine tag at the C-terminus. *E. coli* cells were grown in 12 mL of LB Broth with 50 µg/mL kanamycin (Teknova™, Hollister, CA) using 50 mL TPP TubeSpin® Bioreactors (Techno Plastic Products AG, Trasadingen, Switzerland). Expression of RNase H2 was induced using the Overnight Express™ Autoinduction System 1 (MilliporeSigma™, Burlington, MA) at 37° C. for 20 hours. Bacterial expression strains were grown while shaken at 250 rpm using a MaxQ™ 4000 orbital shaker (ThermoFisher Scientific™, Grand Island, NY). Cells were centrifuged at 7,500×g for 10 minutes in ThermoScientific Sorvall™ Legend XTR centrifuge and the supernatant was discarded. The cell paste was stored at −80° C. and resuspended in 0.6 mL of lysis solution consisting of the cell resuspension buffer containing 50 mMNaCl, 40 mM Tris-HCl pH 8.0, 2.5 mM MgCl$_2$, 0.5 mM CaCl$_2$, 1× BugBuster® Extraction Reagent (MilliporeSigma™, Burlington, MA), 1× cOmplete™, EDTA-free protease inhibitor cocktail (MilliporeSigma™, Burlington, MA), 0.1 mg/mL of lysozyme (~600 units, ThermoFisher™ Scientific, Grand Island, NY), and 4 U/mL of Ambion™ DNase I (ThermoFisher™ Scientific, Grand Island, NY). Lysis took 15 minutes at 25° C. while cells were shaken at 120 rpm. Insoluble materials were removed by centrifugation at 16,000×g for 20 minutes. DNase I and native *E. coli* proteins were denatured at 75° C. for 15 minutes. Insoluble denatured proteins were again removed by centrifugation at 16,000×g for 15 minutes. Capturem™ His-Tagged Miniprep Kit (Takara Bio™, Mountain View, CA) was used for protein purification. Binding columns from the kit were washed with the cell resuspension buffer and supernatants containing RNase H2 were loaded on the columns. Solutions were pulled through columns by centrifugation at 11,000×g for 1 minute. Columns were washed twice with 200 µL of wash buffer (20 mM Na$_3$PO$_4$, 150 mM NaCl, pH 7.6) with 20 mM imidazole added. RNase H2 enzymes were eluted with 200 µL of elution buffer (20 mM Na$_3$PO$_4$, 500 mM NaCl, 500 mM imidazole, pH 7.6) and dialyzed against 1 L of 2× storage buffer F (pH 8.4, 40 mM Tris-HCl, 0.2 mM EDTA, 200 mM KCl) overnight using D-Tube™ Dialyzer Midi, MWCO 6-8 kDa (MilliporeSigma™, Burlington, MA). Dialysis buffer in the tank was replaced at least once. Samples were recovered from dialysis and mixed in 1:1 volume ratio with mixture of 99.8% (v/v) glycerol and 0.2% (v/v) Triton X-100. These purified and concentrated RNase H2 solutions were stored at −20° C. Their purity was estimated by SDS gel electrophoresis using Any kD™ Mini-PROTEAN® TGX Stain-Free™

Protein Gels (Bio-Rad®, Hercules, CA). RNase H2 enzyme exhibited dominant protein band (>75%) in all purified samples and its position corresponded to expected molecular mass of 28.9 kg/mol compared to Precision Plus Protein™ Unstained Standards (Bio-Rad®, Hercules, CA).

The amino acid sequences of the mutant proteins are shown in Table 1, SEQ ID NOs.: 89 and 90. The sequencing was done using Applied Biosystems BigDye Terminators v3.1 kit. Plasmid DNA was isolated from bacterial strains with Wizard® Plus SV Minipreps DNA Purification System (Promega, Madison, WI) following the manufacturer's protocol. Sequencing data were collected by Applied Biosystems 3130 Genetic Analyzer.

Example 2. Q48R and A107V SDM Mutants in SEL29 RNase 112 Increase Enzymatic Activity in *Thermococcus kodakarensis* DNA Polymerase Reaction Buffer Compared to SEL29 RNase 112

(His)$_6$-tagged mutant SEL28 and SEL29 RNase H2 proteins were generated by site-directed mutagenesis (SDM) techniques (see, e.g., Weiner M. et al., *Gene*, 151:119-123 (1994)). Primers used for SDM of SEL28 and SEL29 RNase H2 are shown in Table 2, SEQ ID NOs.: 4-13. The mutants were sequence verified, and protein was expressed in *E. coli* using standard methods. Purification was done by affinity purification over a charged Ni$^{2+}$ column, as described earlier (Dobosy et al., 2011, and U.S. Pat. No. 8,911,948 B2). The amino acid sequences of the mutant proteins are shown in Table 3, SEQ ID NOs.:2-3, 14-20.

TABLE 2

SDIM primers for mutagenesis of the RNase H2 enzymes.

| Primer name | SEQ ID NO.: | Specific AA changes | Sequence[1] |
|---|---|---|---|
| P13S SEL28 Forward Oligo | 4 | P13S | GGTGCAGATGAAGCTGGTCG TGGTTCTGTTATTGGTCCGC TGGTTATTGTTGCT |
| P13S SEL28 Reverse Oligo | 5 | P13S | AGCAACAATAACCAGCGGAC CAATAACAGAACCACGACCA GCTTCATCTGCACC |
| A107V SEL28 Forward Oligo | 6 | A107V | AAGCCGGATGTTATTTACGC TGATGCCGTAGATGTTGATG AAGAACGTTTCGCTAGA |
| A107V SEL28 Reverse Oligo | 7 | A107V | TCTAGCGAAACGTTCTTCAT CAACATCTACGGCATCAGCG TAAATAACATCCGGCTT |
| P13S SEL29 Forward Oligo | 8 | P13S | GGTATAGATGAAGCTGGTCG TGGTTCTGCTATTGGTCCGC TGGTTATTGTTGGT |
| P13S SEL29 Reverse Oligo | 9 | P13S | AGCAACAATAACCAGCGGAC CAATAGCAGAACCACGACCA GCTTCATCTATACC |
| Q48R SEL29 Forward Oligo | 10 | Q48R | AGACTCCAAAAAGCTGACCC CGGCCCGCCCGTGAAAAACTG TTCGATGAAATCG |
| Q48R SEL29 Reverse Oligo | 11 | Q48R | CGATTTCATCGAACAGTTTT TCACGGCGCGCCGGGGTCAG CTTTTTGGAGTCT |

TABLE 2-continued

SDIM primers for mutagenesis of the RNase H2 enzymes.

| Primer name | SEQ ID NO.: | Specific AA changes | Sequence[1] |
|---|---|---|---|
| A107V SEL29 Forward Oligo | 12 | A107V | AAGCCGGATGTTATTTACGC TGATGCCGTAGATGTTGATG AAGAACGTTTCGCTAGA |
| A107V SEL29 Reverse Oligo | 13 | A107V | TCTAGCGAAACGTTCTTCAT CAACATCTACGGCATCAGCG TAAATAACATCCGGCTT |

[1]All bases are DNA. Characters shown in bold and underlined are the mutagenic nucleotides.

TABLE 3

Amino acid sequences for the RNase H2 proteins.

| Mut ID # | SEQ ID NO.: | Specific AA changes | Sequence[1] |
|---|---|---|---|
| N/A | 1 | WT *P.a.* RNase H2 | MKVAGADEAGRGPVIGPLVIVAAVVEEDK IRSLTKLGVKDSKQLTPAQREKLFDEIVKV LDDYSVVIVSPQDIDGRKGSMNELEVENFV KALNSLKVKPEVIYIDSADVKAERFAENIRS RLAYEAKVVAEHKADAKYEIVSAASILAK VIRDREIEKLKAEYGDFGSGYPSDPRTKKW LEEWYSKHGNFPPIVRRTWDTAKKIEEKFK RAQLTLDNFLKRFRN*KLAAALEIKRASQPEL APEDPEDVEHHHHHH* |
| 1 | 2 | SEL28 RNase H2 | MKVAGADEAGRGPVIGPLVIVAAVVDENS LPKLEELKVRDSKKLTPKRRREKLFDEIVKV LDDYSVVIVSPQDIDGRKGSMNELEVENFV KALNSLKVKPDVIYADAADVDEERFAREL GERLNFEAEVVAKHKADDIFPVVSAASILA KVIRDREIEKLKAEYGDFGSGYPSDPRTKK WLEEWYSKHGNFPPIVRRTWDTAKKIEEK FKRAQLTLDKFFKKP*KLAAALEIKRASQPEL APEDPEDVEHHHHHH* |
| 2 | 3 | SEL29 RNase H2 | MKVAGIDEAGRGPAIGPLVIVAAVVDENSL PKLEELKVRDSKKLTPAQREKLFDEIVKVL DDYSVVIVSPQDIDGRKGSMNELEVENFVK ALNSLKVKPDVIYADAADVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV*KLAAALEIKRASQ PELAPEDPEDVEHHHHHH* |
| 3 | 14 | P13S SEL28 RNase H2 | MKVAGADEAGRG<u>S</u>VIGPLVIVAAVVDENS LPKLEELKVRDSK̄K̄LTPKRRREKLFDEIVKV LDDYSVVIVSPQDIDGRKGSMNELEVENFV KALNSLKVKPDVIYADAADVDEERFAREL GERLNFEAEVVAKHKADDIFPVVSAASILA KVIRDREIEKLKAEYGDFGSGYPSDPRTKK WLEEWYSKHGNFPPIVRRTWDTAKKIEEK FKRAQLTLDKFFKKP*KLAAALEIKRASQPEL APEDPEDVEHHHHHH* |
| 4 | 15 | A107V SEL28 RNase H2 | MKVAGADEAGRGPVIGPLVIVAAVVDENS LPKLEELKVRDSKKLTPKRRREKLFDEIVKV LDDYSVVIVSPQDIDGRKGSMNELEVENFV KALNSLKVKPDVIYADAVDVDEERFAREL GERLNFEAEVVAKHKADD̄IFPVVSAASILA KVIRDREIEKLKAEYGDFGSGYPSDPRTKK WLEEWYSKHGNFPPIVRRTWDTAKKIEEK FKRAQLTLDKFFKKP*KLAAALEIKRASQPEL APEDPEDVEHHHHHH* |

TABLE 3-continued

Amino acid sequences for the RNase H2 proteins.

| Mut ID # | SEQ ID NO.: | Specific AA changes | Sequence[1] |
|---|---|---|---|
| 5 | 16 | P13S/A107V SEL28 RNase H2 | MKVAGADEAGRGS̲VIGPLVIVAAVVDENS LPKLEELKVRDSK̲KLTPKRREKLFDEIVKV LDDYSVVIVSPQDIDGRKGSMNELEVENFV KALNSLKVKPDVIYADAV̲DVDEERFAREL GERLNFEAEVVAKHKADD̲IFPVVSAASILA KVIRDREIEKLKAEYGDFGSGYPSDPRTKK WLEEWYSKHGNFPPIVRRTWDTAKKIEEK FKRAQLTLDKFFKKP*KLAAALEIKRASQPEL APEDPEDVEHHHHHH* |
| 6 | 17 | P13S SEL29 RNase H2 | MKVAGIDEAGRGS̲AIGPLVIVAAVVDENSL PKLEELKVRDSKK̲LTPAQREKLFDEIVKVL DDYSVVIVSPQDIDGRKGSMNELEVENFVK ALNSLKVKPDVIYADAADVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV*KLAAALEIKRASQ PELAPEDPEDVEHHHHHH* |
| 7 | 18 | Q48R SEL29 RNase H2 | MKVAGIDEAGRGPAIGPLVIVAAVVDENSL PKLEELKVRDSKKLTPAR̲REKLFDEIVKVL DDYSVVIVSPQDIDGRKG̲SMNELEVENFVK ALNSLKVKPDVIYADAADVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV*KLAAALEIKRASQ PELAPEDPEDVEHHHHHH* |
| 8 | 19 | A107V SEL29 RNase H2 | MKVAGIDEAGRGPAIGPLVIVAAVVDENSL PKLEELKVRDSKKLTPAQREKLFDEIVKVL DDYSVVIVSPQDIDGRKGSMNELEVENFVK ALNSLKVKPDVIYADAV̲DVDEERFARELG ERLNFEAKVVAEHKADA̲KYEIVSAASILAK VIRDREIEKLKAEYGDFGSGYPSDPRTRAFL ENYYREHGEFPPIVRKGWKTLKKIAEKVES EKKAEERQATLDRYFRKV*KLAAALEIKRASQ PELAPEDPEDVEHHHHHH* |
| 9 | 20 | P13S/A107V SEL29 RNase H2 | MKVAGIDEAGRGS̲AIGPLVIVAAVVDENSL PKLEELKVRDSKK̲LTPAQREKLFDEIVKVL DDYSVVIVSPQDIDGRKGSMNELEVENFVK ALNSLKVKPDVIYADAV̲DVDEERFARELG ERLNFEAKVVAEHKADA̲KYEIVSAASILAK VIRDREIEKLKAEYGDFGSGYPSDPRTRAFL ENYYREHGEFPPIVRKGWKTLKKIAEKVES EKKAEERQATLDRYFRKV*KLAAALEIKRASQ PELAPEDPEDVEHHHHHH* |

[1]Location of mutations are shown in bold and underlined. Ending extension and (His)₆-tag is shown in italics.

To determine whether P13S, A107V, and P13S/A107V SEL28 RNase H2 or P13S, Q48R, A107V, or P13S/A107V SEL29 RNase H2 have increased activity in KOD DNA polymerase reaction buffer with rhPCR compared to WT P.a. RNase H2, a quantitative rhPCR assay targeting the rs4939827 SNP in SMAD7 was designed. This SNP has been utilized in the past (Dobosy et al., 2011, and U.S. Pat. No. 8,911,948 B2) to characterize rhPCR efficiency and specificity, and its response under differing conditions is well understood. The primers used in this assay are shown in Table 4, SEQ 21-23. Assays were run in 10 μL reaction volumes. Thermal cycling and data collection were run on a CFX384® Real Time System (Bio-Rad®, Hercules, CA). Briefly, either 200 nM (2 pmol) of the blocked forward primer (SEQ ID NO.: 22) and 200 nM (2 μmol) of the unblocked reverse primer (SEQ ID NO.: 23), or 200 nM (2 μmol) of the unblocked forward primer (SEQ ID NO.: 21) and 200 nM (2 μmol) of the unblocked reverse primer (SEQ ID NO.: 23) were mixed into 1× of internal KOD buffer (ROKStar buffer v2.0 or v1.66) (IDT, Coralville, IA) with 2.5 mM (total) MgSO₄, 0.2 mM (each) dNTPs (MilliporeSigma™, Burlington, MA), and 0.5× EvaGreen® Dye (Biotium Inc., Fremont, CA). RNase H2 dilution buffer (IDT, Coralville, IA) or 21 fmol of WT P.a. (SEQ ID NO.: 1), SEL28 (SEQ ID NO.: 2), SEL29 (SEQ ID NO.: 3), P13S SEL28 (SEQ ID NO.: 14), A107V SEL28 (SEQ ID NO.: 15), P13S/A107V SEL28 (SEQ ID NO.: 16), P13S SEL29 (SEQ ID NO.: 17), Q48R SEL29 (SEQ ID NO.: 18), A107V SEL29 (SEQ ID NO.: 19), or P13S/A107V SEL29 (SEQ ID NO.: 20) RNase H2 enzyme was added to each reaction. 10 ng of genomic cell line DNA (cell line NA12878, Coriell Institute for Medical Research, Camden, NJ), representing a homozygous genotype at the rs4939827 SNP was added to each reaction. Reactions were performed in triplicate, and the results averaged. Reactions were cycled under the following conditions: 95° C.$^{3:00}$→(95° C.$^{0:10}$→60° C.$^{0:30}$)×75. Fluorescence data for the intercalated EvaGreen® were collected after each extension time point. After the assay was completed, the data were analyzed, and $C_q$ values were calculated using the automatic calling function of the Bio-Rad CFX Manager® software. The results are presented in Table 5.

TABLE 4

Sequences and SEQ IDs for the primers used in the experiment described in Example 2.

| SEQ ID NO.: | Name | Sequence[1] |
|---|---|---|
| 21 | rs4939827 For unblocked | CAGCCTCATCCAAAAGAGGAAA |
| 22 | rs4939827 For blocked | CAGCCTCATCCAAAAGAGGAAAcAGGAG-X |
| 23 | rs4939827 Rev unblocked | CTCACTCTAAACCCCAGCATT |

[1]DNA is uppercase, RNA is lowercase. X = Proprietary blocker group resistant to exonuclease.

TABLE 5

$C_q$, $\Delta C_q$, and $\Delta\Delta C_q$ values for the experiments in Example 2.

| RNase H2 in ROKstar buffer v2.0 | Unblocked (SEQ ID NO.: 21) | Blocked (SEQ ID NO.: 22) | [1]$\Delta C_q$ | [2]$\Delta\Delta C_q$ (WT-Mutant) |
|---|---|---|---|---|
| None | 24.2 | >75.0 | >50.8 | n/a |
| WT (P.a.) | 24.3 | 36.7 | 12.4 | n/a |
| SEL28 (Mut ID 1) | 24.2 | 41.3 | 17.1 | 0 |
| P13S SEL28 (Mut ID 3) | 24.3 | >75.0 | >50.8 | <-33.7 |
| A107V SEL28 (Mut ID 4) | 24.1 | 44.1 | 20.0 | -2.9 |
| P13S/A107V SEL28 (Mut ID 5) | 24.1 | 45.7 | 21.5 | -4.5 |
| SEL29 (Mut ID 2) | 24.2 | 48.9 | 24.6 | 0 |
| P13S SEL29 (Mut ID 6) | 23.6 | >75.0 | >51.4 | <-26.8 |
| Q48R SEL29 (Mut ID 7) | 24.2 | 41.4 | 17.2 | 7.4 |
| A107V SEL29 (Mut ID 8) | 24.1 | 38.0 | 13.9 | 10.7 |
| P13S/A107V SEL29 (Mut ID 9) | 24.4 | 51.4 | 26.9 | -2.3 |

TABLE 5-continued $C_q$, $\Delta C_q$, and $\Delta\Delta C_q$ values for the experiments in Example 2.

| RNase H2 in ROKstar buffer v1.66 | Unblocked (SEQ ID NO.: 21) | Blocked (SEQ ID NO.: 22) | [1]$\Delta C_q$ | [2]$\Delta\Delta C_q$ (WT-Mutant) |
|---|---|---|---|---|
| None | 24.7 | >75.0 | >50.3 | n/a |
| WT (P.a.) | 24.6 | 45.7 | 21.1 | n/a |
| SEL28 (Mut ID 1) | 25.0 | 55.6 | 30.6 | 0 |
| P13S SEL28 (Mut ID 3) | 24.6 | >75.0 | >50.4 | <−19.8 |
| A107V SEL28 (Mut ID 4) | 24.8 | 60.6 | 35.8 | −5.2 |
| P13S/A107V SEL28 (Mut ID 5) | 24.7 | 56.4 | 31.8 | −1.2 |
| SEL29 (Mut ID 2) | 24.1 | 54.5 | 30.3 | 0 |
| P13S SEL29 (Mut ID 6) | 24.9 | >75.0 | >50.1 | <−19.8 |
| Q48R SEL29 (Mut ID 7) | 25.0 | 50.4 | 25.4 | 4.9 |
| A107V SEL29 (Mut ID 8) | 24.9 | 46.9 | 21.9 | 8.4 |
| P13S/A107V SEL29 (Mut ID 9) | 24.7 | 57.4 | 32.8 | −2.4 |

[1]$\Delta C_q$ values were calculated as the difference between the $C_q$ value for the blocked primer (SEQ ID NO.: 22) and the $C_q$ value for the unblocked primer (SEQ ID NO.: 21).
[2]$\Delta\Delta C_q$ values were calculated as the difference between the $\Delta C_q$ value for the background SEL28 or SEL29 RNase H2 and the $\Delta C_q$ value for the mutant SEL28 or SEL29 RNase H2.

These data show that Q48R SEL29 and A107V SEL29 RNase H2 have increased enzymatic activity in *Thermococcus kodakarensis* DNA polymerase reaction buffer compared to the background SEL29 RNase H2, but P13S SEL29 RNase H2 and P13S/A107V RNase H2 does not. In addition, P13S SEL28, A107V SEL28, and P13S/A107V RNase H2 do not increase enzymatic activity in *Thermococcus kodakarensis* DNA polymerase reaction buffer compared to the background SEL28 RNase H2. Without the addition of any RNase H2, the blocked primers are not cleaved and thus cannot support PCR. Use of a proprietary exonuclease-resistant blocked primer is necessary to prevent deblocking of the primer by the high-fidelity DNA polymerase. WT (P.a.) RNase H2 is capable of cleaving the blocked primers, but has a delay in amplification, resulting in a $\Delta C_q$ of 12.4 cycles in ROKstar buffer v2.0 and 21.1 cycles in ROKstar buffer v1.66 compared to the unblocked primers. The $\Delta C_q$ quantification of the delay in amplification increases to 17.1 cycles for SEL28 RNase H2 and 24.6 cycles for SEL29 RNase H2 in ROKstar buffer v2.0 and increases to 30.6 cycles for SEL28 RNase H2 and 30.3 cycles for SEL29 RNase H2 in ROKstar buffer v1.66. The $\Delta C_q$ quantification of the delay in amplification decreases with Q48R SEL29 RNase H2 (17.2 cycles in ROKstar buffer v2.0 and 25.4 cycles in ROKstar buffer v1.66), and A107V RNase H2 (13.9 cycles in ROKstar buffer v2.0 and 21.9 cycles in ROKstar buffer v1.66). P13S/A107V SEL29 RNase H2 increases the $\Delta C_q$ quantification of the delay in amplification to 26.9 cycles in ROKstar buffer v2.0 and 32.8 cycles in ROKstar buffer v1.66. P13S SEL28 and P13S SEL29 RNase H2 have no apparent activity in either ROKstar buffer v2.0 or v1.66. In addition, P13S/A107V SEL28 RNase H2 increases the $\Delta C_q$ quantification of the delay in amplification to 21.5 cycles in ROKstar buffer v2.0 and 31.8 cycles in ROKstar buffer v1.66. A107V SEL28 RNase H2 increases the $\Delta C_q$ quantification of the delay in amplification to 20.0 cycles in ROKstar buffer v2.0 and 35.8 cycles in ROKstar buffer v1.66. These results contrast with the mutations in P.a. RNase H2, as Q48R, A107V, and P13S/A107V P.a. RNase H2 all have increased enzymatic activity in *Thermococcus kodakarensis* DNA polymerase reaction buffer, and P13S P.a. RNase H2 had lower, yet measurable, enzymatic activity in *Thermococcus kodakarensis* DNA polymerase reaction buffer. Q48R SEL29 and A107V SEL29 RNase H2 improve enzymatic activity—though to differing degrees—when used with *Thermococcus kodakarensis* DNA polymerase reaction buffer.

Example 3. Q48R SEL29 and A107V SEL29 RNase 112 Increase Mismatch Discrimination Compared to WT RNase 112 when the Mismatch is Placed Opposite of the RNA The specific activity of the enzyme was determined using a fluorescence-based kinetic assay. The sequences for the DNA substrates are shown in Table 6, SEQ ID NOs.: 24-25. The substrate is a DNA hairpin with a matched RNA base within the double-stranded region. Attached to the 3' end of the probe is a 6-FAM (6-carboxyfluorescein); attached to the 5' end of the probe is an Iowa Black® FQ (SEQ ID NO.: 24). The fluorescence of the 6-FAM is quenched by the Iowa Black® FQ moiety in the intact hairpin probe. RNase H2 cleaves 5' of the RNA base and releases the 3' end of the probe with the 6-FAM. Thus, the fluorescence of the 6-FAM is no longer be quenched and can fluoresce. A DNA hairpin with the RNA base but without the fluorophore or the quencher was used as a competitor (SEQ ID NO.: 25). Assays were performed in 10 µL reaction volumes. Data collection was carried out with a LightCycler® 480 II (Roche Life Science, Indianapolis, IN). Briefly, 1× of the rhAmp™ Backbone v3 was used in combination with 200 nM (2 µmol) of labeled hairpin (SEQ ID NO.: 24) and 10 µM (100 pmol) of competitor hairpin (SEQ ID NO.: 25). 0.5, 1.0, 2.0, or 5.0 fmol of WT P.a. RNase H2 (SEQ ID NO.: 1) or mutant RNase H2 (SEQ ID NOs.: 18-19) were added to each reaction. Reactions were initially kept at 4° C. to prevent cleavage of substrate prior to starting the assay. Samples were run at 65° C. The fluorescence excitation wavelength was 483 nm; the fluorescence emission wavelength was 533 nm. Fluorescence intensities were collected every 13.75 seconds for 135 minutes. The initial velocities and the velocity per femtomole for each reaction were calculated. The velocities per femtomole for each mutant was normalized to the values of WT P.a. RNase H2, which was previously determined to have a specific activity of 17 Units per µg of enzyme. Q48R SEL29 RNase H2 has a specific activity of 46.03 Units per µg of enzyme, and A107V SEL29 RNase H2 has a specific unit activity of 7.77 Units per µg of enzyme.

TABLE 6

Sequences and SEQ IDs for the DNA hairpins to determine RNase H2 unit activity.

| SEQ ID NO.: | Name | Sequence[1] |
|---|---|---|
| 24 | Dye-quencher labeled hairpin | Q-TATAAGCTACCAGCATGGTTTTT CCATGCTGGTAGcTTATA-F |
| 25 | Native competitor hairpin | TATAAGCTACCAGCATGGTTTTT CCATGCTGGTAGcTTATA |

[1]DNA is uppercase, RNA is lowercase. Q = Iowa Black ® FQ. F = 6-FAM (Fluorescein).

To fully determine whether these mutant RNase H2 enzymes can improve mismatch discrimination with the mismatch directly opposite of the RNA base, a synthetic, quantitative rhPCR assay was utilized as described previously (Dobosy et al, 2011, and U.S. Pat. No. 8,911,948 B2). This assay can directly compare the effects of each specific single-base mismatch compared to the perfect match. The primers used in this assay are shown in Table 7, SEQ ID NOs.: 26-31. Assays were run in 10 μL reaction volumes. Thermal cycling and data collection were run on a CFX384® Real Time System (Bio-Rad®, Hercules, CA). Briefly, either 200 nM (2 μmol) of a blocked reverse primer (SEQ ID NOs.: 28-31) and 200 nM (2 μmol) of the unblocked forward primer (SEQ ID NO.: 26), or 200 nM (2 μmol) of the unblocked reverse primer (SEQ ID NO.: 27) and 200 nM (2 μmol) of the unblocked forward primer (SEQ ID NO.: 26) were mixed into 1×iQ™ SYBR® Green Supermix® (Bio-Rad®, Hercules, CA). 5 mU of WT P.a. (SEQ ID NO.: 1), 40 mU of Q48R SEL29 (SEQ ID NO.: 18), or 5 mU of A107V SEL29 (SEQ ID NO.: 19) RNase H2 enzyme was added to each reaction. 20,000 copies of each synthetic target sequence (SEQ ID NOs.: 32-35), each with a different nucleotide directly opposite the RNA base, were added to each reaction. Reactions were performed in triplicate, and results averaged. Reactions were cycled under the following conditions: 95° C.$^{3:00}$→(95° C.$^{0:10}$→60° C.$^{0:30}$)×75. Fluorescence data for the intercalated SYBR® Green were collected after each extension time point. After the assay was completed, the data were analyzed, and the average $C_q$ and $\Delta C_q$ values for each pair-wise combination were calculated. The results are presented in Tables 8 and 9.

TABLE 7

Sequences and SEQ IDs for the primers and templates used in the experiment described in Example 2.

| SEQ ID NO.: | Name | Sequence[1] |
|---|---|---|
| 26 | Syn For unblocked | AGCTCTGCCCAAAGATTACCCTG |
| 27 | Syn Rev unblocked | CTGAGCTTCATGCCTTTACTGT |
| 28 | Syn Rev rA blocked | CTGAGCTTCATGCCTTTACTGTaCCCCC-X |
| 29 | Syn Rev rC blocked | CTGAGCTTCATGCCTTTACTGTcCCCCC-X |
| 30 | Syn Rev rG blocked | CTGAGCTTCATGCCTTTACTGTgCCCCC-X |
| 31 | Syn Rev rU blocked | CTGAGCTTCATGCCTTTACTGTuCCCCC-X |
| 32 | Syn A template | AGCTCTGCCCAAAGATTACCCTGACAGCTAAGT GGCAGTGGAAGTTGGCCTCAGAAGTAGTGGCCA GCTGTGTGTCGGGGAACAGTAAAGGCATGAAGC TCAG |
| 33 | Syn C template | AGCTCTGCCCAAAGATTACCCTGACAGCTAAGT GGCAGTGGAAGTTGGCCTCAGAAGTAGTGGCCA GCTGTGTGTCGGGGCACAGTAAAGGCATGAAGC TCAG |
| 34 | Syn G template | AGCTCTGCCCAAAGATTACCCTGACAGCTAAGT GGCAGTGGAAGTTGGCCTCAGAAGTAGTGGCCA GCTGTGTGTCGGGGACAGTAAAGGCATGAAGC TCAG |
| 35 | Syn U template | AGCTCTGCCCAAAGATTACCCTGACAGCTAAGT GGCAGTGGAAGTTGGCCTCAGAAGTAGTGGCCA GCTGTGTGTCGGGGTACAGTAAAGGCATGAAGC TCAG |

[1]DNA is uppercase, RNA is lowercase. X = C3 spacer (propanediol) blocker group. Location of the mismatch is shown in bold and underlined in the synthetic template.

TABLE 8

$C_q$ values for the experiment described in Example 2.

| RNase H2 enzyme | Reverse primer name | Reverse primer SEQ ID NO.: | $C_q$ for Syn A template | $C_q$ for Syn C template | $C_q$ for Syn G template | $C_q$ for Syn T template |
|---|---|---|---|---|---|---|
| WT (P.a.) RNase H2 | Syn Rev unblocked | 27 | 26.2 | 27.5 | 26.8 | 27.7 |
| | Syn Rev rA blocked | 28 | 28.8 | 28.6 | 32.7 | 28.2 |
| | Syn Rev rC blocked | 29 | 26.8 | 29.4 | 27.2 | 28.6 |
| | Syn Rev rG blocked | 30 | 37.9 | 27.6 | 35.6 | 33.5 |
| | Syn Rev rU blocked | 31 | 26.4 | 32.3 | 36.6 | 28.8 |
| Q48R SEL29 RNase H2 (Mut ID 7) | Syn Rev unblocked | 27 | 26.7 | 27.5 | 27.0 | 28.1 |
| | Syn Rev rA blocked | 28 | 37.1 | 39.9 | 41.5 | 29.2 |
| | Syn Rev rC blocked | 29 | 35.5 | 51.6 | 27.6 | 40.8 |
| | Syn Rev rG blocked | 30 | 37.1 | 32.7 | 39.1 | 43.7 |
| | Syn Rev rU blocked | 31 | 26.3 | 46.6 | 40.3 | 44.2 |
| WT (P.a.) RNase H2 | Syn Rev unblocked | 27 | 26.1 | 26.1 | 26.8 | 28.5 |
| | Syn Rev rA blocked | 28 | 28.5 | 34.7 | 36.9 | 26.9 |
| | Syn Rev rC blocked | 29 | 26.8 | 37.4 | 26.9 | 30.9 |
| | Syn Rev rG blocked | 30 | 37.4 | 28.7 | 37.6 | 39.6 |
| | Syn Rev rU blocked | 31 | 26.3 | 41.9 | 37.5 | 31.3 |
| A107V SEL29 RNase H2 (Mut ID 8) | Syn Rev unblocked | 27 | 26.3 | 26.9 | 26.7 | 26.8 |
| | Syn Rev rA blocked | 28 | 39.4 | 41.6 | 38.4 | 27.4 |
| | Syn Rev rC blocked | 29 | 38.9 | 53.0 | 27.2 | 44.6 |
| | Syn Rev rG blocked | 30 | 40.2 | 31.6 | 37.7 | 40.7 |
| | Syn Rev rU blocked | 31 | 26.5 | 46.9 | 36.9 | 40.5 |
| WT (P.a.) RNase H2 | Syn Rev unblocked | 27 | 25.2 | 26.3 | 25.2 | 25.6 |
| | Syn Rev rA blocked | 28 | 30.2 | 26.1 | 35.0 | 24.8 |
| | Syn Rev rC blocked | 29 | 25.2 | 26.3 | 25.2 | 25.6 |
| | Syn Rev rG blocked | 30 | 36.0 | 25.3 | 35.6 | 31.6 |
| | Syn Rev rU blocked | 31 | 24.5 | 28.7 | 34.5 | 25.9 |

TABLE 8-continued $C_q$ values for the experiment described in Example 2.

| RNase H2 enzyme | Reverse primer name | Reverse primer SEQ ID NO.: | $C_q$ for Syn A template | $C_q$ for Syn C template | $C_q$ for Syn G template | $C_q$ for Syn T template |
|---|---|---|---|---|---|---|
| SEL29 RNase H2 (Mut ID 2)[1] | Syn Rev unblocked | 27 | 24.4 | 24.6 | 24.9 | 24.7 |
| | Syn Rev rA blocked | 28 | 37.2 | 38.7 | 37.2 | 25.1 |
| | Syn Rev rC blocked | 29 | 37.0 | 39.6 | 25.3 | 36.6 |
| | Syn Rev rG blocked | 30 | 37.9 | 26.0 | 36.7 | 38.6 |
| | Syn Rev rU blocked | 31 | 26.3 | 39.6 | 36.4 | 37.9 |

TABLE 9

$\Delta C_q$ values for the experiment described in Example 2.

| RNase H2 enzyme | Reverse primer name | Reverse primer SEQ ID NO.: | $\Delta C_q$ for Syn A template | $\Delta C_q$ for Syn C template | $\Delta C_q$ for Syn G template | $\Delta C_q$ for Syn T template |
|---|---|---|---|---|---|---|
| WT (P.a.) RNase H2 | Syn Rev rA blocked | 28 | 0.6 | 0.3 | 4.5 | 0 |
| | Syn Rev rC blocked | 29 | −0.4 | 2.2 | 0 | 1.5 |
| | Syn Rev rG blocked | 30 | 10.3 | 0 | 8.0 | 5.9 |
| | Syn Rev rU blocked | 31 | 0 | 6.0 | 10.2 | 2.4 |
| Q48R SEL29 RNase H2 (Mut ID 7) | Syn Rev rA blocked | 28 | 7.9 | 10.7 | 12.3 | 0 |
| | Syn Rev rC blocked | 29 | 8.0 | 24.1 | 0 | 13.2 |
| | Syn Rev rG blocked | 30 | 4.5 | 0 | 6.5 | 11.0 |
| | Syn Rev rU blocked | 31 | 0 | 20.3 | 14.0 | 17.9 |
| WT (P.a.) RNase H2 | Syn Rev rA blocked | 28 | 1.5 | 7.7 | 9.9 | 0 |
| | Syn Rev rC blocked | 29 | −0.1 | 10.5 | 0 | 4.0 |
| | Syn Rev rG blocked | 30 | 8.7 | 0 | 8.9 | 10.9 |
| | Syn Rev rU blocked | 31 | 0 | 15.6 | 11.2 | 5.1 |
| A107V SEL29 RNase H2 (Mut ID 8) | Syn Rev rA blocked | 28 | 12.0 | 14.2 | 11.0 | 0 |
| | Syn Rev rC blocked | 29 | 11.7 | 25.7 | 0 | 17.4 |
| | Syn Rev rG blocked | 30 | 8.7 | 0 | 6.2 | 9.1 |
| | Syn Rev rU blocked | 31 | 0 | 20.4 | 10.4 | 14.0 |
| WT (P.a.) RNase H2 | Syn Rev rA blocked | 28 | 5.4 | 1.4 | 10.3 | 0 |
| | Syn Rev rC blocked | 29 | 0.0 | 1.0 | 0 | 0.3 |
| | Syn Rev rG blocked | 30 | 10.7 | 0 | 10.3 | 6.3 |
| | Syn Rev rU blocked | 31 | 0 | 4.2 | 10.0 | 1.4 |
| SEL29 RNase H2 (Mut ID 2) | Syn Rev rA blocked | 28 | 12.0 | 13.5 | 12.1 | 0 |
| | Syn Rev rC blocked | 29 | 11.8 | 14.3 | 0 | 11.3 |
| | Syn Rev rG blocked | 30 | 11.9 | 0 | 10.7 | 12.6 |
| | Syn Rev rU blocked | 31 | 0 | 13.3 | 10.1 | 11.6 |

$\Delta C_q$ values from Table 9 were calculated as the difference between the $C_q$ value for the nucleotide-specific primer for each template and the $C_q$ value for the perfect match template.

These data show a massive increase in mismatch discrimination when the mismatch is opposite of rC for Q48R SEL29 and A107V SEL29 RNase H2 (~14.0 cycles and ~13.5 cycles respectively). In particular, there is a large increase in mismatch discrimination for the rC:C pair for Q48R SEL29 and A107V SEL29 RNase H2 (21.9 cycles and 15.2 cycles respectively). When the mismatch is opposite of rU, there is a significant increase in mismatch discrimination for Q48R SEL29 RNase H2 (~11.2 cycles), but a less significant increase for A107V SEL29 RNase H2 (~4.3 cycles). When the mismatch is opposite of rA, there is a significant change in mismatch discrimination for Q48R SEL29 and A107V SEL29 RNase H2 (~8.5 cycles and ~6.0 cycles respectively). When the mismatch is opposite of rG, there is little change in mismatch discrimination; this lack of change of mismatch discrimination is less crucial, as the mismatch discrimination was already rather good for rG mismatches using WT RNase H2. These increases in mismatch discrimination for Q48R SEL29 and A107V SEL29 RNase H2 are similar to those shown for the background SEL29 RNase H2. Both mutations improve mismatch discrimination when the mismatch is located directly opposite of the RNA base, but to different degrees and with different specificities.

Example 4. Q48R SEL29 and A107V SEL29 RNase 112 Increase Mismatch Discrimination Compared to WT RNase 112 when the Mismatch is Placed 5' of the RNA To determine the degree of mismatch discrimination when the mismatch is located 5' of the RNA nucleotide using the Q48R SEL29 and A107V SEL29 RNase H2 enzymes, an assay targeting rs113488022—the V600E SNP in the human BRAF gene—was designed with the SNP located immediately 5' of the RNA. The primers used in this assay are shown in Table 10, SEQ ID NOs.: 36-39. Assays were run in 10 μL reaction volumes. Thermal cycling and data collection were run on a CFX384® Real Time System (Bio-Rad®, Hercules, CA). Briefly, either 200 nM (2 μmol) of a blocked forward primer (SEQ ID NOs.: 38 or 39) and 200 nM (2 μmol) of the unblocked reverse primer (SEQ ID NO.: 37), or 200 nM (2 μmol) of the unblocked forward primer (SEQ ID NO.: 36) and 200 nM (2 μmol) of the unblocked reverse primer (SEQ ID NO.: 37) were mixed into 1×iQ™ SYBR® Green Supermix®. 5 mU or 10 mU of WT (SEQ ID NO.: 1) P.a. RNase H2 enzyme, 5 mU or 10 mU of SEL29 (SEQ ID NO.: 3) RNase H2 enzyme, 20 mU or 40 mU of Q48R SEL29 (SEQ ID NO.: 18) RNase H2 enzyme, or 5 mU or 10 mU of A107V SEL29 (SEQ ID NO.: 19) RNase H2 enzyme was added to each reaction. 2,000 copies of synthetic double-stranded gBlock® (IDT, Coralville, IA) template, each corresponding to the homozygous genotypes at the rs113488022 SNP (SEQ ID NOs.: 40 or 41), were added to each reaction. Reactions were performed in triplicate. Reactions were cycled under the following conditions: 95° C.$^{3:00}$→(95° C.$^{0:10}$→60° C.$^{0:30}$)×65. Fluorescence data for the intercalated SYBR® Green were collected after each extension time point. After the assay was completed, the data were analyzed, and the average $C_q$ and $\Delta C_q$ values for each pair-wise combination were calculated. The results are presented in Table 11.

TABLE 10

Sequences and SEQ IDs for the primers and templates used in the experiment described in Example 4.

| SEQ ID NO.: | Name | Sequence[1] |
|---|---|---|
| 36 | rs113488022 For unblocked | GTGATTTTGGTCTAGCTACAGT |
| 37 | rs113488022 Rev unblocked | CCTCAATTCTTACCATCCACAAA |
| 38 | rs113488022 TrG 4dmx | GTGATTTTGGTCTAGCTACAGTgAAATG-x |
| 39 | rs113488022 ArG 4dmx | GTGATTTTGGTCTAGCTACAGAgAAATG-x |
| 40 | gBlock ® T template | TAAGAGGAAAGATGAAGTACTATGTTTTAAAGAATATTATATTACAGAATTATAGAAATTAGATCTCTTACCTAAACTCTTCATAATGCTTGCTCTGATAGGAAAATGAGATCTACTGTTTTCCTTTACTTACTACACCTCAGATATATTTCTTCATGAAGACCTCACAGTAAAAATAGGTGATTTTGGTCTAGCTACAGTGAAATCTCGATGGAGTGGGTCCCATCAGT$\overline{\text{TT}}$TGAACAGTTGTCTGGATCCATTTTGTGGATGGTAAGAATTGAGGCTATTTTTCCACTGATTAAATTTTTGGCCCTGAGATGCTGCTGAGTTACTAGAAAGTCATTGAAGGTCTCAACTATAGTATTTTCATAGTTCCCAGTATTCACAAAAATCAGTGTTCTTATTTTTT |
| 41 | gBlock ® A template | TAAGAGGAAAGATGAAGTACTATGTTTTAAAGAATATTATATTACAGAATTATAGAAATTAGATCTCTTACCTAAACTCTTCATAATGCTTGCTCTGATAGGAAAATGAGATCTACTGTTTTCCTTTACTTACTACACCTCAGATATATTTCTTCATGAAGACCTCACAGTAAAAATAGGTGATTTTGGTCTAGCTACAGAGAAATCTCGATGGAGTGGGTCCCATCAGT$\overline{\text{TT}}$TGAACAGTTGTCTGGATCCATTTTGTGGATGGTAAGAATTGAGGCTATTTTTCCACTGATTAAATTTTTGGCCCTGAGATGCTGCTGAGTTACTAGAAAGTCATTGAAGGTCTCAACTATAGTATTTTCATAGTTCCCAGTATTCACAAAAATCAGTGTTCTTATTTTTT |

[1]DNA is uppercase, RNA is lowercase. X = C3 spacer (propanediol) blocker group. Location of the mismatch is shown in bold and underlined in the gBlocks ®.

TABLE 11

$C_q$ and $\Delta C_q$ values for the experiments in Example 4.

| RNase H2 | Forward Primer | T template | A template | $\Delta C_q$ | T template | A template | $\Delta C_q$ |
|---|---|---|---|---|---|---|---|
| | | 5 mU RNase H2 | | | 10 mU RNase H2 | | |
| WT | Unblocked | 25.9 | 26.6 | 0.7 | 25.5 | 26.3 | 0.9 |
| | TrG | 27.6 | 31.4 | 3.8 | 26.5 | 30.0 | 3.5 |
| | ArG | 38.1 | 28.0 | 10.1 | 37.4 | 27.4 | 10.0 |

TABLE 11-continued $C_q$ and $\Delta C_q$ values for the experiments in Example 4.

| RNase H2 | Forward Primer | T template | A template | $\Delta C_q$ | T template | A template | $\Delta C_q$ |
|---|---|---|---|---|---|---|---|
| A107V SEL29 | Unblocked | 25.6 | 26.2 | 0.6 | 25.4 | 26.1 | 0.8 |
| | TrG | 28.0 | 35.9 | 7.8 | 26.9 | 34.2 | 7.3 |
| | ArG | 38.7 | 27.5 | 11.2 | 38.9 | 27.4 | 11.5 |
| WT | Unblocked | 26.0 | 26.6 | 0.6 | 25.4 | 26.2 | 0.7 |
| | TrG | 27.4 | 31.9 | 4.5 | 26.7 | 30.3 | 3.6 |
| | ArG | 38.5 | 27.5 | 10.9 | 37.5 | 27.1 | 10.4 |
| SEL29 | Unblocked | 26.0 | 26.6 | 0.5 | 25.4 | 26.3 | 0.9 |
| | TrG | 29.1 | 36.3 | 7.2 | 26.9 | 34.3 | 7.4 |
| | ArG | 39.6 | 27.8 | 11.8 | 38.4 | 27.5 | 10.9 |
| | | 20 mU RNase H2 | | | 40 mU RNase H2 | | |
| Q48R SEL29 | Unblocked | 25.7 | 26.5 | 0.9 | 25.4 | 26.2 | 0.8 |
| | TrG | 30.1 | 36.2 | 6.1 | 27.8 | 34.7 | 6.9 |
| | ArG | 38.6 | 28.0 | 10.6 | 37.7 | 27.5 | 10.2 |

These data show that Q48R SEL29 and A107V SEL29 RNase H2 significantly improve mismatch discrimination 5' of the RNA nucleotide. The $\Delta C_q$ quantification for the TrG primer increases from 3.8 cycles with WT P.a. RNase H2 to 5.9 cycles with A107V SEL29 RNase H2 (for 5 mU of WT RNase H2 and A107V SEL29 RNase H2) and from 4.5 cycles with WT P.a. RNase H2 to 6.9 cycles with Q48R SEL29 RNase H2 (for 5 mU of WT RNase H2 and 40 mU of Q48R SEL29 RNase H2). The $\Delta C_q$ quantification for the ArG primer increases from 10.1 cycles with WT P.a. RNase H2 to 11.2 cycles with A107V SEL29 RNase H2 (for 5 mU of WT RNase H2 and A107V SEL29 RNase H2), but decreased from 10.9 cycles with WT P.a. RNase H2 to 10.2 cycles with Q48R SEL29 RNase H2 (for 5 mU of WT RNase H2 and 40 mU of Q48R SEL29 RNase H2). The change of the mismatch discrimination with the ArG primer is less crucial, as the $\Delta C_q$ was already rather effective for this primer using the WT enzyme. These increases in mismatch discrimination for Q48R SEL29 and A107V SEL29 RNase H2 are similar to those for the background SEL29 RNase H2. Q48R SEL29 and A107V SEL29 RNase H2 therefore improve mismatch discrimination when the mismatch is located 5' of the RNA base.

Example 5. Q48R SEL29 and A107V SEL29 RNase 112 Increase Mismatch Discrimination Compared to WT RNase 112 when the Mismatch is Placed 3' of the RNA To determine whether Q48R SEL29 and A107V SEL29 RNase H2 enzymes can improve mismatch discrimination when the mismatch is located 3' of the RNA nucleotide, an assay targeting the rs7583169 and rs3117947 SNPs were designed with the mismatch located immediately 3' of the RNA. The primers used in this assay are shown in Table 12, SEQ NOs.: 42-47. Assays were run in 10 µL reaction volumes. Thermal cycling and data collection were run on a CFX384 ® Real Time System (Bio-Rad®, Hercules, CA). Briefly, either 200 nM (2 µmol) of the blocked forward primer (SEQ ID NOs.: 43 or 46) and 200 nM (2 µmol) of the unblocked reverse primer (SEQ ID NOs.: 44 or 47), or 200 nM (2 µmol) of the unblocked forward primer (SEQ ID NOs.: 42 or 45) and 200 nM (2 pmol) of the unblocked reverse primer (SEQ ID NOs.: 44 or 47) were mixed into 1× of PrimeTime® Gene Expression Master Mix (IDT, Coralville, IA) with 3.0 mM (total) MgCl$_2$ and 0.5× EvaGreen® Dye (Biotium Inc., Fremont, CA). 5 mU or 10 mU of WT (SEQ ID NO.: 1) P.a. RNase H2 enzyme, 50 mU or 100 mU of Q48R SEL29 (SEQ ID NO.: 18) RNase H2 enzyme, or 20 mU or 40 mU of A107V SEL29 (SEQ ID NO.: 19) RNase H2 enzyme was added to each reaction. 20 ng of genomic cell line DNA (cell lines NA12878 and NA24385, Coriell Institute for Medical Research, Camden, NJ), representing the two homozygous genotypes at the rs7583169 and rs3117947 SNPs were added to each reaction. Reactions were performed in triplicate, and the results averaged. Reactions were cycled under the following conditions: 95° C.$^{3:00}$→(95° C.$^{0:10}$→60° C.$^{0:30}$)×65. Fluorescence data for the intercalated EvaGreen® were collected after each extension time point. After the assay was completed, the data were analyzed, and the average $C_q$ and $\Delta C_q$ values for each pair-wise combination were calculated. The results are presented in Table 13.

TABLE 12

Sequences and SEQ IDs for the primers used in the experiment described in Example 5.

| SEQ ID NO.: | Name | Sequence[1] |
|---|---|---|
| 42 | rs7583169 For unblocked | GGCAGATTTTCTTCTGCACCGCG |
| 43 | rs7583169 For blocked | GGCAGATTTTCTTCTGCACCGCgGT-X-TC-X |
| 44 | rs7583169 Rev unblocked | TCCCGTCGAGCACCAGCAATTTTACTC |
| 45 | rs3117947 For unblocked | CTTTGGATAAGGAAGAAGCCAACT |
| 46 | rs3117947 For blocked | CTTTGGATAAGGAAGAAGCCAACuGC-X-AG-X |
| 47 | rs3117947 Rev unblocked | GGGAGCTTGAAATGAACAAGGTGAGAAG |

[1]DNA is uppercase, RNA is lowercase. X = C3 spacer (propanediol) blocker group. Location of the mismatch is shown in bold and underlined in the gBlocks®.

TABLE 13

$C_q$ and $\Delta C_q$ values for the experiments in Example 5.

| RNase H2 | SNP | Forward Primer SEQ ID NO. | NA 12878 | NA 24385 | $\Delta C_q$ | NA 12878 | NA 24385 | $\Delta C_q$ |
|---|---|---|---|---|---|---|---|---|
| | | | 5 mU RNase H2 | | | 10 mU RNase H2 | | |
| WT | rs7583169 | 42 | 25.3 | 25.1 | −0.2 | 24.8 | 24.6 | −0.2 |
| | | 43 | 26.1 | 26.1 | 0.0 | 25.2 | 25.2 | −0.1 |
| | rs3117947 | 45 | 25.9 | 25.3 | −0.6 | 24.9 | 24.7 | −0.2 |
| | | 46 | 28.0 | 38.7 | 10.7 | 26.2 | 32.6 | 6.3 |
| SEL29 (Mut ID 2) | rs7583169 | 42 | 25.0 | 25.6 | 0.6 | 24.7 | 25.2 | 0.4 |
| | | 43 | 26.0 | 30.5 | 4.5 | 25.5 | 28.2 | 2.8 |
| | rs3117947 | 45 | 25.1 | 24.7 | −0.5 | 25.0 | 25.1 | 0.1 |
| | | 46 | 26.7 | 40.9 | 14.2 | 26.3 | 37.9 | 11.6 |
| | | | 20 mU RNase H2 | | | 40 mU RNase H2 | | |
| A107V SEL29 (Mut ID 8) | rs7583169 | 42 | 25.0 | 24.9 | −0.2 | 24.6 | 24.8 | 0.2 |
| | | 43 | 25.5 | 28.1 | 2.6 | 25.1 | 26.5 | 1.4 |
| | rs3117947 | 45 | 25.3 | 25.2 | −0.1 | 24.7 | 24.9 | 0.1 |
| | | 46 | 32.2 | 52.2 | 20.0 | 28.5 | 50.9 | 22.3 |

TABLE 13-continued $C_q$ and $\Delta C_q$ values for the experiments in Example 5.

| RNase H2 | SNP | Forward Primer SEQ ID NO. | NA 12878 | NA 24385 | $\Delta C_q$ | NA 12878 | NA 24385 | $\Delta C_q$ |
|---|---|---|---|---|---|---|---|---|
| | | | 50 mU RNase H2 | | | 100 mU RNase H2 | | |
| Q48R SEL29 (Mut ID 7) | rs7583169 | 42 | 25.2 | 24.9 | −0.3 | 25.1 | 24.9 | −0.2 |
| | | 43 | 25.9 | 44.5 | 18.6 | 25.3 | 36.8 | 11.5 |
| | rs3117947 | 45 | 25.4 | 25.5 | 0.1 | 25.1 | 24.9 | −0.2 |
| | | 46 | 32.8 | 55.0 | 22.2 | 28.6 | 49.0 | 20.4 |

$\Delta C_q$ values from Table 13 were calculated as the difference between the $C_q$ value for the mismatched template (NA24385) and the $C_q$ value for the matched template (NA12878). The data for SEL29 RNase H2 were collected previously.

These data show that Q48R SEL29 and A107V SEL29 significantly increase mismatch discrimination 3' of the RNA nucleotide. The $\Delta C_q$ quantification of the mismatch discrimination for the rs7583169 SNP increases from 0.0 cycles with WT P.a. RNase H2 to 1.4 cycles with A107V SEL29 RNase H2 (for 5 mU of WT RNase H2 and 40 mU of A107V SEL29 RNase H2) and from 0.0 cycles with WT P.a. RNase H2 to 11.5 cycles with Q48R SEL29 RNase H2 (for 5 mU of WT RNase H2 and 100 mU of Q48R SEL29 RNase H2). The $\Delta C_q$ quantification of the mismatch discrimination for the rs3117947 SNP increases from 10.7 cycles with WT P.a. RNase H2 to 22.3 cycles with A107V SEL29 RNase H2 (for 5 mU of WT RNase H2 and 40 mU of A107V SEL29 RNase H2) and from 10.7 cycles with WT P.a. RNase H2 to 20.4 cycles with Q48R SEL29 RNase H2 (for 5 mU of WT RNase H2 and 100 mU of Q48R SEL29 RNase H2). These increases in mismatch discrimination for Q48R SEL29 and A107V SEL29 RNase H2 are significantly greater than those for the background SEL29 RNase H2. Q48R SEL29 and A107V SEL29 RNase H2 therefore improve mismatch discrimination when the mismatch is located 3' of the RNA base.

Example 6. Use of Q48R SEL29 and A107V SEL29 Hybrid RNase H2 Proteins in LAMP Reactions This example outlines a method of demonstrating the use of hybrid RNase H2 proteins in a LAMP reaction to reduce primer-dimer formation.

To evaluate the functionality of rhPrimers for LAMP protocols that include the different RNase H2 proteins (WT or hybrid RNase H2 proteins), three assays could be designed using (1) unmodified control primers; "Gen1" rDDDDMx primers wherein "r" is an RNA base, "D" is a DNA base, "m" is a mismatch and "x" is a C3 spacer; and "Gen2" rDxxDM primers. The details of the assays to be used in the evaluations are detailed in Tables 14, 15, and 16. LAMP reactions utilizing each type of primer will be held at 25° C. (room temperature) for 0 or 2 hours prior to testing. This will allow for the formation of the primer-dimer products. After the room temperature hold, all reactions will be run at 65° C. for 2 hours in a BioRad CFX384 or Roche LightCycler 480. Signal generation in all of these reactions will be performed with 1× EvaGreen, added to the reaction (see: *Biotechnology Letters*, December 2007, Volume 29, Issue 12, pp 1939-1946).

TABLE 14

Controlled unmodified primer designs.

| SEQ ID NO.: | Name | Sequence |
|---|---|---|
| 48 | FTP-lambda | CAGCCAGCCGCAGCACGTTCGCTCATAGGAGATATGGTAGAGCCGC |
| 49 | BIP-lambda | GAGAGAATTTGTACCACCTCCCACCGGGCACATAGCAGTCCTAGGGACAGT |
| 50 | E3-lambda | GGCTTGGCTCTGCTAACACGTT |
| 51 | B3-lambda | GGACGTTTGTAATGTCCGCTCC |
| 52 | rhLAMP Probe-lambda | F-ACGTGCTGCGgCTGGCTGGT-Q |
| 53 | FTP-hCFTR | CCAAAGAGTAAAGTCCTTCTCTCTCGAGAGACTGTTGGCCCTTGAAGG |
| 54 | BIP-hCFTR | GTGTTGATGTTATCCACCTTTTGTGGACTAGGAAAACAGATCAATAG |
| 55 | E3-hCFTR | TAATCCTGGAACTCCGGTGC |
| 56 | B3-hCFTR | TTTATGCCAATTAACATTTTGAC |
| 57 | rhLAMP Probe-hCFTR | F-CCTCCCTGTGGATgAGAGAGAAGG-Q |

DNA bases are uppercase; RNA bases are lowercase. F = 6-carboxyfluorescein; Q = IowaBlack™ FQ fluorescence quencher.

TABLE 15

Gen1 primer designs.

| SEQ ID NO.: | Name | Sequence |
|---|---|---|
| 58 | FIP-lambda | CAGCCAGCCGCAGCACGTTCGCTCATAGGAGATATGGTAGAGCCGCaGACAG-X |
| 59 | BIP-lambda | GAGAGAATTTGTACCACCTCCCACCGGGCACATAGCAGTCCTAGGGACAGTgGCGTT-X |
| 60 | E3-lambda | GGCTTGGCTCTGCTAACACGTTgCTCAA-X |
| 61 | B3-lambda | GGACGTTTGTAATGTCCGCTCCgGCACT-X |
| 62 | rhLAMP Probe-lambda | F-ACGTGCTGCGgCTGGCTGGT-Q |
| 63 | FIP-hCFTR | CCAAAGAGTAAAGTCCTTCTCTCTCGAGAGACTGTTGGCCCTTGAAGGaGAGCA-X |
| 64 | BIP-hCFTR | GTGTTGATGTTATCCACCTTTTGTGGACTAGGAAAACAGATCAATAGaTAAGC-X |
| 65 | E3-hCFTR | TAATCCTGGAACTCCGGTGCuAAGGT-X |
| 66 | B3-hCFTR | TTTATGCCAATTAACATTTTGACuTTATT-X |
| 67 | rhLAMP Probe-hCFTR | F-CCTCCCTGTGGATgAGAGAGAAGG-Q |

DNA bases are uppercase; RNA bases are lowercase. F = 6-carboxyfluorescein; Q = Iowa Black™ FQ fluorescence quencher. X = C3 spacer.

TABLE 16

GEN2 primer designs.

| SEQ ID NO.: | Name | Sequence |
|---|---|---|
| 68 | FTP-lambda | CAGCCAGCCGCAGCACGTTCGCTCATAGGAGATATGGTAGAGCCGCaG-X-X-AG |
| 69 | BIP-lambda | GAGAGAATTTGTACCACCTCCCACCGGGCACATAGCAGTCCTAGGGACAGTgG-X-X-TT |
| 70 | E3-lambda | GGCTTGGCTCTGCTAACACGTTgC-X-X-AA |
| 71 | B3-lambda | GGACGTTTGTAATGTCCGCTCCgG-X-X-CT |
| 72 | rhLAMP Probe-lambda | F-ACGTGCTGCGgCTGGCTGGT-Q |
| 73 | FTP-hCFTR | CCAAAGAGTAAAGTCCTTCTCTCTCGAGAGACTGTTGGCCCTTGAAGGaG-X-X-CA |
| 74 | BIP-hCFTR | GTGTTGATGTTATCCACCTTTTGTGGACTAGGAAAACAGATCAATAGaT-X-X-GC |
| 75 | E3-hCFTR | TAATCCTGGAACTCCGGTGCuA-X-X-GT |
| 76 | B3-hCFTR | TTTATGCCAATTAACATTTTGACuT-X-X-TT |
| 77 | rhLAMP Probe-hCFTR | F-CCTCCCTGTGGATgAGAGAGAAGG-Q |

DNA bases are uppercase; RNA bases are lowercase. F = 6-carboxyfluorescein; Q = Iowa Black™ FQ fluorescence quencher. X = C3 spacer Each assay could be performed as follows: The samples will either be Coriell gDNA or Lambda phage genomic DNA. Each assay condition could be run in triplicate with sample input of 5 ng Lambda phage genomic DNA or 20 ng human genomic DNA. For each assay, reactions could run using unmodified primers with intercalating dye (e.g., EvaGreen) and cleavable, blocked primers with an intercalating dye. For each assay, reactions will be run using zero, or titrated levels of RNase H2 (WT or hybrid RNase H2 proteins).

Each assay will be run in triplicate. Comparisons between the unmodified LAMP assays and the modified LAMP assays would be performed, by comparing the length of time required for formation of signal-generating products. It is expected that the hybrid RNase H2 proteins in the LAMP reactions will produce these products significantly later than the reactions containing conventional, wild-type RNase H2 proteins.

The 25 μL EvaGreen reaction mixtures will include:
12.5 μL of 2× Master Mix (1× is 20 mM Tris pH 8.8 @25° C., 10 mM KCl, 10 mM (NH$_4$)$_2$SO$_4$, 8 mM MgSO$_4$, 0.01% Tween-20, 1.4 mM dNTPs.)
1.6 μM FIP primer
1.6 μM BIP primer
1× EvaGreen dye
0.2 μM F3 primer
0.2 μM B3 primer
8 U BST DNA Polymerase (New England Biolabs: https://www.neb.com/products/m0275-bst-dna-polymerase-large-fragment)
1 μL of hybrid RNase H2 protein (for no RNase H2 control, buffer D will be used)
Nuclease Free Water to 25 uL
2 μL sample (either 10 ng/μL human gDNA or 2.5 ng/uL lambda genomic DNA)

Example 7. Q48R SEL29 RNase 112 Improves the Quality of NGS Libraries Compared to Wild Type P.a. RNase 112 in a Multiplex rhPCR Amplicon Sequencing Workflow Using a 177-Plex Assay Panel A modified rhAmpSeq protocol was adapted for low frequency variant detection. This protocol uses both a high-fidelity DNA polymerase to reduce amplification errors and unique molecular identifiers (UMIs) for error correction. Q48R SEL29 RNase H2 was compared to wild type P.a. RNase H2 in this system to determine if dimer formation is reduced.

There are two PCR cycling steps with a SPRI (Solid Phase Reversible Immobilization, Beckman Coulter Life sciences, Indianapolis, IN) cleanup following each step. The purpose of the first PCR step (PCR 1) is to incorporate a 6-nucleotide degenerate UMI on each side of the target amplicons. This step also includes the use of 3'-blocked primers and requires RNase H2 to cleave off the blocker and allow a high-fidelity DNA polymerase to extend and amplify each target. The target-specific assay panel contains 177 proprietary primer pairs, and results in approximately 20% of the total reads being primer dimer when wild type P.a. RNase H2 is present in PCR1. his panel generates a large amount of primer dimers, making it optimal for testing Q48R SEL29 RNase H2.

Various 10× titrations of Q48R SEL29 RNase H2 and wild type P.a. RNase H2 (87.5 mU/uL, 175 mU/uL, and 350 mU/uL), were prepared in RNase H2 storage buffer (Integrated DNA technologies, Coralville, IA). Each PCR 1 reaction was 20 μL final volume and contained 10 nM (200 fmol) of each forward and reverse primer, 0.03 U/μL Phusion Hot Start II DNA Polymerase (Thermo Fisher Scientific, Waltham, MA), 20 ng of genomic cell line DNA (cell line NA24385, Coriell Institute for Medical Research, Camden, NJ), and 1× final concentration of RNase H2 in a proprietary high-fidelity polymerase buffer. Thermal cycling was performed on a T100 Thermal Cycler (Bio-Rad®, Hercules, CA) with the cycling conditions listed in Table 17. PCR1 thermal cycling was promptly followed by SPRI cleanup. 1.25× (25 μL) of AMPure magnetic beads (Beckman Coulter Life Sciences, Indianapolis, IN) were added to each well and mixed thoroughly. Plates were incubated at room temperature for 5 minutes on the benchtop followed by 5 minutes on a magnet. The supernatant was discarded and libraries were washed twice with 80% ethanol. Samples were eluted in 22 μL of IDTE pH 7.5 (IDT, Coralville, IA). 20 μL of eluted product was carried forward as input for PCR2.

TABLE 17

PCR 1 cycling conditions.

| | Cycles | Temperature (° C.) | Time |
| --- | --- | --- | --- |
| Enzyme activation | 1 | 95° C. | 10 min |
| Amplification | 2 | 95° C. | 15 secs |
| | | 60° C. | 12 min |
| Hold | 1 | 4° C. | ∞ Hold |

The purpose of the second PCR step (PCR 2) was to amplify PCR 1 product and add unique sample index sequences for pooling and sequencing purposes. PCR 2 does not require the use of RNase H2. PCR 2 reactions were performed at 50 μL final volume. A 2× version of the high-fidelity polymerase buffer used in PCR 1 was added to each eluted sample from PCR 1 for a final 1× concentration. Each reaction also had a unique combination of i5 and i7 rhAmpSeq index primers (IDT) at 500 nM each. Thermal cycling was performed on T100 Thermal Cycler (Bio-Rad®, Hercules, CA) with the cycling conditions listed in Table 18. SPRI cleanup immediately followed PCR 2 and is identical as the methods listed above, except for AMPure bead concentrations, which were used at 0.9× after PCR 2. Samples were eluted in 22 μL of IDTE pH 7.5 (IDT, Coralville, IA). 20 μL of eluted product was taken and stored at −20° C. until sequencing.

TABLE 18

PCR 2 cycling Conditions.

| | Cycles | Temperature (° C.) | Time |
| --- | --- | --- | --- |
| Enzyme activation | 1 | 95° C. | 30 secs |
| Amplification | 22 | 95° C. | 15 secs |
| | | 60° C. | 30 secs |
| | | 72° C. | 30 secs |
| Final extension | 1 | 72° C. | 1 min |
| Hold | 1 | 4° C. | ∞ Hold |

The resulting libraries were pooled at equal volume for sequencing (5 uL). This pool was quantified using the Qubit dsDNA HS Assay kit (Thermo Fisher), and diluted to 4 nM final concentration. An equal amount of library pool was combined with 0.2 N NaOH to denature libraries. This reaction was subsequently diluted to a final concentration of 8 μM containing 2.5% PhiX (Illumina, San Diego, CA) spike-in. This reaction was loaded onto a MiSeq 300 cycle kit (Illumina, San Diego, CA) and run (Cluster density: 1002±34; Q30: 93.13%). Results were run through the internal proprietary IDT rhAmpSeq VII bioinformatics analysis pipeline.

For the purposes of this disclosure, calculations and terms relating to results below are listed here. The amount of primer dimer produced during amplification of sequencing libraries is defined by the dimer rate. The rhAmpSeq VII pipeline calculates this by taking the overall counts of dimer identified and dividing by the number of QC passed reads (total number of reads that passed a chastity filter). Mapping rate is calculated by taking the total number of mapped reads and dividing by the QC passed reads. On target rate is calculated by taking the total number of on-target reads and dividing by the QC passed reads. Overall amplicon uniformity, or amplicon uniformity ≥0.2×, is calculated as the percent of normal amplicons that have greater than or equal to 0.2 times the amplicon mean coverage. The dropout rate, or uniformity ≤0.05×, is calculated as the percent of normal amplicons with less than 0.05 times the amplicon mean coverage. The amplicon uniformity distribution compares each amplicon's coverage relative to the mean amplicon coverage for a given sample, and plots in the following ranges: 0.1-0.2×, 0.2-0.5×, 0.5-1.5×, 1.5-2.5×, and 2.5-5×.

The rhAmpSeq VII pipeline also identifies the primers contributing to the formation of each primer dimer. The normalized dimer count reflects the percentage that each primer dimer contributes to the total Dimer Rate and is calculated using the following formula:

$$\text{Normalized Dimer Count} = \frac{\text{Dimer Weight} * \text{Total Dimer Reads per Sample}}{\text{Total Reads per Sample}}$$

For all concentrations tested, Q48R SEL29 RNase H2 reduced the dimer rate compared to wild type P.a. RNase H2, and also increased mapping rate and on-target rate. At the lowest concentration (8.75 mU/μL) Q48R SEL29 RNase H2 generated libraries with 4% dimer, compared to the control wild type P.a. RNase H2 which generated 11% dimer (FIG. 1, panel A).

The mapping rate and on target rate for libraries produced with the lowest concentration of Q48R SEL29 RNase H2 (8.75 mU/μL) is increased to 96% compared to 88% for wild type P.a. RNase H2 (FIG. 1, panels B and C).

Figure 2:
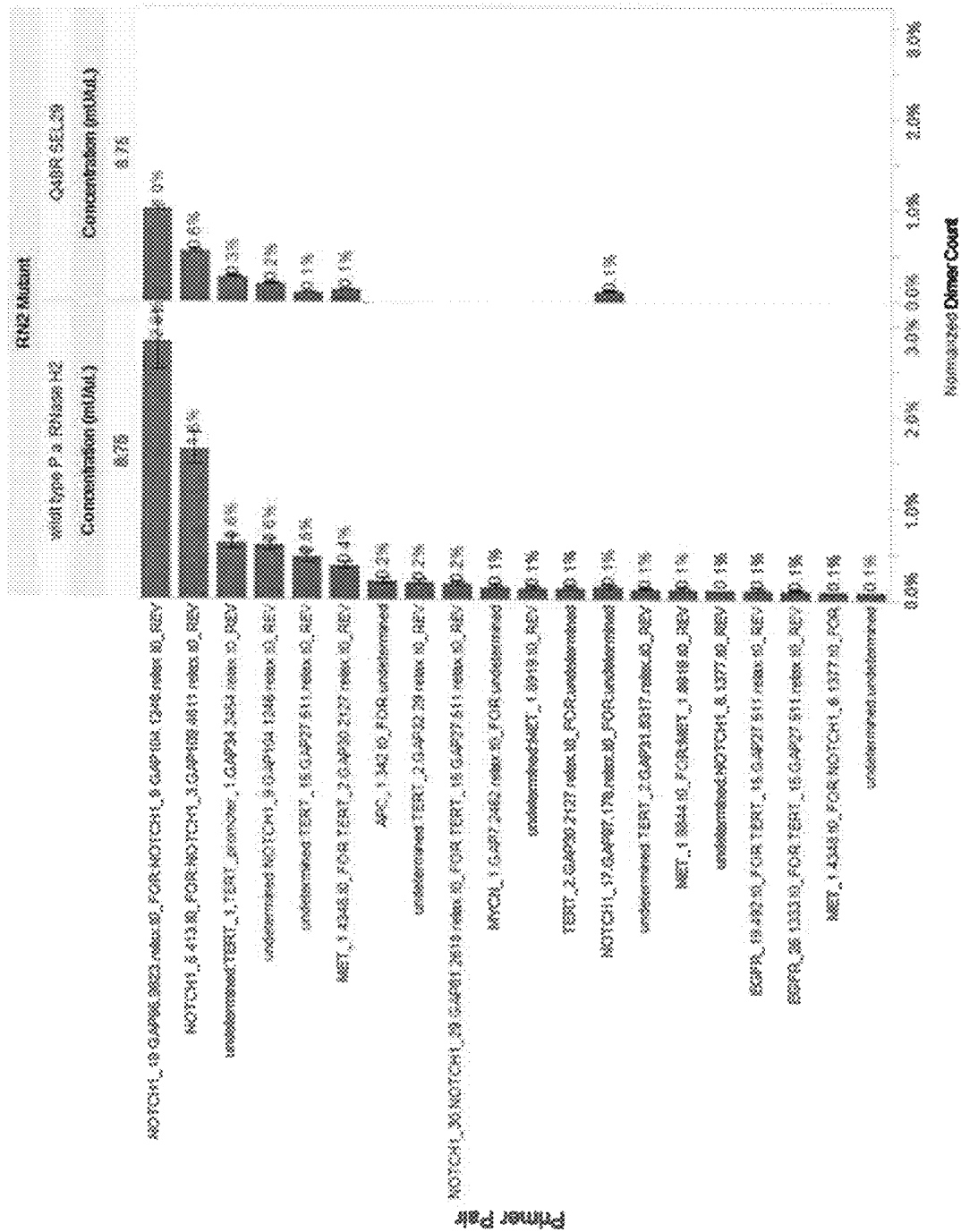
FIG. 2 depicts examples of mean normalized dimer count for per each primer pair identified, wherein the mutant Q48R SEL29 RNase H2 enzyme reduces most primer dimers identified by half compared to wild type P.a. RNase H2 enzyme.

The dimer rate can be broken down into individual primer dimers produced, then normalized to determine each primer dimer's contribution to the overall dimer rate as described above (normalized dimer count). Q48R SEL29 RNase H2 reduces the amount of most primer dimers in half. For example, in libraries generated with the lowest concentration of Q48R Mut 29 RNase H2 (8.75 mU/μL) the top dimer identified in all sample libraries (NOTCH1_19.GAP95.9623.relax.t0_FOR: NOTCH1_9.GAP104.1246.relax.t0_REV) only makes up 1.23% of the overall dimer rate compared to wild type P.a. RNase H2 with 2.83%. Some dimers are reduced by more than half in the case of undetermined: TERT_15.GAP27.511.relax.t0_REV Q48R SEL29 RNase H2 libraries generate 75% less dimer at 0.11% compared to wild type P.a. RNase H2 where this dimer contributes 0.47% to the overall Dimer Rate (Table 19 and FIG. 2).

TABLE 19

Normalized Dimer Count per primer pair identified described in Example 1.

| Primer Pair | Wild type P.a. RNase H2 8.75 mU/ μL RN2 | Q48R SEL29 RNase H2 8.75 mU/ μL RN2 |
|---|---|---|
| NOTCH1_19.GAP95.9623.relax.t0_FOR: NOTCH1_9.GAP104.1246.relax.t0_REV | 2.83% | 1.23% |
| NOTCH1_5.413.t0_FOR: NOTCH1_3.GAP109.4611.relax.t0_REV | 1.65% | 0.63% |
| undetermined: TERT_1, | 0.63% | 0.32% |

TABLE 19-continued

Normalized Dimer Count per primer pair identified described in Example 1.

| Primer Pair | Wild type P.a. RNase H2 8.75 mU/ μL RN2 | Q48R SEL29 RNase H2 8.75 mU/ μL RN2 |
|---|---|---|
| TERT_promoter_1.GAP34.2454.relax.t0_REV undetermined: TERT_15.GAP27.511.relax.t0_REV | 0.47% | 0.11% |
| undetermined: NOTCH1_9.GAP104.1246.relax.t0_REV MET_1.4348.t0_FOR: TERT_2.GAP30.2127.relax.t0_REV | 0.61% | 0.29% |
| | 0.38% | 0.16% |
| APC_1.342.t0_FOR: undetermined | 0.21% | not detected |
| undetermined: TERT_2.GAP32.29.relax.t0_REV | 0.20% | 0.07% |
| NOTCH1_30, NOTCH1_29.GAP81.2618.relax.t0_FOR TERT_15.GAP27.511.relax.t0_REV | 0.18% | 0.03% |
| undetermined: MET_1.8919.t0_REV | 0.12% | 0.06% |
| TERT_2.GAP30.2127.relax.t0_FOR: undetermined | 0.13% | 0.06% |
| MYCN_1.GAP7.2462.relax.t0_FOR: undetermined | 0.13% | 0.05% |
| EGFR_19.492.t0_FOR: TERT_15.GAP27.511.relax.t0_REV | 0.10% | not detected |
| EGFR_25.1333.t0_FOR: TERT_15.GAP27.511.relax.t0_REV | 0.10% | not detected |
| NOTCH1_17.GAP97.178.relax.t0_FOR: undetermined | 0.13% | 0.15% |
| TERT_7.69.t0_FOR: MYC_2.884.t0_REV | 0.07% | 0.07% |
| NOTCH1_34.GAP74.1722.relax.t0_FOR: undetermined | 0.07% | 0.03% |
| MET_1.9844.t0_FOR: MET_1.8919.t0_REV | 0.12% | 0.08% |
| MET_1.4348.t0_FOR: NOTCH1_6.1377.t0_FOR | 0.09% | 0.04% |
| TERT_7.69.t0_FOR: MYCL_2.GAP2.2394.relax.t0_REV | not detected | 0.06% |
| undetermined: NOTCH1_12,NOTCH1_11.207.t0_REV | not detected | 0.03% |
| NOTCH1_19.GAP95.9623.relax.t0_FOR: NOTCH1_2.45.t0_REV | 0.06% | 0.05% |
| DNMT3B_15.337.t0_REV: DNMT3B_15.337.t0_REV | not detected | 0.06% |
| MAP3K1_1.GAP39.5178.relax.t0_FOR: TERT_2.GAP33.6839.relax.t0_REV | not detected | 0.06% |
| TERT_1, TERT_promoter_1.GAP34.14490.relax.t0_FOR: undetermined | not detected | 0.05% |
| TERT_5.GAP29.1338.relax.t0_FOR: undetermined | not detected | 0.07% |
| undetermined: NOTCH1_6.1377.t0_REV | 0.09% | 0.10% |
| undetermined: NOTCH1_8.381.t0_REV | not detected | 0.06% |
| undetermined: NOTCH1_22.GAP94.2342.relax.t0_REV | not detected | 0.09% |
| undetermined: TERT_2.GAP31.8317.relax.t0_REV | 0.10% | 0.13% |
| undetermined: undetermined | 0.10% | 0.04% |

Figure 3:
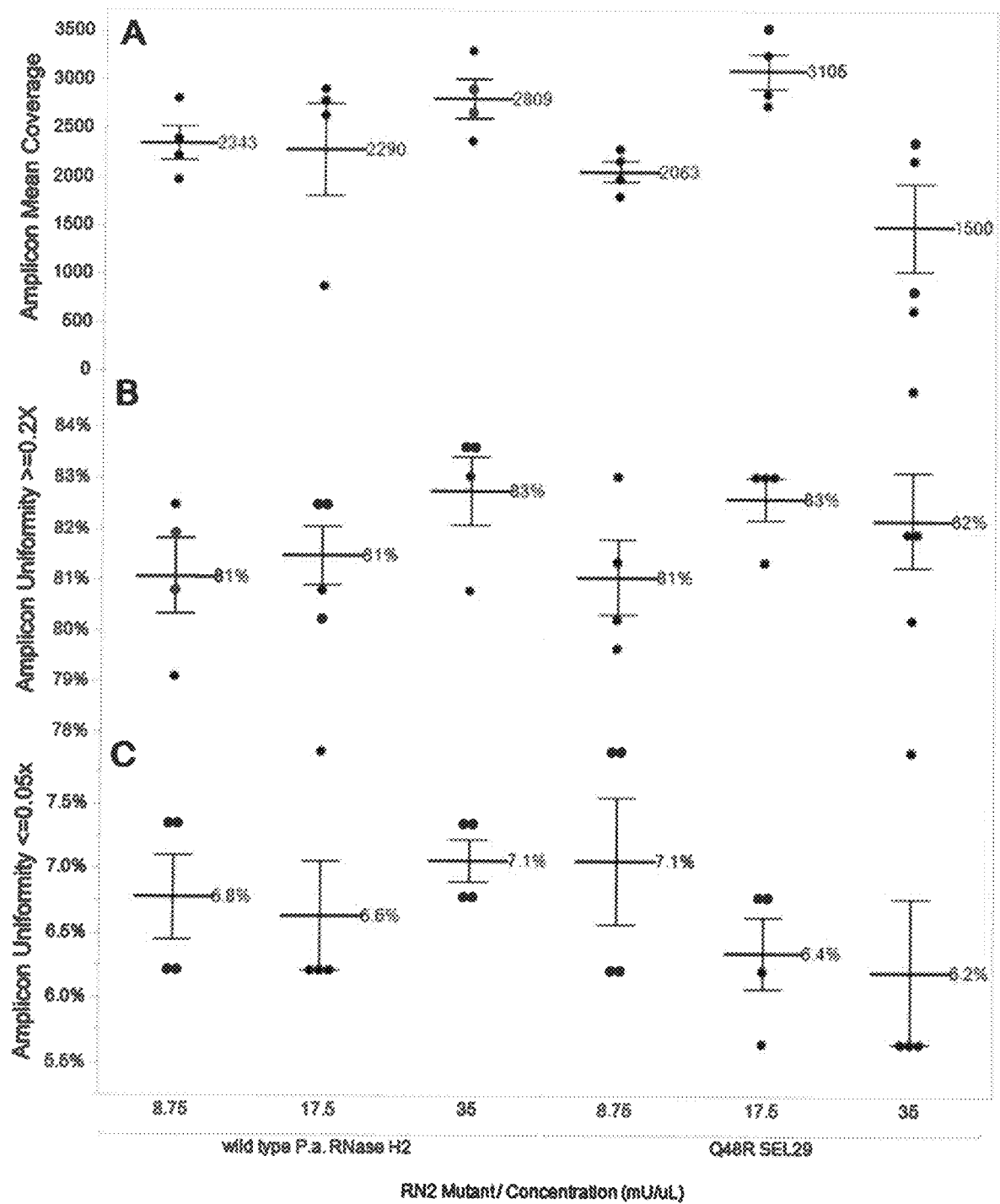
FIG. 3 depicts exemplary data Amplicon Uniformity ≥0.2× and Amplicon Uniformity ≤0.05× (Dropout Rate), wherein the yield of libraries is comparable at all concentrations between the mutant Q48R SEL29 RNase H2 enzyme and the wild type P.a. RNase H2 enzyme (panel A); the overall amplicon uniformity ≥0.2× of mutant Q48R SEL29 RNase H2 enzyme being comparable to wild type P.a. RNase H2 enzyme at the various concentrations tested (panel B); and amplicon drop out rates being similar in all titration concentrations tested between the mutant Q48R SEL29 RNase H2 enzyme and wild type P.a. RNase H2 enzyme (panel C).
Figure 4:
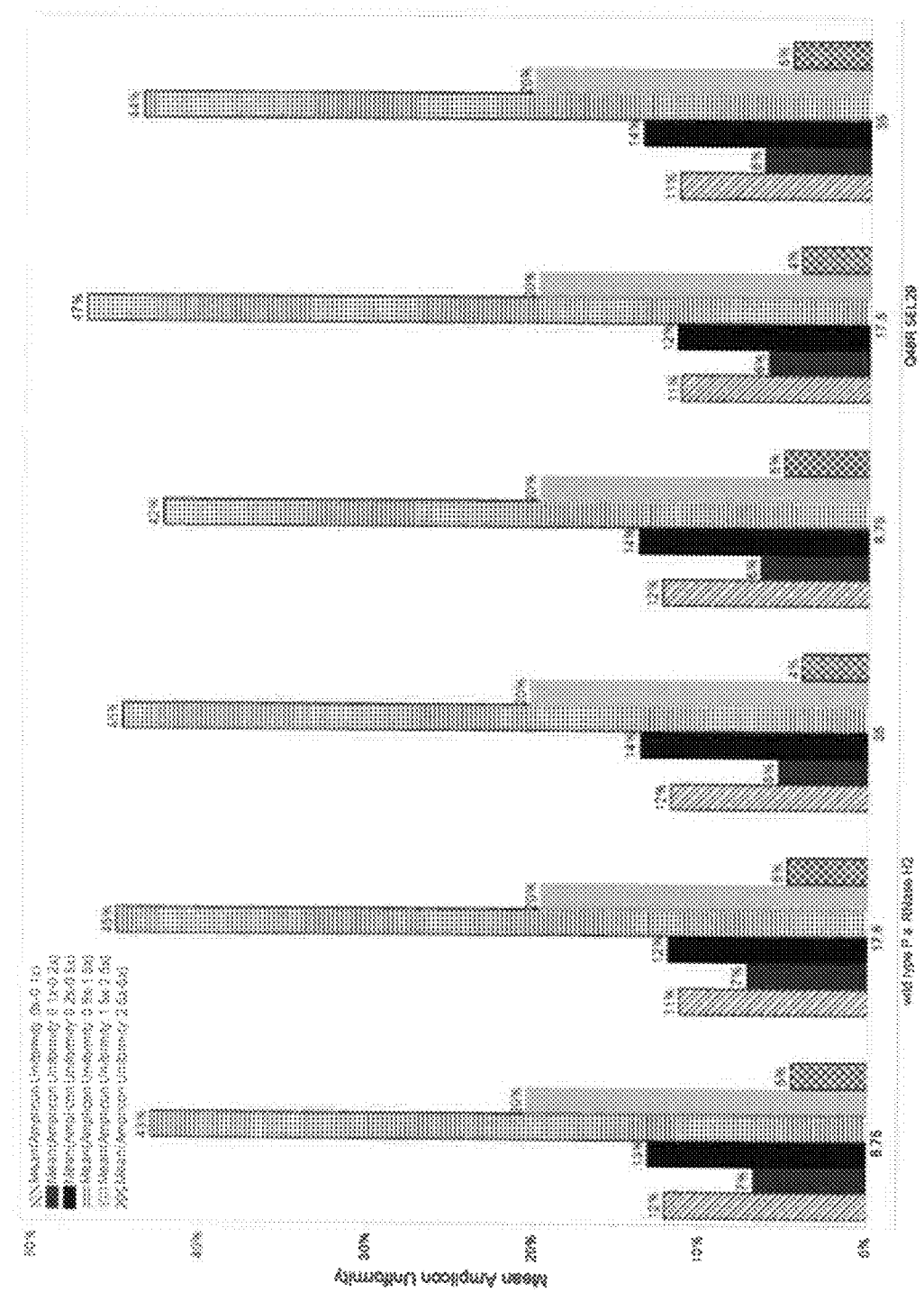
FIG. 4 depicts exemplary data showing uniformity distribution (percent of amplicons that have coverage in ranges 0-0.1×, 0.1-0.2×, 0.2×-0.5×, 0.5×-1.5×, 1.5×-2.5×, and 2.5-5× compared to the amplicon mean coverage) being comparable between the mutant Q48R SEL29 RNase H2 enzyme and the wild type P.a. RNase H2 enzyme.

The ability of Q48R SEL29 RNase H2 to reduce the dimer rate does not impact the library yield, overall uniformity and dropout rates, or uniformity distribution metrics. Q48R SEL29 RNase H2 generates similar library yields with all titration concentrations tested compared to the wild type P.a. RNase H2 enzymes as demonstrated by the amplicon mean coverage (FIG. 3, panel A). In addition, the overall amplicon uniformity ≥0.2× and amplicon dropout rates (amplicon uniformity ≤0.05×) are comparable in all titration concentrations tested between the Q48R SEL29 RNase H2 and the wild type P.a. enzyme (FIG. 3, panels B and C). Further, the uniformity distribution between Q48R SEL29 and wild type P.a. RNase H2 appears similar (FIG. 4). Q48R SEL29 RNase H2 reduces primer dimer formation compared to standard wild-type P.a. RNase H2 during library generation in a rhAmpseq workflow without altering other important sequencing metrics.

Together, these data show that Q48R SEL29 RNase H2 improves generation of multiplex next generation sequencing libraries using a high-fidelity DNA polymerase in a high-fidelity buffer.

Example 8. Exemplary Amino Acid and Nucleic Acid Sequences Encoding RNase 112 Proteins Exemplary amino acid and nucleic acid sequences encoding RNase H2 proteins are presented below.

TABLE 20

Nucleic acid sequences encoding RNase H2 proteins previously described.

| Mut ID # | SEQ ID NO.: | Specific AA changes | Sequence[1] |
|---|---|---|---|
| N/A | 78 | WT P.a. RNase H2 | ATGAAAGTTGCAGGTGCAGATGAAGCTGGTC GTGGTCCAGTTATTGGTCCGCTGGTTATTGTT GCTGCTGTTGTGGAGGAAGACAAAATCCGCT CTCTGACTAAGCTGGGTGTTAAAGACTCCAAA CAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGAAGTTATTTACATTGATT CCGCTGATGTTAAAGCTGAACGTTTCGCTGAA AACATTCGCAGCCGTCTGGCGTACGAAGCGA AAGTTGTAGCCGAACATAAAGCGGATGCGAA GTATGAGATCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAAGAAATGG CTGGAAGAATGGTATAGCAAACACGGCAATT TCCCGCCGATCGTGCGTCGTACTTGGGATACT GCAAAGAAAATCGAAGAAAAATTCAAACGTG CGCAGCTGACCCTGGACAACTTCCTGAAGCGT TTTCGCAACAAGCTTGCGGCCGCACTCGAGATC AAACGGGCTAGCCAGCCAGAACTCGCCCCGGAA GACCCCGAGGATGTCGAGCACCACCACCACCAC CACTGA |
| 1 | 79 | SEL28 RNase H2 | ATGAAAGTTGCAGGTGCAGATGAAGCTGGTC GTGGTCCAGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGG AAGTTGTAGCCAAACATAAAGCGGATGACAT CTTTCCGGTCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAAGAAATGG CTGGAAGAATGGTATAGCAAACACGGCAATT TCCCGCCGATCGTGCGTCGTACTTGGGATACT GCAAAGAAAATCGAAGAAAAATTCAAACGTG CGCAGCTGACCCTGGACAAGTTCTTCAAGAA |

TABLE 20-continued

Nucleic acid sequences encoding RNase H2 proteins previously described.

| Mut ID # | SEQ ID NO.: | Specific AA changes | Sequence[1] |
|---|---|---|---|
| | | | ACCTAAGCTTGCGGCCGCACTCGAGATCAAACG GGCTAGCCAGCCAGAACTCGCCCCGGAAGACCC CGAGGATGTCGAGCACCACCACCACCACCACTG A |
| 2 | 80 | SEL29 RNase H2 | ATGAAAGTTGCAGGTATAGATGAAGCTGGTC GTGGTCCAGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGA AAGTTGTAGCCGAACATAAAGCGGATGCGAA GTATGAGATCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAGGGCATTC CTGGAAAATTACTATAGAGAACACGGCGAAT TCCCGCCGATCGTGCGTAAAGGTTGGAAGACT CTAAAGAAAATCGCAGAAAAAGTCGAAAGTG AGAAGAAGGCTGAGGAACGGCAGGCGACCCT GGACAGGTACTTCAGGAAGGTTAAGCTTGCGG CCGCACTCGAGATCAAACGGGCTAGCCAGCCAG AACTCGCCCCGGAAGACCCCGAGGATGTCGAGC ACCACCACCACCACTGA |
| 3 | 81 | P13S SEL28 RNase H2 | ATGAAAGTTGCAGGTGCAGATGAAGCTGGTC GTGGTTCTGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGG AAGTTGTAGCCAAACATAAAGCGGATGACAT CTTTCCGGTCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAAGAAATGG CTGGAAGAATGGTATAGCAAACACGGCAATT TCCCGCCGATCGTGCGTCGTACTTGGGATACT GCAAAGAAAATCGAAGAAAAATTCAAACGTG CGCAGCTGACCCTGGACAAGTTCTTCAAGAA ACCTAAGCTTGCGGCCGCACTCGAGATCAAACG GGCTAGCCAGCCAGAACTCGCCCCGGAAGACCC CGAGGATGTCGAGCACCACCACCACCACCACTG A |
| 4 | 82 | A107V SEL28 RNase H2 | ATGAAAGTTGCAGGTGCAGATGAAGCTGGTC GTGGTCCAGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGTAGAT GCCGCTGATGTTGATGAAGAACGTTTCGCTAG AGAGCTTGGCGAGCGTCTGAACTTCGAAGCG GAAGTTGTAGCCAAACATAAAGCGGATGACA TCTTTCCGGTCGTATCCGCAGCCTCTATCCTG GCAAAAGTTATCCGTGACCGCGAGATCGAAA AGCTGAAAGCCGAATACGGTGATTTTGGTTCC |

TABLE 20-continued

Nucleic acid sequences encoding RNase H2 proteins previously described.

| Mut ID # | SEQ ID NO.: | Specific AA changes | Sequence[1] |
|---|---|---|---|
| | | | GGTTACCCGTCTGATCCGCGTACTAAGAAATG GCTGGAAGAATGGTATAGCAAACACGGCAAT TTCCCGCCGATCGTGCGTCGTACTTGGGATAC TGCAAAGAAAATCGAAGAAAAATTCAAACGT GCGCAGCTGACCCTGGACAAGTTCTTCAAGA AACCT*AAGCTTGCGGCCGCACTCGAGATCAAAC GGGCTAGCCAGCCAGAACTCGCCCCGGAAGACC CCGAGGATGTCGAGCACCACCACCACCACCACT GA* |
| 5 | 83 | P13S/ A107V SEL28 RNase H2 | ATGAAAGTTGCAGGTGCAGATGAAGCTGGTC GTGGTTCTGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGTAGAT GCCGCTGATGTTGATGAAGAACGTTTCGCTAG AGAGCTTGGCGAGCGTCTGAACTTCGAAGCG GAAGTTGTAGCCAAACATAAAGCGGATGACA TCTTTCCGGTCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAAGAAATG GCTGGAAGAATGGTATAGCAAACACGGCAAT TTCCCGCCGATCGTGCGTCGTACTTGGGATAC TGCAAAGAAAATCGAAGAAAAATTCAAACGT GCGCAGCTGACCCTGGACAAGTTCTTCAAGA AACCT*AAGCTTGCGGCCGCACTCGAGATCAAAC GGGCTAGCCAGCCAGAACTCGCCCCGGAAGACC CCGAGGATGTCGAGCACCACCACCACCACCACT GA* |
| 6 | 84 | P13S SEL29 RNase H2 | ATGAAAGTTGCAGGTATAGATGAAGCTGGTC GTGGTTCTGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGA AGTTGTAGCCGAACATAAAGCGGATGCAA GTATGAGATCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAGGGCATTC CTGGAAAATTACTATAGAGAACACGGCAATT CCCGCCGATCGTGCGTAAAGGTTGGAAGACT CTAAAGAAAATCGCAGAAAAAGTCGAAAGTG AGAAGAAGGCTGAGGAACGGCAGGCGACCCT GGACAGGTACTTCAGGAAGGTT*AAGCTTGCGG CCGCACTCGAGATCAAACGGGCTAGCCAGCCAG AACTCGCCCCGGAAGACCCCGAGGATGTCGAGC ACCACCACCACCACCACTGA* |
| 7 | 85 | Q48R SEL29 RNase H2 | ATGAAAGTTGCAGGTATAGATGAAGCTGGTC GTGGTCCAGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCCCGCCGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA |

TABLE 20-continued

Nucleic acid sequences encoding RNase H2 proteins previously described.

| Mut ID # | SEQ ID NO.: | Specific AA changes | Sequence[1] |
|---|---|---|---|
| | | | GAGCTTGGCGAGCGTCTGAACTTCGAAGCGA AAGTTGTAGCCGAACATAAAGCGGATGCGAA GTATGAGATCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAGGGCATTC CTGGAAAATTACTATAGAGAACACGGCAATT CCCGCCGATCGTGCGTAAAGGTTGGAAGACT CTAAAGAAAATCGCAGAAAAAGTCGAAAGTG AGAAGAAGGCTGAGGAACGGCAGGCGACCCT GGACAGGTACTTCAGGAAGGTT*AAGCTTGCGG CCGCACTCGAGATCAAACGGGCTAGCCAGCCAG AACTCGCCCCGGAAGACCCCGAGGATGTCGAGC ACCACCACCACCACCACTGA* |
| 8 | 86 | A107V SEL29 RNase H2 | ATGAAAGTTGCAGGTATAGATGAAGCTGGTC GTGGTCCAGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGTAGATGTTGATGAAGAACGTTTCGCTAG AGAGCTTGGCGAGCGTCTGAACTTCGAAGCG AAAGTTGTAGCCGAACATAAAGCGGATGCGAA AGTATGAGATCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAGGGCATT CCTGGAAAATTACTATAGAGAACACGGCGAA TTCCCGCCGATCGTGCGTAAAGGTTGGAAGAC TCTAAAGAAAATCGCAGAAAAAGTCGAAAGT GAGAAGAAGGCTGAGGAACGGCAGGCGACCC TGGACAGGTACTTCAGGAAGGTT*AAGCTTGCG GCCGCACTCGAGATCAAACGGGCTAGCCAGCCA GAACTCGCCCCGGAAGACCCCGAGGATGTCGAG CACCACCACCACCACCACTGA* |
| 9 | 87 | P13S/ A107V SEL29 RNase H2 | ATGAAAGTTGCAGGTATAGATGAAGCTGGTC GTGGTTCTGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGTAGATGTTGATGAAGAACGTTTCGCTAG AGAGCTTGGCGAGCGTCTGAACTTCGAAGCG AAAGTTGTAGCCGAACATAAAGCGGATGCGA AGTATGAGATCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAGGGCATT CCTGGAAAATTACTATAGAGAACACGGCGAA TTCCCGCCGATCGTGCGTAAAGGTTGGAAGAC TCTAAAGAAAATCGCAGAAAAAGTCGAAAGT GAGAAGAAGGCTGAGGAACGGCAGGCGACCC TGGACAGGTACTTCAGGAAGGTT*AAGCTTGCG GCCGCACTCGAGATCAAACGGGCTAGCCAGCCA GAACTCGCCCCGGAAGACCCCGAGGATGTCGAG CACCACCACCACCACCACTGA* |

[1]Location of mutations are shown in bold and underlined. Plasmid extension and (His)$_6$-tag is shown in italics, including the stop codon.

TABLE 21

Amino acid sequences for the RNase H2 proteins lacking C-terminal extension sequences.

| SEQ ID NO.: | Specific AA changes | Sequence[1] |
|---|---|---|
| 88 | P13S SEL28 RNase H2 | MKVAGADEAGRGSVIGPLVIVAAVVDENS LPKLEELKVRDSKKLTPKRREKLFDEIVKV LDDYSVVIVSPQDIDGRKGSMNELEVENFV KALNSLKVKPDVIYADAADVDEERFAREL GERLNFEAEVVAKHKADDIFPVVSAASILA KVIRDREIEKLKAEYGDFGSGYPSDPRTKK WLEEWYSKHGNFPPIVRRTWDTAKKIEEK FKRAQLTLDKFFKKP |
| 89 | A107V SEL28 RNase H2 | MKVAGADEAGRGPVIGPLVIVAAVVDENS LPKLEELKVRDSKKLTPKRREKLFDEIVKV LDDYSVVIVSPQDIDGRKGSMNELEVENFV KALNSLKVKPDVIYADAVDVDEERFAREL GERLNFEAEVVAKHKADDIFPVVSAASILA KVIRDREIEKLKAEYGDFGSGYPSDPRTKK WLEEWYSKHGNFPPIVRRTWDTAKKIEEK FKRAQLTLDKFFKKP |
| 90 | P13S/A107V SEL28 RNase H2 | MKVAGADEAGRGSVIGPLVIVAAVVDENS LPKLEELKVRDSKKLTPKRREKLFDEIVKV LDDYSVVIVSPQDIDGRKGSMNELEVENFV KALNSLKVKPDVIYADAVDVDEERFAREL GERLNFEAEVVAKHKADDIFPVVSAASILA KVIRDREIEKLKAEYGDFGSGYPSDPRTKK WLEEWYSKHGNFPPIVRRTWDTAKKIEEK FKRAQLTLDKFFKKP |
| 91 | P13S SEL29 RNase H2 | MKVAGIDEAGRGSAIGPLVIVAAVVDENSL PKLEELKVRDSKKLTPAQREKLFDEIVKVL DDYSVVIVSPQDIDGRKGSMNELEVENFVK ALNSLKVKPDVIYADAADVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV |
| 92 | Q48R SEL29 RNase H2 | MKVAGIDEAGRGPAIGPLVIVAAVVDENSL PKLEELKVRDSKKLTPARREKLFDEIVKVL DDYSVVIVSPQDIDGRKGSMNELEVENFVK ALNSLKVKPDVIYADAADVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV |
| 93 | A107V SEL29 RNase H2 | MKVAGIDEAGRGPAIGPLVIVAAVVDENSL PKLEELKVRDSKKLTPAQREKLFDEIVKVL DDYSVVIVSPQDIDGRKGSMNELEVENFVK ALNSLKVKPDVIYADAVDVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV |
| 94 | P13S/A107V SEL29 RNase H2 | MKVAGIDEAGRGSAIGPLVIVAAVVDENSL PKLEELKVRDSKKLTPAQREKLFDEIVKVL DDYSVVIVSPQDIDGRKGSMNELEVENFVK ALNSLKVKPDVIYADAVDVDEERFARELG ERLNFEAKVVAEHKADAKYEIVSAASILAK VIRDREIEKLKAEYGDFGSGYPSDPRTRAFL ENYYREHGEFPPIVRKGWKTLKKIAEKVES EKKAEERQATLDRYFRKV |

[1]Location of mutations are shown in bold and underlined.

TABLE 22

Nucleic acid sequences encoding RNase H2 proteins lacking additional C-terminal extension sequences.

| SEQ ID NO.: | Specific AA changes | Sequence[1] |
|---|---|---|
| 95 | P13S SEL28 RNase H2 | ATGAAAGTTGCAGGTGCAGATGAAGCTGGTC GTGGTTCTGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGG AAGTTGTAGCCAAACATAAAGCGGATGACAT CTTTCCGGTCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAAGAAATGG CTGGAAGAATGGTATAGCAAACACGGCAATT TCCCGCCGATCGTGCGTCGTACTTGGGATACT GCAAAGAAAATCGAAGAAAAATTCAAACGTG CGCAGCTGACCCTGGACAAGTTCTTCAAGAA ACCTTGA |
| 96 | A107V SEL28 RNase H2 | ATGAAAGTTGCAGGTGCAGATGAAGCTGGTC GTGGTCCAGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGTAGAT GCCGCTGATGTTGATGAAGAACGTTTCGCTAG AGAGCTTGGCGAGCGTCTGAACTTCGAAGCG GAAGTTGTAGCCAAACATAAAGCGGATGACA TCTTTCCGGTCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAAGAAATG GCTGGAAGAATGGTATAGCAAACACGGCAAT TTCCCGCCGATCGTGCGTCGTACTTGGGATAC TGCAAAGAAAATCGAAGAAAAATTCAAACGT GCGCAGCTGACCCTGGACAAGTTCTTCAAGA AACCTTGA |
| 97 | P13S/A107V SEL28 RNase H2 | ATGAAAGTTGCAGGTGCAGATGAAGCTGGTC GTGGTTCTGTTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGAAGCGACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGTAGAT GCCGCTGATGTTGATGAAGAACGTTTCGCTAG AGAGCTTGGCGAGCGTCTGAACTTCGAAGCG GAAGTTGTAGCCAAACATAAAGCGGATGACA TCTTTCCGGTCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAAGAAATG GCTGGAAGAATGGTATAGCAAACACGGCAAT TTCCCGCCGATCGTGCGTCGTACTTGGGATAC TGCAAAGAAAATCGAAGAAAAATTCAAACGT GCGCAGCTGACCCTGGACAAGTTCTTCAAGA AACCTTGA |
| 98 | P13S SEL29 RNase H2 | ATGAAAGTTGCAGGTATAGATGAAGCTGGTC GTGGTTCTGCTATTGGTCCGCTGGTTATTGTT GCTGCTGTTGTGGATGAAAACAGTCTCCCCAA GCTGGAAGAGCTGAAAGTTAGAGACTCCAAA |

TABLE 22-continued

Nucleic acid sequences encoding RNase H2 proteins lacking additional C-terminal extension sequences.

| SEQ ID NO.: | Specific AA changes | Sequence[1] |
|---|---|---|
| | | AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGA AAGTTGTAGCCGAACATAAAGCGGATGCGAA GTATGAGATCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAGGGCATTC CTGGAAAATTACTATAGAGAACACGGCGAAT TCCCGCCGATCGTGCGTAAAGGTTGGAAGACT CTAAAGAAAATCGCAGAAAAAGTCGAAAGTG AGAAGAAGGCTGAGGAACGGCAGGCGACCCT GGACAGGTACTTCAGGAAGGTT*TGA* |
| 99 | Q48R SEL29 RNase H2 | ATGAAAGTTGCAGGTATAGATGAAGCTGGTC GTGGTCCAGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCCGCCGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGCTGATGTTGATGAAGAACGTTTCGCTAGA GAGCTTGGCGAGCGTCTGAACTTCGAAGCGA AAGTTGTAGCCGAACATAAAGCGGATGCGAA GTATGAGATCGTATCCGCAGCCTCTATCCTGG CAAAAGTTATCCGTGACCGCGAGATCGAAAA GCTGAAAGCCGAATACGGTGATTTTGGTTCCG GTTACCCGTCTGATCCGCGTACTAGGGCATTC CTGGAAAATTACTATAGAGAACACGGCGAAT TCCCGCCGATCGTGCGTAAAGGTTGGAAGACT CTAAAGAAAATCGCAGAAAAAGTCGAAAGTG AGAAGAAGGCTGAGGAACGGCAGGCGACCCT GGACAGGTACTTCAGGAAGGTT*TGA* |
| 100 | A107V SEL29 RNase H2 | ATGAAAGTTGCAGGTATAGATGAAGCTGGTC GTGGTCCAGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGTAGATGTTGATGAAGAACGTTTCGCTAG AGAGCTTGGCGAGCGTCTGAACTTCGAAGCG AAAGTTGTAGCCGAACATAAAGCGGATGCGA AGTATGAGATCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAGGGCATT CCTGGAAAATTACTATAGAGAACACGGCGAA TTCCCGCCGATCGTGCGTAAAGGTTGGAAGAC TCTAAAGAAAATCGCAGAAAAAGTCGAAAGT GAGAAGAAGGCTGAGGAACGGCAGGCGACCC TGGACAGGTACTTCAGGAAGGTT*TGA* |
| 101 | P13S/A107V SEL29 RNase H2 | ATGAAAGTTGCAGGTATAGATGAAGCTGGTC GTGGTTCTGCTATTGGTCCGCTGGTTATTGTT GCTGCTGTTGTGGATGAAAACAGTCTCCCCAA GCTGGAAGAGCTGAAAGTTAGAGACTCCAAA AAGCTGACCCCGGCGCAACGTGAAAAACTGT TCGATGAAATCGTAAAAGTACTGGATGATTAC TCTGTGGTCATTGTGTCCCCGCAGGACATTGA CGGTCGTAAGGGCAGCATGAACGAACTGGAG GTAGAAAACTTCGTTAAAGCCCTGAATAGCCT GAAAGTTAAGCCGGATGTTATTTACGCTGATG CCGTAGATGTTGATGAAGAACGTTTCGCTAG AGAGCTTGGCGAGCGTCTGAACTTCGAAGCG AAAGTTGTAGCCGAACATAAAGCGGATGCGA AGTATGAGATCGTATCCGCAGCCTCTATCCTG GCAAAAGTTATCCGTGACCGCGAGATCGAAA AGCTGAAAGCCGAATACGGTGATTTTGGTTCC GGTTACCCGTCTGATCCGCGTACTAGGGCATT CCTGGAAAATTACTATAGAGAACACGGCGAA TTCCCGCCGATCGTGCGTAAAGGTTGGAAGAC TCTAAAGAAAATCGCAGAAAAAGTCGAAAGT GAGAAGAAGGCTGAGGAACGGCAGGCGACCC TGGACAGGTACTTCAGGAAGGTT*TGA* |

[1]Location of mutations are shown in bold and underlined. The stop codon is shown in italics.

REFERENCES CITED

Joseph R Dobosy, Scott D Rose, Kristin R Beltz, Susan M Rupp, Kristy M Powers, Mark A Behlke and Joseph A Walder. RNase H-dependent PCR (rhPCR): improved specificity and single nucleotide polymorphism detection using blocked cleavable primers. BMC Biotechnology (2011), 11:80.

Ayumu Muroya, Daisuke Tsuchiya, Momoyo Ishikawa, Mitsuru Haruki, Masaaki Morikawa, Shigenori Kanaya, and Kosuke Morikawa. Catalytic center of an archaeal type 2 ribonuclease H as revealed by X-ray crystallographic and mutational analyses. Protein Science (2001), 10:707-714.

Monika P. Rychlik, Hyongi Chon, Susana M. Cerritelli, Paulina Klimek, Robert J. Crouch, and Marcin Nowotny. Crystal Structures of RNase H2 in Complex with Nucleic Acid Reveal the Mechanism of RNA-DNA Junction Recognition and Cleavage. Molecular Cell (2010), 40:658-670.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hybrid RNase H2 protein, said hybrid RNase H2 protein is selected from SEQ ID NO:2, 3, and 14-20.

2. A recombinant nucleic acid encoding the hybrid RNase H2 protein of claim 1.

3. A method for conducting primer extension, comprising: contacting a hybrid RNase H2 protein of claim 1 with a primer, a polynucleotide template, nucleoside triphosphates and a DNA polymerase under conditions suitable for a primer extension method, thereby producing an extended primer.

4. The method of claim 3, wherein the DNA polymerase comprises high-fidelity archaeal DNA polymerase.

5. The method of claim 3, wherein the primer comprises a blocked-cleavable primer.

6. The method of claim 5, wherein the primer extension method comprises a method for conducting polymerase chain reaction (PCR).

7. The method of claim 6, wherein the method for conducting PCR improves mismatch discrimination in a primer:polynucleotide hybrid formed between the primer and the polynucleotide template.

8. The method of claim 7, wherein the improvement in mismatch discrimination comprises an improvement in 3'-mismatch discrimination.

9. A reaction mixture comprising the hybrid RNase H2 protein according to claim 1, at least one primer, a polynucleotide template, nucleoside triphosphates and a DNA polymerase.

10. The reaction mixture of claim 9, wherein the DNA polymerase comprises a high-fidelity archaeal DNA polymerase.

11. The reaction mixture according to claim 9, wherein the at least one primer comprises a blocked-cleavable primer.

* * * * *

SEQUENCE LISTING

<160> NUMBER OF SEQ ID NOS: 101

<210> SEQ ID NO 1
<211> LENGTH: 255
<212> TYPE: PRT
<213> ORGANISM: Artificial Sequence
<220> FEATURE:
<223> OTHER INFORMATION: SYNTHETIC SEQUENCE

<400> SEQUENCE: 1

Met Lys Val Ala Gly Ala Asp Glu Ala Gly Arg Gly Pro Val Ile Gly
1               5                   10                  15

Pro Leu Val Ile Val Ala Ala Val Val Glu Glu Asp Lys Ile Arg Ser
                20                  25                  30

Leu Thr Lys Leu Gly Val Lys Asp Ser Lys Gln Leu Thr Pro Ala Gln
            35                  40                  45

Arg Glu Lys Leu Phe Asp Glu Ile Val Lys Val Leu Asp Asp Tyr Ser
        50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Glu Val Ile Tyr Ile Asp Ser Ala Asp Val Lys Ala Glu
                100                 105                 110

Arg Phe Ala Glu Asn Ile Arg Ser Arg Leu Ala Tyr Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Asn Phe Leu Lys Arg Phe Arg Asn
    210                 215                 220

Lys Leu Ala Ala Ala Leu Glu Ile Lys Arg Ala Ser Gln Pro Glu Leu
225                 230                 235                 240

Ala Pro Glu Asp Pro Glu Asp Val Glu His His His His His
                245                 250                 255

<210> SEQ ID NO 2
<211> LENGTH: 253
<212> TYPE: PRT
<213> ORGANISM: Artificial Sequence
<220> FEATURE:
<223> OTHER INFORMATION: SYNTHETIC SEQUENCE

<400> SEQUENCE: 2

Met Lys Val Ala Gly Ala Asp Glu Ala Gly Arg Gly Pro Val Ile Gly
1               5                   10                  15

Pro Leu Val Ile Val Ala Ala Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

```
Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Lys Phe Phe Lys Lys Pro Lys Leu
210                 215                 220

Ala Ala Ala Leu Glu Ile Lys Arg Ala Ser Gln Pro Glu Leu Ala Pro
225                 230                 235                 240

Glu Asp Pro Glu Asp Val Glu His His His His His His
                245                 250

<210> SEQ ID NO 3
<211> LENGTH: 259
<212> TYPE: PRT
<213> ORGANISM: Artificial Sequence
<220> FEATURE:
<223> OTHER INFORMATION: SYNTHETIC SEQUENCE

<400> SEQUENCE: 3

Met Lys Val Ala Gly Ile Asp Glu Ala Gly Arg Gly Pro Ala Ile Gly
 1                5                  10                  15

Pro Leu Val Ile Val Ala Ala Val Val Asp Glu Asn Ser Leu Pro Lys
                 20                  25                  30

Leu Glu Glu Leu Lys Val Arg Asp Ser Lys Lys Leu Thr Pro Ala Gln
            35                  40                  45

Arg Glu Lys Leu Phe Asp Glu Ile Val Lys Val Leu Asp Asp Tyr Ser
 50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
130                 135                 140

Ser Ile Leu Ala Lys Val Ile Arg Asp Arg Glu Ile Glu Lys Leu Lys
145                 150                 155                 160
```

```
Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220

Phe Arg Lys Val Lys Leu Ala Ala Ala Leu Glu Ile Lys Arg Ala Ser
225                 230                 235                 240

Gln Pro Glu Leu Ala Pro Glu Asp Pro Glu Asp Val Glu His His His
                245                 250                 255

His His His
```

```
<210> SEQ ID NO 4
<211> LENGTH: 54
<212> TYPE: DNA
<213> ORGANISM: Artificial Sequence
<220> FEATURE:
<223> OTHER INFORMATION: SYNTHETIC SEQUENCE

<400> SEQUENCE: 4
ggtgcagatg aagctggtcg tggttctgtt attggtccgc tggttattgt tgct       54

<210> SEQ ID NO 5
<211> LENGTH: 54
<212> TYPE: DNA
<213> ORGANISM: Artificial Sequence
<220> FEATURE:
<223> OTHER INFORMATION: SYNTHETIC SEQUENCE

<400> SEQUENCE: 5
agcaacaata accagcggac caataacaga accacgacca gcttcatctg cacc       54

<210> SEQ ID NO 6
<211> LENGTH: 57
<212> TYPE: DNA
<213> ORGANISM: Artificial Sequence
<220> FEATURE:
<223> OTHER INFORMATION: SYNTHETIC SEQUENCE

<400> SEQUENCE: 6
aagccggatg ttatttacgc tgatgccgta gatgttgatg aagaacgttt cgctaga    57

<210> SEQ ID NO 7
<211> LENGTH: 57
<212> TYPE: DNA
<213> ORGANISM: Artificial Sequence
<220> FEATURE:
<223> OTHER INFORMATION: SYNTHETIC SEQUENCE

<400> SEQUENCE: 7
tctagcgaaa cgttcttcat caacatctac ggcatcagcg taaataacat ccggctt    57

<210> SEQ ID NO 8
<211> LENGTH: 54
<212> TYPE: DNA
<213> ORGANISM: Artificial Sequence
<220> FEATURE:
<223> OTHER INFORMATION: SYNTHETIC SEQUENCE

<400> SEQUENCE: 8
ggtatagatg aagctggtcg tggttctgct attggtccgc tggttattgt tgct       54
```

<210> SEQ ID NO 9
<211> LENGTH: 54
<212> TYPE: DNA
<213> ORGANISM: Artificial Sequence
<220> FEATURE:
<223> OTHER INFORMATION: SYNTHETIC SEQUENCE

<400> SEQUENCE: 9
agcaacaata accagcggac caatagcaga accacgacca gcttcatcta tacc        54

<210> SEQ ID NO 10
<211> LENGTH: 53
<212> TYPE: DNA
<213> ORGANISM: Artificial Sequence
<220> FEATURE:
<223> OTHER INFORMATION: SYNTHETIC SEQUENCE

<400> SEQUENCE: 10
agactccaaa aagctgaccc cggcgcgccg tgaaaaactg ttcgatgaaa tcg         53

<210> SEQ ID NO 11
<211> LENGTH: 53
<212> TYPE: DNA
<213> ORGANISM: Artificial Sequence
<220> FEATURE:
<223> OTHER INFORMATION: SYNTHETIC SEQUENCE

<400> SEQUENCE: 11
cgatttcatc gaacagtttt tcacggcgcg ccggggtcag cttttggag tct          53

<210> SEQ ID NO 12
<211> LENGTH: 57
<212> TYPE: DNA
<213> ORGANISM: Artificial Sequence
<220> FEATURE:
<223> OTHER INFORMATION: SYNTHETIC SEQUENCE

<400> SEQUENCE: 12
aagccggatg ttatttacgc tgatgccgta gatgttgatg aagaacgttt cgctaga     57

<210> SEQ ID NO 13
<211> LENGTH: 57
<212> TYPE: DNA
<213> ORGANISM: Artificial Sequence
<220> FEATURE:
<223> OTHER INFORMATION: SYNTHETIC SEQUENCE

<400> SEQUENCE: 13
tctagcgaaa cgttcttcat caacatctac ggcatcagcg taaataacat ccggctt     57

<210> SEQ ID NO 14
<211> LENGTH: 253
<212> TYPE: PRT
<213> ORGANISM: Artificial Sequence
<220> FEATURE:
<223> OTHER INFORMATION: SYNTHETIC SEQUENCE

<400> SEQUENCE: 14

Met Lys Val Ala Gly Ala Asp Glu Ala Gly Arg Gly Ser Val Ile Gly
1               5                   10                  15

Pro Leu Val Ile Ala Ala Val Val Asp Glu Asn Ser Leu Pro Lys
            20                  25                  30

Leu Glu Glu Leu Lys Val Arg Asp Ser Lys Lys Leu Thr Pro Lys Arg
        35                  40                  45

```
Arg Glu Lys Leu Phe Asp Glu Ile Val Lys Val Leu Asp Asp Tyr Ser
     50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Asp Val Ile Tyr Ala Asp Ala Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Lys Phe Phe Lys Lys Pro Lys Leu
    210                 215                 220

Ala Ala Ala Leu Glu Ile Lys Arg Ala Ser Gln Pro Glu Leu Ala Pro
225                 230                 235                 240

Glu Asp Pro Glu Asp Val Glu His His His His His His
                245                 250

<210> SEQ ID NO 15
<211> LENGTH: 253
<212> TYPE: PRT
<213> ORGANISM: Artificial Sequence
<220> FEATURE:
<223> OTHER INFORMATION: SYNTHETIC SEQUENCE

<400> SEQUENCE: 15

Met Lys Val Ala Gly Ala Asp Glu Ala Gly Arg Gly Pro Val Ile Gly
 1               5                  10                  15

Pro Leu Val Ile Val Ala Ala Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

Arg Glu Lys Leu Phe Asp Glu Ile Val Lys Val Leu Asp Asp Tyr Ser
     50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Asp Val Ile Tyr Ala Asp Ala Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Ile Arg Asp Arg Glu Ile Glu Lys Leu Lys
145                 150                 155                 160
```

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Lys Phe Phe Lys Lys Pro Lys Leu
        210                 215                 220

Ala Ala Ala Leu Glu Ile Lys Arg Ala Ser Gln Pro Glu Leu Ala Pro
225                 230                 235                 240

Glu Asp Pro Glu Asp Val Glu His His His His His His
            245                 250

<210> SEQ ID NO 16
<211> LENGTH: 253
<212> TYPE: PRT
<213> ORGANISM: Artificial Sequence
<220> FEATURE:
<223> OTHER INFORMATION: SYNTHETIC SEQUENCE

<400> SEQUENCE: 16

Met Lys Val Ala Gly Ala Asp Glu Ala Gly Arg Gly Ser Val Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Lys Arg
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Val Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Lys Lys Trp Leu Glu Glu Trp Tyr Ser Lys His Gly Asn Phe Pro Pro
        180                 185                 190

Ile Val Arg Arg Thr Trp Asp Thr Ala Lys Lys Ile Glu Glu Lys Phe
            195                 200                 205

Lys Arg Ala Gln Leu Thr Leu Asp Lys Phe Phe Lys Lys Pro Lys Leu
        210                 215                 220

Ala Ala Ala Leu Glu Ile Lys Arg Ala Ser Gln Pro Glu Leu Ala Pro
225                 230                 235                 240

Glu Asp Pro Glu Asp Val Glu His His His His His His
            245                 250

<210> SEQ ID NO 17

```
<211> LENGTH: 259
<212> TYPE: PRT
<213> ORGANISM: Artificial Sequence
<220> FEATURE:
<223> OTHER INFORMATION: SYNTHETIC SEQUENCE

<400> SEQUENCE: 17

Met Lys Val Ala Gly Ile Asp Glu Ala Gly Arg Gly Ser Ala Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220

Phe Arg Lys Val Lys Leu Ala Ala Ala Leu Glu Ile Lys Arg Ala Ser
225                 230                 235                 240

Gln Pro Glu Leu Ala Pro Glu Asp Pro Glu Asp Val Glu His His His
                245                 250                 255

His His His

<210> SEQ ID NO 18
<211> LENGTH: 259
<212> TYPE: PRT
<213> ORGANISM: Artificial Sequence
<220> FEATURE:
<223> OTHER INFORMATION: SYNTHETIC SEQUENCE

<400> SEQUENCE: 18

Met Lys Val Ala Gly Ile Asp Glu Ala Gly Arg Gly Pro Ala Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Ala Arg
        35                  40                  45

Arg Glu Lys Leu Phe Asp Glu Ile Val Lys Val Leu Asp Asp Tyr Ser
    50                  55                  60
```

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
210                 215                 220

Phe Arg Lys Val Lys Leu Ala Ala Ala Leu Glu Ile Lys Arg Ala Ser
225                 230                 235                 240

Gln Pro Glu Leu Ala Pro Glu Asp Pro Glu Asp Val Glu His His His
                245                 250                 255

His His His

<210> SEQ ID NO 19
<211> LENGTH: 259
<212> TYPE: PRT
<213> ORGANISM: Artificial Sequence
<220> FEATURE:
<223> OTHER INFORMATION: SYNTHETIC SEQUENCE

<400> SEQUENCE: 19

Met Lys Val Ala Gly Ile Asp Glu Ala Gly Arg Gly Pro Ala Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Val Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Arg Ala Phe Leu Glu Asn Tyr Tyr Arg Glu His Gly Glu Phe Pro Pro
        180                 185                 190

Ile Val Arg Lys Gly Trp Lys Thr Leu Lys Lys Ile Ala Glu Lys Val
            195                 200                 205

Glu Ser Glu Lys Lys Ala Glu Glu Arg Gln Ala Thr Leu Asp Arg Tyr
        210                 215                 220

Phe Arg Lys Val Lys Leu Ala Ala Ala Leu Glu Ile Lys Arg Ala Ser
225                 230                 235                 240

Gln Pro Glu Leu Ala Pro Glu Asp Pro Glu Asp Val Glu His His His
            245                 250                 255

His His His

<210> SEQ ID NO 20
<211> LENGTH: 259
<212> TYPE: PRT
<213> ORGANISM: Artificial Sequence
<220> FEATURE:
<223> OTHER INFORMATION: SYNTHETIC SEQUENCE

<400> SEQUENCE: 20

Met Lys Val Ala Gly Ile Asp Glu Ala Gly Arg Gly Ser Ala Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Val Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
            165                 170                 175

Arg Ala Phe Leu Glu Asn Tyr Tyr Arg Glu His Gly Glu Phe Pro Pro
        180                 185                 190

Ile Val Arg Lys Gly Trp Lys Thr Leu Lys Lys Ile Ala Glu Lys Val
    195                 200                 205

Glu Ser Glu Lys Lys Ala Glu Glu Arg Gln Ala Thr Leu Asp Arg Tyr
        210                 215                 220

Phe Arg Lys Val Lys Leu Ala Ala Ala Leu Glu Ile Lys Arg Ala Ser
225                 230                 235                 240

Gln Pro Glu Leu Ala Pro Glu Asp Pro Glu Asp Val Glu His His His
            245                 250                 255

His His His

<210> SEQ ID NO 21
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 21
cagcctcatc caaaagagga aa                                    22

<210> SEQ ID NO 22
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-PROPRIETARY BLOCKER GROUP

<400> SEQUENCE: 22
cagcctcatc caaaagagga aacaggag                              28

<210> SEQ ID NO 23
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 23
ctcactctaa accccagcat t                                     21

<210> SEQ ID NO 24
<211> LENGTH: 41
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'- Iowa Black FLUORESCENT QUENCHER
<220> FEATURE:
<221> NAME/KEY: misc_feature
<222> LOCATION: (36)..(36)
<223> OTHER INFORMATION: RIBONUCLEOTIDE
<220> FEATURE:
<221> NAME/KEY: misc_feature
<222> LOCATION: (41)..(41)
<223> OTHER INFORMATION: 3'-(6-FAM) FLUORESCENT LABEL

<400> SEQUENCE: 24
tataagctac cagcatggtt tttccatgct ggtagcttat a               41

<210> SEQ ID NO 25
<211> LENGTH: 41
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (36)..(36)

<223> OTHER INFORMATION: RIBONUCLEOTIDE

<400> SEQUENCE: 25
tataagctac cagcatggtt tttccatgct ggtagcttat a                41

<210> SEQ ID NO 26
<211> LENGTH: 23
<212> TYPE: DNA
<213> ORGANISM: Artificial Sequence
<220> FEATURE:
<223> OTHER INFORMATION: SYNTHETIC SEQUENCE

<400> SEQUENCE: 26
agctctgccc aaagattacc ctg                                   23

<210> SEQ ID NO 27
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 27
ctgagcttca tgcctttact gt                                    22

<210> SEQ ID NO 28
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONCLEOTIDE
<220> FEATURE:
<221> NAME/KEY: misc_feature
<222> LOCATION: (28)..(28)
<223> OTHER INFORMATION: 3'-C3 spacer (propanediol) blocker group

<400> SEQUENCE: 28
ctgagcttca tgcctttact gtacccccc                             28

<210> SEQ ID NO 29
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 spacer (propanediol) blocker group

<400> SEQUENCE: 29
ctgagcttca tgcctttact gtcccccc                              28

<210> SEQ ID NO 30
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature

```
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 spacer (propanediol) blocker group

<400> SEQUENCE: 30
ctgagcttca tgcctttact gtgccccc                                              28

<210> SEQ ID NO 31
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 spacer (propanediol) blocker group

<400> SEQUENCE: 31
ctgagcttca tgcctttact gtuccccc                                              28

<210> SEQ ID NO 32
<211> LENGTH: 103
<212> TYPE: DNA
<213> ORGANISM: Artificial Sequence
<220> FEATURE:
<223> OTHER INFORMATION: SYNTHETIC SEQUENCE

<400> SEQUENCE: 32
agctctgccc aaagattacc ctgacagcta agtggcagtg gaagttggcc tcagaagtag           60
tggccagctg tgtgtcgggg aacagtaaag gcatgaagct cag                           103

<210> SEQ ID NO 33
<211> LENGTH: 103
<212> TYPE: DNA
<213> ORGANISM: Artificial Sequence
<220> FEATURE:
<223> OTHER INFORMATION: SYNTHETIC SEQUENCE

<400> SEQUENCE: 33
agctctgccc aaagattacc ctgacagcta agtggcagtg gaagttggcc tcagaagtag           60
tggccagctg tgtgtcgggg cacagtaaag gcatgaagct cag                           103

<210> SEQ ID NO 34
<211> LENGTH: 103
<212> TYPE: DNA
<213> ORGANISM: Artificial Sequence
<220> FEATURE:
<223> OTHER INFORMATION: SYNTHETIC SEQUENCE

<400> SEQUENCE: 34
agctctgccc aaagattacc ctgacagcta agtggcagtg gaagttggcc tcagaagtag           60
tggccagctg tgtgtcgggg gacagtaaag gcatgaagct cag                           103

<210> SEQ ID NO 35
<211> LENGTH: 103
<212> TYPE: DNA
<213> ORGANISM: Artificial Sequence
<220> FEATURE:
```

<223> OTHER INFORMATION: SYNTHETIC SEQUENCE

<400> SEQUENCE: 35
agctctgccc aaagattacc ctgacagcta agtggcagtg aagttggcc tcagaagtag    60 tggccagctg tgtgtcgggg tacagtaaag gcatgaagct cag                    103

<210> SEQ ID NO 36
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 36
gtgattttgg tctagctaca gt                                            22

<210> SEQ ID NO 37
<211> LENGTH: 23
<212> TYPE: DNA
<213> ORGANISM: Artificial Sequence
<220> FEATURE:
<223> OTHER INFORMATION: SYNTHETIC SEQUENCE

<400> SEQUENCE: 37
cctcaattct taccatccac aaa                                           23

<210> SEQ ID NO 38
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 spacer (propanediol) blocker group

<400> SEQUENCE: 38
gtgattttgg tctagctaca gtgaaatg                                      28

<210> SEQ ID NO 39
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 spacer (propanediol) blocker group

<400> SEQUENCE: 39
gtgattttgg tctagctaca gagaaatg                                      28

<210> SEQ ID NO 40
<211> LENGTH: 401
<212> TYPE: DNA
<213> ORGANISM: Artificial Sequence
<220> FEATURE:
<223> OTHER INFORMATION: SYNTHETIC SEQUENCE

<400> SEQUENCE: 40

```
taagaggaaa gatgaagtac tatgttttaa agaatattat attacagaat tatagaaatt    60
agatctctta cctaaactct tcataatgct tgctctgata ggaaaatgag atctactgtt   120
ttcctttact tactacacct cagatatatt tcttcatgaa gacctcacag taaaaatagg   180
tgattttggt ctagctacag tgaaatctcg atggagtggg tcccatcagt ttgaacagtt   240
gtctggatcc attttgtgga tggtaagaat tgaggctatt tttccactga ttaaattttt   300
ggccctgaga tgctgctgag ttactagaaa gtcattgaag gtctcaacta tagtattttc   360
atagttccca gtattcacaa aaatcagtgt tcttattttt t                       401
```

<210> SEQ ID NO 41
<211> LENGTH: 401
<212> TYPE: DNA
<213> ORGANISM: Artificial Sequence
<220> FEATURE:
<223> OTHER INFORMATION: SYNTHETIC SEQUENCE

<400> SEQUENCE: 41

```
taagaggaaa gatgaagtac tatgttttaa agaatattat attacagaat tatagaaatt    60
agatctctta cctaaactct tcataatgct tgctctgata ggaaaatgag atctactgtt   120
ttcctttact tactacacct cagatatatt tcttcatgaa gacctcacag taaaaatagg   180
tgattttggt ctagctacag agaaatctcg atggagtggg tcccatcagt ttgaacagtt   240
gtctggatcc attttgtgga tggtaagaat tgaggctatt tttccactga ttaaattttt   300
ggccctgaga tgctgctgag ttactagaaa gtcattgaag gtctcaacta tagtattttc   360
atagttccca gtattcacaa aaatcagtgt tcttattttt t                       401
```

<210> SEQ ID NO 42
<211> LENGTH: 23
<212> TYPE: DNA
<213> ORGANISM: Artificial Sequence
<220> FEATURE:
<223> OTHER INFORMATION: SYNTHETIC SEQUENCE

<400> SEQUENCE: 42

```
ggcagatttt cttctgcacc gcg                                            23
```

<210> SEQ ID NO 43
<211> LENGTH: 27
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (25)..(25)
<223> OTHER INFORMATION: INTERNUCLEOTIDE C3 PROPANE DIOL SPACER
<220> FEATURE:
<221> NAME/KEY: misc_feature
<222> LOCATION: (27)..(27)
<223> OTHER INFORMATION: 3'-C3 PROPANE DIOL SPACER

<400> SEQUENCE: 43

```
ggcagatttt cttctgcacc gcggttc                                        27
```

<210> SEQ ID NO 44

```
<211> LENGTH: 27
<212> TYPE: DNA
<213> ORGANISM: Artificial Sequence
<220> FEATURE:
<223> OTHER INFORMATION: SYNTHETIC SEQUENCE

<400> SEQUENCE: 44
tcccgtcgag caccagcaat tttactc                                          27

<210> SEQ ID NO 45
<211> LENGTH: 24
<212> TYPE: DNA
<213> ORGANISM: Artificial Sequence
<220> FEATURE:
<223> OTHER INFORMATION: SYNTHETIC SEQUENCE

<400> SEQUENCE: 45
ctttggataa ggaagaagcc aact                                             24

<210> SEQ ID NO 46
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (24)..(24)
<223> OTHER INFORMATION: RIBONUCLEOTIDE
<220> FEATURE:
<221> NAME/KEY: misc_feature
<222> LOCATION: (26)..(26)
<223> OTHER INFORMATION: INTERNUCLEOTIDE C2 PROPANE DIOL
<220> FEATURE:
<221> NAME/KEY: misc_feature
<222> LOCATION: (28)..(28)
<223> OTHER INFORMATION: 3'-C2 PROPANE DIOL

<400> SEQUENCE: 46
ctttggataa ggaagaagcc aacugcag                                         28

<210> SEQ ID NO 47
<211> LENGTH: 28
<212> TYPE: DNA
<213> ORGANISM: Artificial Sequence
<220> FEATURE:
<223> OTHER INFORMATION: SYNTHETIC SEQUENCE

<400> SEQUENCE: 47
gggagcttga aatgaacaag gtgagaag                                         28

<210> SEQ ID NO 48
<211> LENGTH: 46
<212> TYPE: DNA
<213> ORGANISM: Artificial Sequence
<220> FEATURE:
<223> OTHER INFORMATION: SYNTHETIC SEQUENCE

<400> SEQUENCE: 48
cagccagccg cagcacgttc gctcatagga gatatggtag agccgc                     46

<210> SEQ ID NO 49
<211> LENGTH: 51
<212> TYPE: DNA
<213> ORGANISM: Artificial Sequence
<220> FEATURE:
<223> OTHER INFORMATION: SYNTHETIC SEQUENCE

<400> SEQUENCE: 49
```
gagagaattt gtaccacctc ccaccgggca catagcagtc ctagggacag t                51

<210> SEQ ID NO 50
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 50
ggcttggctc tgctaacacg tt                                               22

<210> SEQ ID NO 51
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 51
ggacgtttgt aatgtccgct cc                                               22

<210> SEQ ID NO 52
<211> LENGTH: 20
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'-(6-carboxyfluorescein) MOIETY
<220> FEATURE:
<221> NAME/KEY: misc_feature
<222> LOCATION: (11)..(11)
<223> OTHER INFORMATION: RIBONUCLEOTIDE
<220> FEATURE:
<221> NAME/KEY: misc_feature
<222> LOCATION: (20)..(20)
<223> OTHER INFORMATION: 3'-(Iowa Black FQ fluorescence quencher) MOIETY

<400> SEQUENCE: 52
acgtgctgcg gctggctggt                                                  20

<210> SEQ ID NO 53
<211> LENGTH: 48
<212> TYPE: DNA
<213> ORGANISM: Artificial Sequence
<220> FEATURE:
<223> OTHER INFORMATION: SYNTHETIC SEQUENCE

<400> SEQUENCE: 53
ccaaagagta aagtccttct ctctcgagag actgttggcc cttgaagg                   48

<210> SEQ ID NO 54
<211> LENGTH: 47
<212> TYPE: DNA
<213> ORGANISM: Artificial Sequence
<220> FEATURE:
<223> OTHER INFORMATION: SYNTHETIC SEQUENCE

<400> SEQUENCE: 54
gtgttgatgt tatccaccttt ttgtggacta ggaaaacaga tcaatag                    47

<210> SEQ ID NO 55
<211> LENGTH: 20
<212> TYPE: DNA

```
<213> ORGANISM: Artificial Sequence
<220> FEATURE:
<223> OTHER INFORMATION: SYNTHETIC SEQUENCE

<400> SEQUENCE: 55
taatcctgga actccggtgc                                                 20

<210> SEQ ID NO 56
<211> LENGTH: 23
<212> TYPE: DNA
<213> ORGANISM: Artificial Sequence
<220> FEATURE:
<223> OTHER INFORMATION: SYNTHETIC SEQUENCE

<400> SEQUENCE: 56
tttatgccaa ttaacatttt gac                                             23

<210> SEQ ID NO 57
<211> LENGTH: 24
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'-(6-carboxyfluorescein) MOIETY
<220> FEATURE:
<221> NAME/KEY: misc_feature
<222> LOCATION: (14)..(14)
<223> OTHER INFORMATION: RIBONCLEOTIDE
<220> FEATURE:
<221> NAME/KEY: misc_feature
<222> LOCATION: (24)..(24)
<223> OTHER INFORMATION: 3'-(Iowa Black FQ fluorescence quencher) MOIETY

<400> SEQUENCE: 57
cctccctgtg gatgagagag aagg                                            24

<210> SEQ ID NO 58
<211> LENGTH: 52
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (47)..(47)
<223> OTHER INFORMATION: RIBONUCLEOTIDE
<220> FEATURE:
<221> NAME/KEY: misc_feature
<222> LOCATION: (52)..(52)
<223> OTHER INFORMATION: 3'-C3 PROPANE DIOL

<400> SEQUENCE: 58
cagccagccg cagcacgttc gctcatagga gatatggtag agccgcagac ag             52

<210> SEQ ID NO 59
<211> LENGTH: 57
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (52)..(52)
<223> OTHER INFORMATION: RIBONUCLEOTIDE
<220> FEATURE:
<221> NAME/KEY: misc_feature
<222> LOCATION: (57)..(57)
<223> OTHER INFORMATION: 3'-C3 PROPANE DIOL
```

<400> SEQUENCE: 59
gagagaattt gtaccacctc ccaccgggca catagcagtc ctagggacag tggcgtt    57

<210> SEQ ID NO 60
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 PROPANE DIOL

<400> SEQUENCE: 60
ggcttggctc tgctaacacg ttgctcaa    28

<210> SEQ ID NO 61
<211> LENGTH: 28
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (24)..(24)
<223> OTHER INFORMATION: RIBONUCLEOTIDE
<220> FEATURE:
<221> NAME/KEY: misc_feature
<222> LOCATION: (28)..(28)
<223> OTHER INFORMATION: 3'-C3 PROPANE DIOL

<400> SEQUENCE: 61
ggacgtttgt aatgtccgct ccggcact    28

<210> SEQ ID NO 62
<211> LENGTH: 20
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'-(6-carboxyfluorescein) MOIETY
<220> FEATURE:
<221> NAME/KEY: misc_feature
<222> LOCATION: (11)..(11)
<223> OTHER INFORMATION: RIBONUCLEOTIDE
<220> FEATURE:
<221> NAME/KEY: misc_feature
<222> LOCATION: (20)..(20)
<223> OTHER INFORMATION: 3'-(Iowa Black FQ fluorescence quencher) MOIETY

<400> SEQUENCE: 62
acgtgctgcg gctggctggt    20

<210> SEQ ID NO 63
<211> LENGTH: 54
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (49)..(49)

```
<223> OTHER INFORMATION: RIBONUCLEOTIDE
<220> FEATURE:
<221> NAME/KEY: misc_feature
<222> LOCATION: (54)..(54)
<223> OTHER INFORMATION: 3'-C3 PROPANE DIOL

<400> SEQUENCE: 63
ccaaagagta aagtccttct ctctcgagag actgttggcc cttgaaggag agca          54

<210> SEQ ID NO 64
<211> LENGTH: 53
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (48)..(48)
<223> OTHER INFORMATION: RIBONUCLEOTIDE
<220> FEATURE:
<221> NAME/KEY: misc_feature
<222> LOCATION: (53)..(53)
<223> OTHER INFORMATION: 3'-C3 PROPANE DIOL

<400> SEQUENCE: 64
gtgttgatgt tatccacctt ttgtggacta ggaaaacaga tcaatagata agc           53

<210> SEQ ID NO 65
<211> LENGTH: 26
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (21)..(21)
<223> OTHER INFORMATION: RIBONUCLEOTIDE
<220> FEATURE:
<221> NAME/KEY: misc_feature
<222> LOCATION: (26)..(26)
<223> OTHER INFORMATION: 3'-C3 PROPANE DIOL

<400> SEQUENCE: 65
taatcctgga actccggtgc uaaggt                                         26

<210> SEQ ID NO 66
<211> LENGTH: 29
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (24)..(24)
<223> OTHER INFORMATION: RIBONUCLEOTIDE
<220> FEATURE:
<221> NAME/KEY: misc_feature
<222> LOCATION: (29)..(29)
<223> OTHER INFORMATION: 3'-C3 PROPANE DIOL

<400> SEQUENCE: 66
tttatgccaa ttaacatttt gacuttatt                                      29

<210> SEQ ID NO 67
<211> LENGTH: 24
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
```

-continued

```
<222> LOCATION: (1)..(1)
<223> OTHER INFORMATION: 5'-(6-carboxyfluorescein) MOIETY
<220> FEATURE:
<221> NAME/KEY: misc_feature
<222> LOCATION: (14)..(14)
<223> OTHER INFORMATION: RIBONUCLEOTIDE
<220> FEATURE:
<221> NAME/KEY: misc_feature
<222> LOCATION: (24)..(24)
<223> OTHER INFORMATION: 3'-(Iowa Black FQ fluorescence quencher) MOIETY

<400> SEQUENCE: 67
cctccctgtg gatgagagag aagg                                           24

<210> SEQ ID NO 68
<211> LENGTH: 50
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (47)..(47)
<223> OTHER INFORMATION: RIBONUCLEOTIDE
<220> FEATURE:
<221> NAME/KEY: misc_feature
<222> LOCATION: (48)..(48)
<223> OTHER INFORMATION: 2 C3 PROPANE DIOL INTERNUCLEOTIDE LINKAGES

<400> SEQUENCE: 68
cagccagccg cagcacgttc gctcatagga gatatggtag agccgcagag                50

<210> SEQ ID NO 69
<211> LENGTH: 55
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (52)..(52)
<223> OTHER INFORMATION: RIBONUCLEOTIDE
<220> FEATURE:
<221> NAME/KEY: misc_feature
<222> LOCATION: (53)..(53)
<223> OTHER INFORMATION: 2 C3 PROPANE DIOL INTERNUCLEOTIDE LINKAGES

<400> SEQUENCE: 69
gagagaattt gtaccacctc ccaccgggca catagcagtc ctagggacag tggtt           55

<210> SEQ ID NO 70
<211> LENGTH: 26
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (24)..(24)
<223> OTHER INFORMATION: 2 C3 PROPANE DIOL INTERNUCLEOTIDE LINKAGES

<400> SEQUENCE: 70
ggcttggctc tgctaacacg ttgcaa                                          26

<210> SEQ ID NO 71
<211> LENGTH: 26
<212> TYPE: DNA
```

```
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (23)..(23)
<223> OTHER INFORMATION: RIBONUCLEOTIDE
<220> FEATURE:
<221> NAME/KEY: misc_feature
<222> LOCATION: (24)..(24)
<223> OTHER INFORMATION: 2 C3 PROPANE DIOL INTERNUCLEOTIDE LINKAGES

<400> SEQUENCE: 71
ggacgtttgt aatgtccgct ccggct                                          26

<210> SEQ ID NO 72
<211> LENGTH: 20
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'-(6-carboxyfluorescein) MOIETY
<220> FEATURE:
<221> NAME/KEY: misc_feature
<222> LOCATION: (11)..(11)
<223> OTHER INFORMATION: RIBONUCLEOTIDE
<220> FEATURE:
<221> NAME/KEY: misc_feature
<222> LOCATION: (20)..(20)
<223> OTHER INFORMATION: 3'-(Iowa Black FQ fluorescence quencher) MOIETY

<400> SEQUENCE: 72
acgtgctgcg gctggctggt                                                 20

<210> SEQ ID NO 73
<211> LENGTH: 52
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (49)..(49)
<223> OTHER INFORMATION: RIBONUCLEOTIDE
<220> FEATURE:
<221> NAME/KEY: misc_feature
<222> LOCATION: (50)..(50)
<223> OTHER INFORMATION: 2 C3 PROPANE DIOL INTERNUCLEOTIDE LINKAGES

<400> SEQUENCE: 73
ccaaagagta aagtccttct ctctcgagag actgttggcc cttgaaggag ca             52

<210> SEQ ID NO 74
<211> LENGTH: 51
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (48)..(48)
<223> OTHER INFORMATION: RIBONUCLEOTIDE
<220> FEATURE:
<221> NAME/KEY: misc_feature
<222> LOCATION: (49)..(49)
<223> OTHER INFORMATION: 2 C3 PROPANE DIOL INTERNUCLEOTIDE LINKAGES

<400> SEQUENCE: 74
gtgttgatgt tatccacctt ttgtggacta ggaaaacaga tcaatagatg c              51
```

<210> SEQ ID NO 75
<211> LENGTH: 24
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (21)..(21)
<223> OTHER INFORMATION: RIBONUCLEOTIDE
<220> FEATURE:
<221> NAME/KEY: misc_feature
<222> LOCATION: (22)..(22)
<223> OTHER INFORMATION: 2 C3 PROPANE DIOL INTERNUCLEOTIDE LINKAGES

<400> SEQUENCE: 75
taatcctgga actccggtgc uagt                                          24

<210> SEQ ID NO 76
<211> LENGTH: 27
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (24)..(24)
<223> OTHER INFORMATION: RIBONUCLEOTIDE
<220> FEATURE:
<221> NAME/KEY: misc_feature
<222> LOCATION: (25)..(25)
<223> OTHER INFORMATION: 2 C3 PROPANE DIOL INTERNUCLEOTIDE LINKAGES

<400> SEQUENCE: 76
tttatgccaa ttaacatttt gacuttt                                       27

<210> SEQ ID NO 77
<211> LENGTH: 24
<212> TYPE: DNA
<213> ORGANISM: Artificial Sequence
<220> FEATURE:
<223> OTHER INFORMATION: SYNTHETIC SEQUENCE
<220> FEATURE:
<221> NAME/KEY: misc_feature
<222> LOCATION: (1)..(1)
<223> OTHER INFORMATION: 5'-(6-carboxyfluorescein) MOIETY
<220> FEATURE:
<221> NAME/KEY: misc_feature
<222> LOCATION: (14)..(14)
<223> OTHER INFORMATION: RIBONUCLEOTIDE
<220> FEATURE:
<221> NAME/KEY: misc_feature
<222> LOCATION: (24)..(24)
<223> OTHER INFORMATION: 3'-(Iowa Black FQ fluorescence quencher) MOIETY

<400> SEQUENCE: 77
cctccctgtg gatgagagag aagg                                          24

<210> SEQ ID NO 78
<211> LENGTH: 768
<212> TYPE: DNA
<213> ORGANISM: Artificial Sequence
<220> FEATURE:
<223> OTHER INFORMATION: SYNTHETIC SEQUENCE

<400> SEQUENCE: 78
atgaaagttg caggtgcaga tgaagctggt cgtggtccag ttattggtcc gctggttatt    60
gttgctgctg ttgtggagga agacaaaatc cgctctctga ctaagctggg tgttaaagac   120

| | |
|---|---|
| tccaaacagc tgaccccggc gcaacgtgaa aaactgttcg atgaaatcgt aaaagtactg | 180 |
| gatgattact ctgtggtcat tgtgtccccg caggacattg acggtcgtaa gggcagcatg | 240 |
| aacgaactgg aggtagaaaa cttcgttaaa gccctgaata gcctgaaagt taagccggaa | 300 |
| gttatttaca ttgattccgc tgatgttaaa gctgaacgtt tcgctgaaaa cattcgcagc | 360 |
| cgtctggcgt acgaagcgaa agttgtagcc gaacataaag cggatgcgaa gtatgagatc | 420 |
| gtatccgcag cctctatcct ggcaaaagtt atccgtgacc gcgagatcga aaagctgaaa | 480 |
| gccgaatacg gtgattttgg ttccggttac ccgtctgatc cgcgtactaa gaaatggctg | 540 |
| gaagaatggt atagcaaaca cggcaatttc ccgccgatcg tgcgtcgtac ttgggatact | 600 |
| gcaaagaaaa tcgaagaaaa attcaaacgt gcgcagctga ccctggacaa cttcctgaag | 660 |
| cgttttcgca acaagcttgc ggccgcactc gagatcaaac gggctagcca gccagaactc | 720 |
| gccccggaag accccgagga tgtcgagcac caccaccacc accactga | 768 |

<210> SEQ ID NO 79
<211> LENGTH: 762
<212> TYPE: DNA
<213> ORGANISM: Artificial Sequence
<220> FEATURE:
<223> OTHER INFORMATION: SYNTHETIC SEQUENCE

<400> SEQUENCE: 79

| | |
|---|---|
| atgaaagttg caggtgcaga tgaagctggt cgtggtccag ttattggtcc gctggttatt | 60 |
| gttgctgctg ttgtggatga aaacagtctc cccaagctgg aagagctgaa agttagagac | 120 |
| tccaaaaagc tgaccccgaa cgacgtgaaa aaactgttcg atgaaatcgt aaaagtactg | 180 |
| gatgattact ctgtggtcat tgtgtccccg caggacattg acggtcgtaa gggcagcatg | 240 |
| aacgaactgg aggtagaaaa cttcgttaaa gccctgaata gcctgaaagt taagccggat | 300 |
| gttatttacg ctgatgccgc tgatgttgat gaagaacgtt tcgctagaga gcttggcgag | 360 |
| cgtctgaact tcgaagcgga agttgtagcc aaacataaag cggatgacat ctttccggtc | 420 |
| gtatccgcag cctctatcct ggcaaaagtt atccgtgacc gcgagatcga aaagctgaaa | 480 |
| gccgaatacg gtgattttgg ttccggttac ccgtctgatc cgcgtactaa gaaatggctg | 540 |
| gaagaatggt atagcaaaca cggcaatttc ccgccgatcg tgcgtcgtac ttgggatact | 600 |
| gcaaagaaaa tcgaagaaaa attcaaacgt gcgcagctga ccctggacaa gttcttcaag | 660 |
| aaacctaagc ttgcggccgc actcgagatc aaacgggcta gccagccaga actcgccccg | 720 |
| gaagaccccg aggatgtcga gcaccaccac caccaccact ga | 762 |

<210> SEQ ID NO 80
<211> LENGTH: 780
<212> TYPE: DNA
<213> ORGANISM: Artificial Sequence
<220> FEATURE:
<223> OTHER INFORMATION: SYNTHETIC SEQUENCE

<400> SEQUENCE: 80

| | |
|---|---|
| atgaaagttg caggtataga tgaagctggt cgtggtccag ctattggtcc gctggttatt | 60 |
| gttgctgctg ttgtggatga aaacagtctc cccaagctgg aagagctgaa agttagagac | 120 |
| tccaaaaagc tgaccccggc gcaacgtgaa aaactgttcg atgaaatcgt aaaagtactg | 180 |
| gatgattact ctgtggtcat tgtgtccccg caggacattg acggtcgtaa gggcagcatg | 240 |
| aacgaactgg aggtagaaaa cttcgttaaa gccctgaata gcctgaaagt taagccggat | 300 |
| gttatttacg ctgatgccgc tgatgttgat gaagaacgtt tcgctagaga gcttggcgag | 360 |

```
cgtctgaact tcgaagcgaa agttgtagcc aacataaag cggatgcgaa gtatgagatc    420
gtatccgcag cctctatcct ggcaaaagtt atccgtgacc gcgagatcga aaagctgaaa    480
gccgaatacg gtgattttgg ttccggttac ccgtctgatc cgcgtactag ggcattcctg    540
gaaaattact atagagaaca cggcgaattc ccgccgatcg tgcgtaaagg ttggaagact    600
ctaaagaaaa tcgcagaaaa agtcgaaagt gagaagaagg ctgaggaacg gcaggcgacc    660
ctggacaggt acttcaggaa ggttaagctt gcggccgcac tcgagatcaa acgggctagc    720
cagccagaac tcgccccgga agaccccgag gatgtcgagc accaccacca ccaccactga    780
```

<210> SEQ ID NO 81
<211> LENGTH: 762
<212> TYPE: DNA
<213> ORGANISM: Artificial Sequence
<220> FEATURE:
<223> OTHER INFORMATION: SYNTHETIC SEQUENCE

<400> SEQUENCE: 81

```
atgaaagttg caggtgcaga tgaagctggt cgtggttctg ttattggtcc gctggttatt     60
gttgctgctg ttgtggatga aacagtctc cccaagctgg aagagctgaa agttagagac    120
tccaaaaagc tgaccccgaa gcgacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg ctgatgccgc tgatgttgat gaagaacgtt tcgctagaga gcttggcgag    360
cgtctgaact tcgaagcgga agttgtagcc aaacataaag cggatgacat ctttccggtc    420
gtatccgcag cctctatcct ggcaaaagtt atccgtgacc gcgagatcga aaagctgaaa    480
gccgaatacg gtgattttgg ttccggttac ccgtctgatc cgcgtactaa gaaatggctg    540
gaagaatggt atagcaaaca cggcaatttc ccgccgatcg tgcgtcgtac ttgggatact    600
gcaaagaaaa tcgaagaaaa attcaaacgt gcgcagctga ccctggacaa gttcttcaag    660
aaacctaagc ttgcggccgc actcgagatc aaacgggcta gccagccaga actcgccccg    720
gaagaccccg aggatgtcga gcaccaccac caccaccact ga                       762
```

<210> SEQ ID NO 82
<211> LENGTH: 762
<212> TYPE: DNA
<213> ORGANISM: Artificial Sequence
<220> FEATURE:
<223> OTHER INFORMATION: SYNTHETIC SEQUENCE

<400> SEQUENCE: 82

```
atgaaagttg caggtgcaga tgaagctggt cgtggtccag ttattggtcc gctggttatt     60
gttgctgctg ttgtggatga aacagtctc cccaagctgg aagagctgaa agttagagac    120
tccaaaaagc tgaccccgaa gcgacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg tagatgccgc tgatgttgat gaagaacgtt tcgctagaga gcttggcgag    360
cgtctgaact tcgaagcgga agttgtagcc aaacataaag cggatgacat ctttccggtc    420
gtatccgcag cctctatcct ggcaaaagtt atccgtgacc gcgagatcga aaagctgaaa    480
gccgaatacg gtgattttgg ttccggttac ccgtctgatc cgcgtactaa gaaatggctg    540
```

```
gaagaatggt atagcaaaca cggcaatttc ccgccgatcg tgcgtcgtac ttgggatact    600
gcaaagaaaa tcgaagaaaa attcaaacgt gcgcagctga ccctggacaa gttcttcaag    660
aaacctaagc ttgcggccgc actcgagatc aaacgggcta gccagccaga actcgccccg    720
gaagaccccg aggatgtcga gcaccaccac caccaccact ga                       762
```

<210> SEQ ID NO 83
<211> LENGTH: 762
<212> TYPE: DNA
<213> ORGANISM: Artificial Sequence
<220> FEATURE:
<223> OTHER INFORMATION: SYNTHETIC SEQUENCE

<400> SEQUENCE: 83

```
atgaaagttg caggtgcaga tgaagctggt cgtggttctg ttattggtcc gctggttatt     60
gttgctgctg ttgtggatga aacagtctc cccaagctgg aagagctgaa agttagagac    120
tccaaaaagc tgaccccgaa gcgacgtgaa aaactgttcg atgaaatcgt aaaagtactg   180
gatgattact ctgtggtcat tgtgtccccg caggacattg acggtcgtaa gggcagcatg   240
aacgaactgg aggtagaaaa cttcgttaaa gccctgaata gcctgaaagt taagccggat   300
gttatttacg tagatgccgc tgatgttgat gaagaacgtt tcgctagaga gcttggcgag   360
cgtctgaact tcgaagcgga agttgtagcc aaacataaag cggatgacat ctttccggtc   420
gtatccgcag cctctatcct ggcaaaagtt atccgtgacc gcgagatcga aaagctgaaa   480
gccgaatacg gtgattttgg ttccggttac ccgtctgatc cgcgtactaa gaaatggctg   540
gaagaatggt atagcaaaca cggcaatttc ccgccgatcg tgcgtcgtac ttgggatact   600
gcaaagaaaa tcgaagaaaa attcaaacgt gcgcagctga ccctggacaa gttcttcaag   660
aaacctaagc ttgcggccgc actcgagatc aaacgggcta gccagccaga actcgccccg   720
gaagaccccg aggatgtcga gcaccaccac caccaccact ga                      762
```

<210> SEQ ID NO 84
<211> LENGTH: 780
<212> TYPE: DNA
<213> ORGANISM: Artificial Sequence
<220> FEATURE:
<223> OTHER INFORMATION: SYNTHETIC SEQUENCE

<400> SEQUENCE: 84

```
atgaaagttg caggtataga tgaagctggt cgtggttctg ctattggtcc gctggttatt     60
gttgctgctg ttgtggatga aacagtctc cccaagctgg aagagctgaa agttagagac    120
tccaaaaagc tgaccccggc gcaacgtgaa aaactgttcg atgaaatcgt aaaagtactg   180
gatgattact ctgtggtcat tgtgtccccg caggacattg acggtcgtaa gggcagcatg   240
aacgaactgg aggtagaaaa cttcgttaaa gccctgaata gcctgaaagt taagccggat   300
gttatttacg ctgatgccgc tgatgttgat gaagaacgtt tcgctagaga gcttggcgag   360
cgtctgaact tcgaagcgaa agttgtagcc gaacataaag cggatgcgaa gtatgagatc   420
gtatccgcag cctctatcct ggcaaaagtt atccgtgacc gcgagatcga aaagctgaaa   480
gccgaatacg gtgattttgg ttccggttac ccgtctgatc cgcgtactag ggcattcctg   540
gaaaattact atagagaaca cggcgaattc ccgccgatcg tgcgtaaagg ttggaagact   600
ctaaagaaaa tcgcagaaaa agtcgaaagt gagaagaagg ctgaggaacg gcaggcgacc   660
ctggacaggt acttcaggaa ggttaagctt gcggccgcac tcgagatcaa acgggctagc   720
cagccagaac tcgcccgga agaccccgag gatgtcgagc accaccacca ccaccactga   780
```

<210> SEQ ID NO 85
<211> LENGTH: 780
<212> TYPE: DNA
<213> ORGANISM: Artificial Sequence
<220> FEATURE:
<223> OTHER INFORMATION: SYNTHETIC SEQUENCE

<400> SEQUENCE: 85

```
atgaaagttg caggtataga tgaagctggt cgtggtccag ctattggtcc gctggttatt      60
gttgctgctg ttgtggatga aaacagtctc cccaagctgg aagagctgaa agttagagac     120
tccaaaaagc tgaccccggc gcgccgtgaa aaactgttcg atgaaatcgt aaaagtactg     180
gatgattact ctgtggtcat tgtgtccccg caggacattg acggtcgtaa gggcagcatg     240
aacgaactgg aggtagaaaa cttcgttaaa gccctgaata gcctgaaagt taagccggat     300
gttatttacg ctgatgccgc tgatgttgat gaagaacgtt tcgctagaga gcttggcgag     360
cgtctgaact tcgaagcgaa agttgtagcc aacataaag cggatgcgaa gtatgagatc      420
gtatccgcag cctctatcct ggcaaaagtt atccgtgacc gcgagatcga aaagctgaaa     480
gccgaatacg tgattttggt tccggttac ccgtctgatc cgcgtactag ggcattcctg       540
gaaaattact atagagaaca cggcgaattc ccgccgatcg tgcgtaaagg ttggaagact     600
ctaaagaaaa tcgcagaaaa agtcgaaagt gagaagaagg ctgaggaacg gcaggcgacc     660
ctggacaggt acttcaggaa ggttaagctt gcggccgcac tcgagatcaa acgggctagc    720
cagccagaac tcgccccgga agaccccgag gatgtcgagc accaccaca ccaccactga       780
```

<210> SEQ ID NO 86
<211> LENGTH: 780
<212> TYPE: DNA
<213> ORGANISM: Artificial Sequence
<220> FEATURE:
<223> OTHER INFORMATION: SYNTHETIC SEQUENCE

<400> SEQUENCE: 86

```
atgaaagttg caggtataga tgaagctggt cgtggtccag ctattggtcc gctggttatt      60
gttgctgctg ttgtggatga aaacagtctc cccaagctgg aagagctgaa agttagagac     120
tccaaaaagc tgaccccggc gcaacgtgaa aaactgttcg atgaaatcgt aaaagtactg     180
gatgattact ctgtggtcat tgtgtccccg caggacattg acggtcgtaa gggcagcatg     240
aacgaactgg aggtagaaaa cttcgttaaa gccctgaata gcctgaaagt taagccggat     300
gttatttacg ctgatgccgt agatgttgat gaagaacgtt tcgctagaga gcttggcgag     360
cgtctgaact tcgaagcgaa agttgtagcc aacataaag cggatgcgaa gtatgagatc      420
gtatccgcag cctctatcct ggcaaaagtt atccgtgacc gcgagatcga aaagctgaaa     480
gccgaatacg tgattttggt tccggttac ccgtctgatc cgcgtactag ggcattcctg       540
gaaaattact atagagaaca cggcgaattc ccgccgatcg tgcgtaaagg ttggaagact     600
ctaaagaaaa tcgcagaaaa agtcgaaagt gagaagaagg ctgaggaacg gcaggcgacc     660
ctggacaggt acttcaggaa ggttaagctt gcggccgcac tcgagatcaa acgggctagc    720
cagccagaac tcgccccgga agaccccgag gatgtcgagc accaccacca ccaccactga     780
```

<210> SEQ ID NO 87
<211> LENGTH: 780
<212> TYPE: DNA
<213> ORGANISM: Artificial Sequence
<220> FEATURE:

<223> OTHER INFORMATION: SYNTHETIC SEQUENCE

<400> SEQUENCE: 87

```
atgaaagttg caggtataga tgaagctggt cgtggttctg ctattggtcc gctggttatt    60
gttgctgctg ttgtggatga aaacagtctc cccaagctgg aagagctgaa agttagagac   120
tccaaaaagc tgaccccggc gcaacgtgaa aaactgttcg atgaaatcgt aaaagtactg   180
gatgattact ctgtggtcat tgtgtccccg caggacattg acggtcgtaa gggcagcatg   240
aacgaactgg aggtagaaaa cttcgttaaa gccctgaata gcctgaaagt taagccggat   300
gttatttacg ctgatgccgt agatgttgat gaagaacgtt tcgctagaga gcttggcgag   360
cgtctgaact tcgaagcgaa agttgtagcc gaacataaag cggatgcgaa gtatgagatc   420
gtatccgcag cctctatcct ggcaaaagtt atccgtgacc gcgagatcga aaagctgaaa   480
gccgaatacg gtgattttgg ttccggttac ccgtctgatc cgcgtactag ggcattcctg   540
gaaaattact atagagaaca cggcgaattc ccgccgatcg tgcgtaaagg ttggaagact   600
ctaaagaaaa tcgcagaaaa agtcgaaagt gagaagaagg ctgaggaacg gcaggcgacc   660
ctggacaggt acttcaggaa ggttaagctt gcggccgcac tcgagatcaa cgggctagc   720
cagccagaac tcgccccgga agaccccgag gatgtcgagc accaccacca ccaccactga   780
```

<210> SEQ ID NO 88
<211> LENGTH: 222
<212> TYPE: PRT
<213> ORGANISM: Artificial Sequence
<220> FEATURE:
<223> OTHER INFORMATION: SYNTHETIC SEQUENCE

<400> SEQUENCE: 88

```
Met Lys Val Ala Gly Ala Asp Glu Ala Gly Arg Gly Ser Val Ile Gly
  1               5                  10                  15

Pro Leu Val Ile Val Ala Ala Val Val Asp Glu Asn Ser Leu Pro Lys
             20                  25                  30

Leu Glu Glu Leu Lys Val Arg Asp Ser Lys Lys Leu Thr Pro Lys Arg
         35                  40                  45

Arg Glu Lys Leu Phe Asp Glu Ile Val Lys Val Leu Asp Asp Tyr Ser
     50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                 85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205
```

-continued

Lys Arg Ala Gln Leu Thr Leu Asp Lys Phe Phe Lys Lys Pro
    210                 215                 220

<210> SEQ ID NO 89
<211> LENGTH: 222
<212> TYPE: PRT
<213> ORGANISM: Artificial Sequence
<220> FEATURE:
<223> OTHER INFORMATION: SYNTHETIC SEQUENCE

<400> SEQUENCE: 89

Met Lys Val Ala Gly Ala Asp Glu Ala Gly Arg Gly Pro Val Ile Gly
1               5                   10                  15

Pro Leu Val Ile Val Ala Ala Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Val Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Lys Phe Phe Lys Lys Pro
    210                 215                 220

<210> SEQ ID NO 90
<211> LENGTH: 222
<212> TYPE: PRT
<213> ORGANISM: Artificial Sequence
<220> FEATURE:
<223> OTHER INFORMATION: SYNTHETIC SEQUENCE

<400> SEQUENCE: 90

Met Lys Val Ala Gly Ala Asp Glu Ala Gly Arg Gly Ser Val Ile Gly
1               5                   10                  15

Pro Leu Val Ile Val Ala Ala Val Val Asp Glu Asn Ser Leu Pro Lys
                20                  25                  30

Leu Glu Glu Leu Lys Val Arg Asp Ser Lys Lys Leu Thr Pro Lys Arg
            35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

```
Asn Glu Leu Glu Val Glu Asn Phe Val Lys Ala Leu Asn Ser Leu Lys
                85                  90                  95

Val Lys Pro Asp Val Ile Tyr Ala Asp Ala Val Asp Val Asp Glu Glu
            100                 105                 110

Arg Phe Ala Arg Glu Leu Gly Glu Arg Leu Asn Phe Glu Ala Glu Val
        115                 120                 125

Val Ala Lys His Lys Ala Asp Asp Ile Phe Pro Val Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Lys Lys Trp Leu Glu Glu Trp Tyr Ser Lys His Gly Asn Phe Pro Pro
            180                 185                 190

Ile Val Arg Arg Thr Trp Asp Thr Ala Lys Lys Ile Glu Glu Lys Phe
        195                 200                 205

Lys Arg Ala Gln Leu Thr Leu Asp Lys Phe Phe Lys Lys Pro
    210                 215                 220

<210> SEQ ID NO 91
<211> LENGTH: 228
<212> TYPE: PRT
<213> ORGANISM: Artificial Sequence
<220> FEATURE:
<223> OTHER INFORMATION: SYNTHETIC SEQUENCE

<400> SEQUENCE: 91

Met Lys Val Ala Gly Ile Asp Glu Ala Gly Arg Gly Ser Ala Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Ala Gln
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Leu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220
```

-continued

Phe Arg Lys Val
225

<210> SEQ ID NO 92
<211> LENGTH: 228
<212> TYPE: PRT
<213> ORGANISM: Artificial Sequence
<220> FEATURE:
<223> OTHER INFORMATION: SYNTHETIC SEQUENCE

<400> SEQUENCE: 92

Met Lys Val Ala Gly Ile Asp Glu Ala Gly Arg Gly Pro Ala Ile Gly
1               5                   10                  15

Pro Leu Val Ile Val Ala Ala Val Val Asp Glu Asn Ser Leu Pro Lys
            20                  25                  30

Leu Glu Glu Leu Lys Val Arg Asp Ser Lys Lys Leu Thr Pro Ala Arg
        35                  40                  45

Arg Glu Lys Leu Phe Asp Glu Ile Val Lys Val Leu Asp Asp Tyr Ser
    50                  55                  60

Val Val Ile Val Ser Pro Gln Asp Ile Asp Gly Arg Lys Gly Ser Met
65                  70                  75                  80

Asn Glu Leu Glu Val Glu Asn Phe Val Lys Ala Leu Asn Ser Leu Lys
                85                  90                  95

Val Lys Pro Asp Val Ile Tyr Ala Asp Ala Ala Asp Val Asp Glu Glu
            100                 105                 110

Arg Phe Ala Arg Glu Leu Gly Glu Arg Leu Asn Phe Glu Ala Lys Val
        115                 120                 125

Val Ala Glu His Lys Ala Asp Ala Lys Tyr Glu Ile Val Ser Ala Ala
    130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220

Phe Arg Lys Val
225

<210> SEQ ID NO 93
<211> LENGTH: 228
<212> TYPE: PRT
<213> ORGANISM: Artificial Sequence
<220> FEATURE:
<223> OTHER INFORMATION: SYNTHETIC SEQUENCE

<400> SEQUENCE: 93

Met Lys Val Ala Gly Ile Asp Glu Ala Gly Arg Gly Pro Ala Ile Gly
1               5                   10                  15

Pro Leu Val Ile Val Ala Ala Val Asp Glu Asn Ser Leu Pro Lys
            20                  25                  30

Leu Glu Glu Leu Lys Val Arg Asp Ser Lys Lys Leu Thr Pro Ala Gln
        35                  40                  45

Arg Glu Lys Leu Phe Asp Glu Ile Val Lys Val Leu Asp Asp Tyr Ser

```
            50                  55                  60
Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                     85                  90                  95

Val Lys Pro Asp Val Ile Tyr Ala Asp Ala Val Asp Val Asp Glu Glu
                100                 105                 110

Arg Phe Ala Arg Glu Leu Gly Glu Arg Leu Asn Phe Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
            180                 185                 190

Ile Val Arg Lys Gly Trp Lys Thr Leu Lys Lys Ile Ala Glu Lys Val
        195                 200                 205

Glu Ser Glu Lys Lys Ala Glu Glu Arg Gln Ala Thr Leu Asp Arg Tyr
    210                 215                 220

Phe Arg Lys Val
225

<210> SEQ ID NO 94
<211> LENGTH: 228
<212> TYPE: PRT
<213> ORGANISM: Artificial Sequence
<220> FEATURE:
<223> OTHER INFORMATION: SYNTHETIC SEQUENCE

<400> SEQUENCE: 94

Met Lys Val Ala Gly Ile Asp Glu Ala Gly Arg Gly Ser Ala Ile Gly
  1               5                  10                  15

Pro Leu Val Ile Val Ala Ala Val Val Asp Glu Asn Ser Leu Pro Lys
                 20                  25                  30

Leu Glu Glu Leu Lys Val Arg Asp Ser Lys Lys Leu Thr Pro Ala Gln
             35                  40                  45

Arg Glu Lys Leu Phe Asp Glu Ile Lys Val Leu Asp Asp Tyr Ser
         50                  55                  60

Val Val Ile Val Ser Pro Gln Asp Ile Asp Gly Arg Lys Gly Ser Met
 65                  70                  75                  80

Asn Glu Leu Glu Val Glu Asn Phe Val Lys Ala Leu Asn Ser Leu Lys
                     85                  90                  95

Val Lys Pro Asp Val Ile Tyr Ala Asp Ala Val Asp Val Asp Glu Glu
                100                 105                 110

Arg Phe Ala Arg Glu Leu Gly Glu Arg Leu Asn Phe Glu Ala Lys Val
            115                 120                 125

Val Ala Glu His Lys Ala Asp Ala Lys Tyr Glu Ile Val Ser Ala Ala
        130                 135                 140

Ser Ile Leu Ala Lys Val Ile Arg Asp Arg Glu Ile Glu Lys Leu Lys
145                 150                 155                 160

Ala Glu Tyr Gly Asp Phe Gly Ser Gly Tyr Pro Ser Asp Pro Arg Thr
                165                 170                 175

Arg Ala Phe Leu Glu Asn Tyr Tyr Arg Glu His Gly Glu Phe Pro Pro
```

```
               180              185              190
Ile Val Arg Lys Gly Trp Lys Thr Leu Lys Lys Ile Ala Glu Lys Val
                195                  200                  205
Glu Ser Glu Lys Lys Ala Glu Glu Arg Gln Ala Thr Leu Asp Arg Tyr
        210                  215                  220
Phe Arg Lys Val
225

<210> SEQ ID NO 95
<211> LENGTH: 669
<212> TYPE: DNA
<213> ORGANISM: Artificial Sequence
<220> FEATURE:
<223> OTHER INFORMATION: SYNTHETIC SEQUENCE

<400> SEQUENCE: 95
atgaaagttg caggtgcaga tgaagctggt cgtggttctg ttattggtcc gctggttatt      60
gttgctgctg ttgtggatga aacagtctc cccaagctgg aagagctgaa agttagagac     120
tccaaaaagc tgaccccgaa gcgacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg ctgatgccgc tgatgttgat gaagaacgtt tcgctagaga gcttggcgag    360
cgtctgaact tcgaagcgga agttgtagcc aaacataaag cggatgacat ctttccggtc    420
gtatccgcag cctctatcct ggcaaaagtt atccgtgacc gcgagatcga aaagctgaaa    480
gccgaatacg gtgattttgg ttccggttac ccgtctgatc cgcgtactaa gaaatggctg    540
gaagaatggt atagcaaaca cggcaatttc ccgccgatcg tgcgtcgtac ttgggatact    600
gcaaagaaaa tcgaagaaaa attcaaacgt gcgcagctga ccctggacaa gttcttcaag    660
aaaccttga                                                            669

<210> SEQ ID NO 96
<211> LENGTH: 669
<212> TYPE: DNA
<213> ORGANISM: Artificial Sequence
<220> FEATURE:
<223> OTHER INFORMATION: SYNTHETIC SEQUENCE

<400> SEQUENCE: 96
atgaaagttg caggtgcaga tgaagctggt cgtggtccag ttattggtcc gctggttatt      60
gttgctgctg ttgtggatga aacagtctc cccaagctgg aagagctgaa agttagagac     120
tccaaaaagc tgaccccgaa gcgacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg tagatgccgc tgatgttgat gaagaacgtt tcgctagaga gcttggcgag    360
cgtctgaact tcgaagcgga agttgtagcc aaacataaag cggatgacat ctttccggtc    420
gtatccgcag cctctatcct ggcaaaagtt atccgtgacc gcgagatcga aaagctgaaa    480
gccgaatacg gtgattttgg ttccggttac ccgtctgatc cgcgtactaa gaaatggctg    540
gaagaatggt atagcaaaca cggcaatttc ccgccgatcg tgcgtcgtac ttgggatact    600
gcaaagaaaa tcgaagaaaa attcaaacgt gcgcagctga ccctggacaa gttcttcaag    660
aaaccttga                                                            669
```

<210> SEQ ID NO 97
<211> LENGTH: 669
<212> TYPE: DNA
<213> ORGANISM: Artificial Sequence
<220> FEATURE:
<223> OTHER INFORMATION: SYNTHETIC SEQUENCE

<400> SEQUENCE: 97

```
atgaaagttg caggtgcaga tgaagctggt cgtggttctg ttattggtcc gctggttatt      60
gttgctgctg ttgtggatga aacagtctc cccaagctgg aagagctgaa agttagagac     120
tccaaaaagc tgaccccgaa gcgacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg tagatgccgc tgatgttgat gaagaacgtt tcgctagaga gcttggcgag    360
cgtctgaact tcaagcgga agttgtagcc aaacataaag cggatgacat ctttccggtc    420
gtatccgcag cctctatcct ggcaaaagtt atccgtgacc gcgagatcga aaagctgaaa    480
gccgaatacg gtgattttgg ttccggttac ccgtctgatc cgcgtactaa gaatggctg    540
gaagaatggt atagcaaaca cggcaatttc ccgccgatcg tgcgtcgtac ttgggatact    600
gcaaagaaaa tcgaagaaaa attcaaacgt gcgcagctga ccctggacaa gttcttcaag    660
aaaccttga                                                             669
```

<210> SEQ ID NO 98
<211> LENGTH: 687
<212> TYPE: DNA
<213> ORGANISM: Artificial Sequence
<220> FEATURE:
<223> OTHER INFORMATION: SYNTHETIC SEQUENCE

<400> SEQUENCE: 98

```
atgaaagttg caggtataga tgaagctggt cgtggttctg ctattggtcc gctggttatt      60
gttgctgctg ttgtggatga aacagtctc cccaagctgg aagagctgaa agttagagac     120
tccaaaaagc tgaccccggc gcaacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg ctgatgccgc tgatgttgat gaagaacgtt tcgctagaga gcttggcgag    360
cgtctgaact tcaagcgaa agttgtagcc gaacataaag cggatgcgaa gtatgagatc    420
gtatccgcag cctctatcct ggcaaaagtt atccgtgacc gcgagatcga aaagctgaaa    480
gccgaatacg gtgattttgg ttccggttac ccgtctgatc cgcgtactag gcattcctg    540
gaaaattact atagagaaca cggcgaattc ccgccgatcg tgcgtaaagg ttggaagact    600
ctaaagaaaa tcgcagaaaa agtcgaaagt gagaagaagg ctgaggaacg gcaggcgacc    660
ctggacaggt acttcaggaa ggtttga                                         687
```

<210> SEQ ID NO 99
<211> LENGTH: 687
<212> TYPE: DNA
<213> ORGANISM: Artificial Sequence
<220> FEATURE:
<223> OTHER INFORMATION: SYNTHETIC SEQUENCE

<400> SEQUENCE: 99

```
atgaaagttg caggtataga tgaagctggt cgtggtccag ctattggtcc gctggttatt      60
```

```
gttgctgctg ttgtggatga aaacagtctc cccaagctgg aagagctgaa agttagagac    120
tccaaaaagc tgaccccggc gcgccgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg ctgatgccgc tgatgttgat gaagaacgtt tcgctagaga gcttggcgag    360
cgtctgaact tcgaagcgaa agttgtagcc gaacataaag cggatgcgaa gtatgagatc    420
gtatccgcag cctctatcct ggcaaaagtt atccgtgacc gcgagatcga aaagctgaaa    480
gccgaatacg gtgattttgg ttccggttac ccgtctgatc cgcgtactag ggcattcctg    540
gaaaattact atagagaaca cggcgaattc ccgccgatcg tgcgtaaagg ttggaagact    600
ctaaagaaaa tcgcagaaaa agtcgaaagt gagaagaagg ctgaggaacg gcaggcgacc    660
ctggacaggt acttcaggaa ggtttga                                        687
```

<210> SEQ ID NO 100
<211> LENGTH: 687
<212> TYPE: DNA
<213> ORGANISM: Artificial Sequence
<220> FEATURE:
<223> OTHER INFORMATION: SYNTHETIC SEQUENCE

<400> SEQUENCE: 100

```
atgaaagttg caggtataga tgaagctggt cgtggtccag ctattggtcc gctggttatt     60
gttgctgctg ttgtggatga aaacagtctc cccaagctgg aagagctgaa agttagagac    120
tccaaaaagc tgaccccggc gcaacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg ctgatgccgt agatgttgat gaagaacgtt tcgctagaga gcttggcgag    360
cgtctgaact tcgaagcgaa agttgtagcc gaacataaag cggatgcgaa gtatgagatc    420
gtatccgcag cctctatcct ggcaaaagtt atccgtgacc gcgagatcga aaagctgaaa    480
gccgaatacg gtgattttgg ttccggttac ccgtctgatc cgcgtactag ggcattcctg    540
gaaaattact atagagaaca cggcgaattc ccgccgatcg tgcgtaaagg ttggaagact    600
ctaaagaaaa tcgcagaaaa agtcgaaagt gagaagaagg ctgaggaacg gcaggcgacc    660
ctggacaggt acttcaggaa ggtttga                                        687
```

<210> SEQ ID NO 101
<211> LENGTH: 687
<212> TYPE: DNA
<213> ORGANISM: Artificial Sequence
<220> FEATURE:
<223> OTHER INFORMATION: SYNTHETIC SEQUENCE

<400> SEQUENCE: 101

```
atgaaagttg caggtataga tgaagctggt cgtggttctg ctattggtcc gctggttatt     60
gttgctgctg ttgtggatga aaacagtctc cccaagctgg aagagctgaa agttagagac    120
tccaaaaagc tgaccccggc gcaacgtgaa aaactgttcg atgaaatcgt aaaagtactg    180
gatgattact ctgtggtcat tgtgtccccg caggacattg acggtcgtaa gggcagcatg    240
aacgaactgg aggtagaaaa cttcgttaaa gccctgaata gcctgaaagt taagccggat    300
gttatttacg ctgatgccgt agatgttgat gaagaacgtt tcgctagaga gcttggcgag    360
```

-continued

```
cgtctgaact tcgaagcgaa agttgtagcc gaacataaag cggatgcgaa gtatgagatc      420
gtatccgcag cctctatcct ggcaaaagtt atccgtgacc gcgagatcga aaagctgaaa      480
gccgaatacg gtgattttgg ttccggttac ccgtctgatc cgcgtactag ggcattcctg      540
gaaaattact atagagaaca cggcgaattc ccgccgatcg tgcgtaaagg ttggaagact      600
ctaaagaaaa tcgcagaaaa agtcgaaagt gagaagaagg ctgaggaacg gcaggcgacc      660
ctggacaggt acttcaggaa ggtttga                                          687
```